(12) United States Patent
Chambers et al.

(10) Patent No.: US 11,248,046 B2
(45) Date of Patent: Feb. 15, 2022

(54) CLAUDIN 6 ANTIBODIES AND USES THEREOF

(71) Applicant: Integral Molecular, Inc., Philadelphia, PA (US)

(72) Inventors: Ross Chambers, Philadelphia, PA (US); Joseph Rucker, Philadelphia, PA (US); Thomas Charpentier, Philadelphia, PA (US); Lewis J. Stafford, Philadelphia, PA (US); Brad Screnci, Philadelphia, PA (US); Trevor Barnes, Philadelphia, PA (US); Benjamin Doranz, Philadelphia, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 0 days.

(21) Appl. No.: 16/790,066

(22) Filed: Feb. 13, 2020

(65) Prior Publication Data
US 2020/0262915 A1     Aug. 20, 2020

Related U.S. Application Data

(60) Provisional application No. 62/806,048, filed on Feb. 15, 2019.

(51) Int. Cl.
   *C07K 16/28*     (2006.01)
   *A61K 47/68*     (2017.01)

(52) U.S. Cl.
CPC .......... *C07K 16/28* (2013.01); *A61K 47/6849* (2017.08); *C07K 2317/31* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 4,699,880 A | 10/1987 | Goldstein | |
| 4,816,567 A | 3/1989 | Cabilly et al. | |
| 4,946,778 A | 8/1990 | Ladner et al. | |
| 5,260,203 A | 11/1993 | Ladner et al. | |
| 5,475,096 A | 12/1995 | Gold et al. | |
| 5,831,012 A | 11/1998 | Nilsson et al. | |
| 6,004,746 A | 12/1999 | Brent et al. | |
| 6,005,079 A | 12/1999 | Casterman et al. | |
| 6,794,144 B1 | 9/2004 | Saksela et al. | |
| 6,818,418 B1 | 11/2004 | Lipovsek et al. | |
| 6,994,982 B1 | 2/2006 | Watt et al. | |
| 7,105,653 B2 | 9/2006 | Shanafelt et al. | |
| 7,166,697 B1 | 1/2007 | Galanis et al. | |
| 7,186,524 B2 | 3/2007 | Kolmar et al. | |
| 7,250,297 B1 | 7/2007 | Beste et al. | |
| 7,417,130 B2 | 8/2008 | Stumpp et al. | |
| 7,763,258 B2 | 7/2010 | Doms et al. | |
| 7,803,907 B2 | 9/2010 | Stemmer et al. | |
| 7,838,629 B2 | 11/2010 | Fiedler et al. | |
| 8,158,130 B2 | 4/2012 | Doms et al. | |
| 8,377,691 B2 | 2/2013 | Doranz | |
| 9,074,002 B2 | 7/2015 | Tonks et al. | |
| 9,274,119 B2 | 3/2016 | Aburatani et al. | |
| 9,428,567 B2 | 8/2016 | Garcia et al. | |
| 9,580,486 B2 | 2/2017 | Gavin et al. | |
| 9,616,106 B2 | 4/2017 | Basile | |
| 10,053,511 B2 | 8/2018 | Santaguida et al. | |
| 10,336,818 B2 | 7/2019 | Chamberlain et al. | |
| 10,604,568 B2 | 3/2020 | Sahin et al. | |
| 2004/0023334 A1 | 2/2004 | Prior | |
| 2004/0132094 A1 | 7/2004 | Etzerodt et al. | |
| 2004/0141980 A1 | 7/2004 | Ignjatovic et al. | |
| 2004/0146938 A1 | 7/2004 | Nguyen et al. | |
| 2004/0157209 A1 | 8/2004 | Yilmaz et al. | |
| 2004/0209243 A1 | 10/2004 | Nixon et al. | |
| 2005/0123563 A1 | 6/2005 | Doranz et al. | |
| 2006/0269515 A1 | 11/2006 | Denis-Mize et al. | |
| 2010/0119446 A1 | 5/2010 | Grabulovski et al. | |
| 2010/0239633 A1 | 9/2010 | Strome et al. | |
| 2012/0195882 A1 | 8/2012 | Doms et al. | |
| 2012/0301476 A1 | 11/2012 | Okano et al. | |
| 2013/0183305 A1* | 7/2013 | Sahin ................. | C07K 16/3023 424/133.1 |
| 2014/0127219 A1 | 5/2014 | Sahin et al. | |
| 2014/0286898 A1 | 9/2014 | Gavin et al. | |
| 2017/0003712 A1 | 1/2017 | Funk et al. | |
| 2017/0051029 A1 | 2/2017 | Greve | |
| 2017/0355756 A1* | 12/2017 | Julien ................... | C12N 15/86 |
| 2018/0044434 A1 | 2/2018 | Sato et al. | |

(Continued)

FOREIGN PATENT DOCUMENTS

| | | |
|---|---|---|
| CN | 103483449 A | 1/2014 |
| EA | 0171496 | 2/1986 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Koenig "Mutational landscape of antibody variable domains reveals a switch modulating the interdomain conformational dynamics and antigen binding" PNAS E486-E495 (Year: 2017).*
UniProtKB Accession No. A0A2V9M896_9BACT, Sialidase domain-containint protein, (2018).
Bird, et al., "Single-Chain Antigen-Binding Proteins", Science, (1998) vol. 242, pp. 432-426.
(Continued)

*Primary Examiner* — Adam Weidner
(74) *Attorney, Agent, or Firm* — Morgan, Lewis & Bockius LLP

(57) ABSTRACT

Antibodies and compositions against Claudin 6 and uses thereof are provided.

25 Claims, 8 Drawing Sheets

Specification includes a Sequence Listing.

(56) References Cited

U.S. PATENT DOCUMENTS

| | | | |
|---|---|---|---|
| 2019/0083645 | A1 | 3/2019 | Fong et al. |
| 2020/0199221 | A1 | 6/2020 | Mitnacht-Kraus et al. |
| 2020/0262898 | A1 | 8/2020 | Charpentier et al. |
| 2020/0291111 | A1 | 9/2020 | Conklin et al. |

FOREIGN PATENT DOCUMENTS

| | | | |
|---|---|---|---|
| EP | 0125023 A1 | | 11/1984 |
| EP | 0173494 A2 | | 3/1986 |
| EP | 0184187 A2 | | 6/1986 |
| EP | 404097 A3 | | 10/1991 |
| WO | 1986001533 | | 3/1986 |
| WO | 1987002671 A1 | | 5/1987 |
| WO | 198801649 A1 | | 3/1988 |
| WO | 1993011161 A1 | | 6/1993 |
| WO | 1994004678 A1 | | 3/1994 |
| WO | 1994025591 A1 | | 11/1994 |
| WO | WO 2008068048 | * | 6/2008 |
| WO | 2009025759 | | 2/2009 |
| WO | WO 2009/087978 A1 | | 7/2009 |
| WO | 2010085495 A1 | | 7/2010 |
| WO | WO 2011/057788 A1 | | 5/2011 |
| WO | WO 2012/003956 A1 | | 1/2012 |
| WO | WO 2012/156018 A1 | | 11/2012 |
| WO | 2014016737 | | 1/2014 |
| WO | 2014153111 A3 | | 11/2014 |
| WO | WO 2015/014376 A1 | | 2/2015 |
| WO | WO 2015/014870 A1 | | 2/2015 |
| WO | WO 2015/069794 A2 | | 5/2015 |
| WO | 2016025385 A1 | | 2/2016 |
| WO | 2016014428 A3 | | 3/2016 |
| WO | 2016164937 A3 | | 1/2017 |
| WO | WO 2017/096163 A1 | | 6/2017 |
| WO | 2017192567 A1 | | 11/2017 |
| WO | WO 2017/187186 A1 | | 11/2017 |
| WO | WO 2018/054484 A1 | | 3/2018 |
| WO | 2018067198 | | 4/2018 |
| WO | WO 2019/048040 A1 | | 3/2019 |
| WO | WO 2019/048489 A1 | | 3/2019 |
| WO | WO 2019/056023 A2 | | 3/2019 |
| WO | WO 2020/075325 A1 | | 4/2020 |
| WO | WO 2020/168059 A1 | | 8/2020 |
| WO | WO 2020/191342 A1 | | 9/2020 |
| WO | WO 2021/006328 A1 | | 1/2021 |

OTHER PUBLICATIONS

Better et al., "*Escherichia coli* Secretion of an Active Chimeric Antibody Fragment", Science (1988) 240 (4855, 1041-1043.
Liu et al., "Production of a mouse-human chimeric monoclonal antibody to CD20 with potent Fc-dependent biologic activity", J. Immunolo. (1987) 139(10):3521-6.
Nishibori, et al., "Humanization of chicken monoclonal antibody using phage-display system", Molecular Immunology (2006) 43 pp. 634-642.
Tsurushita, et al., "Humanization of a chicken anti-IL-12 monoclonal antibody", Journal of Immunological methods, 2004) 295, pp. 9-19.
Almagro, "Identification of differences in the specificity-determining residues of antibodies that recognize antigens of differenct size: implications for the rational design of antibody repertoires", J. Mol. Reconit. (2004); 17:132-143.
Sahagan, et al., "A genetically engineered murine/human chimeric antibody retains specificity for human tumor-associated antigen.", J. Immunol. (1986) 137:pp. 1066-1074.

Ward, et al., "Binding activities of a repertoire of single immunoglobulin variable domains secreted from *Escherichia coli*", Nature (1989) vol. 341 pp. 544-546.
Kohler, et al., "Continuous cultures of fused cells secreting antibody of predefined specificity", Nature (1975) Vo. 256: pp. 495 497.
Neuberger, et al., "A hapten-specific chimaeric IgE antibody with human physiological effector function", Nature (1985) vol. 314 pp. 268-270.
Hodgson et al., "Making Monoclonals In Microbes", BioTechnology (1991) 9:421-425.
Boulianne, et al., "Production of functional chimaeric mouse/human antibody", Nature (1984) 312:643 646.
Kozbor, et al., "The production of monoclonal antibodies from human lymphocytes", Immunol. Today (1983) 4:72 79.
Cabilly, et al., "Generation of antibody activity from immunoglobulin polypeptide chaings produced in *Escherichia coli*", (1984) Proc. Natl. Acad. Sci USA 81:3273-3277.
Morrison, et al., "Chimeric human antibody molecules: Mouse antigen-binding domains with humane constant region domains", (1984) Proc. Natl. Acad. Sci. USA 81:6851-6855.
Liu, et al., "Chimeric mouse-human IgG1 antibody that can mediate lysis of cancer cells", Proc. Nationl. Acad. Sci. (1987) 84:3439-3433.
Sun, et al., "Chimeric antibody with human constant regions and mouse variable regions directed against carcinoma-associated antigen 7-1A", Proc. Natil. Acad. Sci. (1987) 84:214-218.
Queen, et al., "A humanized antibody that binds to the interleukin 2 receptor", Proc. Natl. Acad. Sci (1989), 86:10029-10032.
Riechmann, et al., "Reshaping human antibodies for therapy", Nature (1988) 332 (6162): vol. pp. 323-327.
Wu et al., "An analysis of the sequences of the variable regions of bence jones proteins and myeloma light chains and their implications for anti-body complementarity", Journal of Experimental Medicine (1970) 132: pp. 211-250.
Chothia, et al., "Canonical Structures for the Hypervariable Regions of Immunoglobulins", Mol. Biol. (1987) 196:901-917.
Lefrance et al., "IMGT unique numbering for immunoglobulin and T cell receptor variable domains and Ig superfamily V-like domains" Developmental & Comparative Immunology (2003) 27:55-77.
Huston et al., "Protein engineering of antibody binding sites Recovery of specific activity in an anti-digoxin single-chain Fv analogue produced in *Escherichia coli*", Proc. Nat. Acad. Sci. (1988) 85:5879-5883.
Wahl et al., "Improved Radioimingin and Tumor Localizaton with Monoclonal F(ab')2", J. Nucl. Med. (1983) 24:316 325.
Lathe et al., "Synthetic oligonucleotide probes deduced from amino acid sequence data. Theroetical and practical considerations", J. Molec. Biol. (1985) 183:1-12.
Muller et al., "Determination of Affinity and Specificity of Anti-Hapten Antibodies by Competitive Radioimmunoassay", Meth. Enzymol. (1983) 92:589-601.
Baert, et al., "Influence of Immunogenicity on the Long-Term Efficacy of Infliximab in Crohn's Disease", New Engl. J. Med. (2003) 348:601-608.
Holliger at al., "Engineered Antibody Fragments and the Rise of Single Domains", Nat. Biotechnol. (2005) 23:1126-1136.
Holliger et al. "Diabodies": Small bivalent and bispecific antibody fragments, Proc Natl. Acad. Sci. USA (1993) 90:6444-5448.
Milgrom et al., "Treatment of Allergic Asthma with Monoclonal Anti-IgE Antibody", (1999) New Engl. J. Med. 341:1966-1973.
Slamon et al. "Use of Chemotherapy Plus a Monoclonal Antibody Against HER2 for Metastatic Breast Cancer that Overexpresses HERZ", New Engl. J. Med. (2001) 344:783-792.
Storz et al., "Intellectual property protection Strategies for future antibody inventions", MAbs. (2011)3(3): 310-317.
Reichmann et al., "Single domain antibodies: comparison of camel VH and camelised human VH domains", J. Immunol Method (1999) 231:25.

\* cited by examiner

FIG. 5
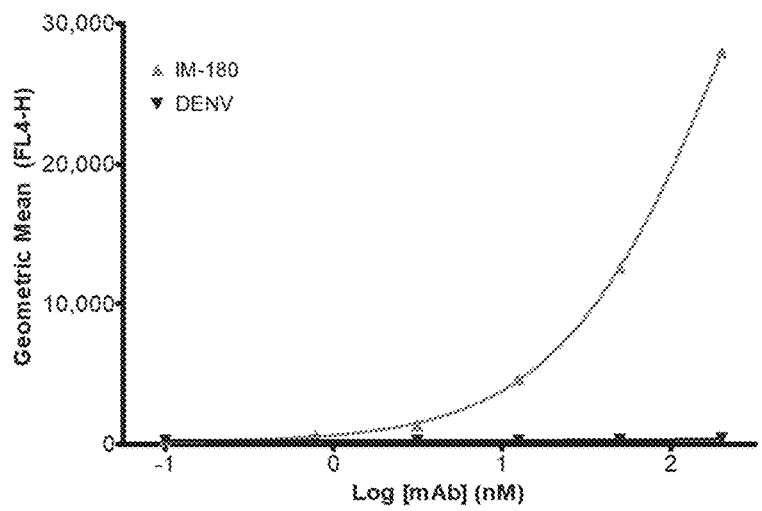
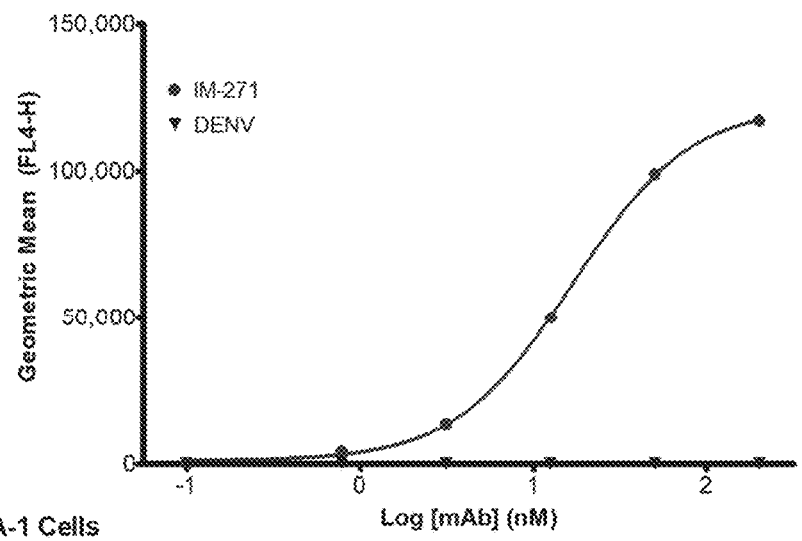
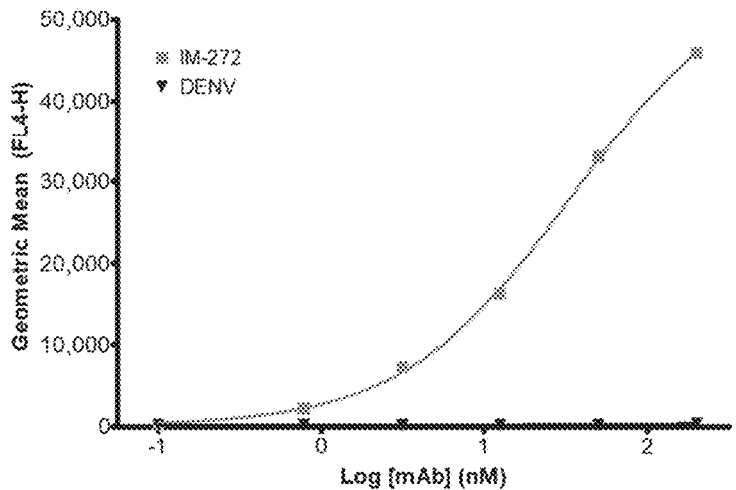

FIG. 8

| Mutation | Binding Reactivity (% WT) | | | | | |
| --- | --- | --- | --- | --- | --- | --- |
| | 3001-D5 MAb | LM136 MAb | LM171 MAb | LM172 Fab | LM173 MAb | 3656 MAb |
| T33A | 356.9 (20) | 202.4 (128) | 22.8 (4) | 71.3 (38) | 116.2 (12) | 130.6 (2) |
| N38A | 57.2 (7) | 78.4 (37) | 22.4 (12) | 3.1 (30) | 86.0 (6) | 90.3 (8) |
| V45A | 12.3 (1) | 85.0 (35) | 88.4 (36) | 250.0 (101) | 76.1 (10) | 108.7 (2) |
| E48A | 11.1 (1) | 5.3 (7) | 0.9 (1) | -10.7 (34) | -0.5 (2) | 151.3 (9) |
| Y67A | 5.9 (2) | 44.2 (14) | 97.2 (11) | -4.0 (26) | 28.8 (5) | 167.6 (39) |
| D68A | 235.2 (74) | 10.2 (6) | 93.7 | 563.4 (482) | 89.6 (4) | 120.1 (33) |
| P74A | 27.7 (4) | 26.5 (11) | 37.5 (16) | 0.1 (16) | 147.1 (32) | 164.0 (12) |
| D76A | 49.2 (17) | 17.9 (1) | 6.0 (1) | 2.2 (19) | 76.8 (11) | 64.3 (0) |
| Q78A | 22.0 (0) | 170.0 (42) | 150.7 (106) | 69.2 (52) | 143.9 (20) | 130.6 (36) |
| D146A | 61.4 (21) | 91.0 (7) | 57.6 (1) | 10.3 (13) | 119.2 (23) | 113.0 (6) |
| V152A | 121.1 (41) | 134.7 (86) | 128.7 (46) | 17.5 (36) | 58.2 (10) | 106.9 (22) |
| A153S | 151.4 | 134.6 (58) | 24.0 (16) | 107.6 (80) | 113.3 (11) | 105.2 (1) |
| E154A | 45.1 (20) | 142.6 (51) | 4.0 (0) | 18.7 (22) | 133.8 (27) | 101.6 (36) |
| Q156A | 179.2 (52) | 190.5 (85) | 102.5 (11) | 2.0 (44) | 0.9 (6) | 150.9 (24) |
| Q156L | 126.0 (64) | 41.7 (26) | 10.0 (3) | -11.8 (35) | 10.7 (8) | 72.5 (4) |
| R158A | 82.0 (14) | 1.3 (1) | 1.3 (0) | 1.3 (29) | 3.6 (1) | 167.4 (10) |

```
SEQUENCE LISTING

<160> NUMBER OF SEQ ID NOS: 147

<210> SEQ ID NO 1
<211> LENGTH: 220
<212> TYPE: PRT
<213> ORGANISM: Homo sapiens

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
                100                 105                 110

Ser Lys Ala Arg Leu Val Leu Thr Ser Gly Ile Val Phe Val Ile Ser
            115                 120                 125
```

```
Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu
                165                 170                 175

Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
            195                 200                 205

Arg Gly Pro Ser Glu Tyr Pro Thr Lys Asn Tyr Val
    210                 215                 220

<210> SEQ ID NO 2
<211> LENGTH: 128
<212> TYPE: PRT
<213> ORGANISM: Artificial Sequence
<220> FEATURE:
<223> OTHER INFORMATION: synthetic sequence

<400> SEQUENCE: 2

Ala Val Thr Leu Asp Glu Ser Gly Gly Gly Leu Gln Thr Pro Gly Gly
1               5                   10                  15

Val Leu Ser Leu Val Cys Lys Ala Ser Gly Phe Ser Phe Ser Ser Tyr
                20                  25                  30

Asp Met Gly Trp Val Arg Gln Ala Pro Gly Lys Gly Leu Glu Trp Val
            35                  40                  45

Ala Ser Ile Tyr Ser Ser Ala Ser Ser Thr Tyr Tyr Ala Pro Ala Val
        50                  55                  60

Lys Gly Arg Ala Thr Ile Thr Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Arg Thr Tyr Arg Gly Trp Ala Thr Tyr Ile Ala
            100                 105                 110

Asp Ser Ile Asp Ala Trp Gly His Gly Thr Glu Val Ile Val Ser Ser
        115                 120                 125

<210> SEQ ID NO 3
<211> LENGTH: 105
<212> TYPE: PRT
<213> ORGANISM: Artificial Sequence
<220> FEATURE:
<223> OTHER INFORMATION: synthetic sequence

<400> SEQUENCE: 3

Ala Leu Thr Gln Pro Ser Ser Val Ser Ala Asn Pro Gly Glu Ser Val
1               5                   10                  15

Glu Ile Thr Cys Ser Gly Asp Ser Ser Trp Tyr Gly Tyr Gly Trp Tyr
                20                  25                  30

Gln Gln Lys Ser Pro Gly Ser Ala Pro Val Thr Leu Ile Tyr Glu Ser
            35                  40                  45

Gly Lys Arg Pro Ser Asp Ile Pro Ser Arg Phe Ser Gly Ser Thr Ser
        50                  55                  60

Gly Ser Thr Ala Thr Leu Thr Ile Thr Gly Val Gln Ala Asp Asp Glu
65                  70                  75                  80

Ala Val Tyr Tyr Cys Gly Ser Ala Asp Ser Asn Ser Ile Gly Ile Phe
```

```
                    85                  90                  95

Gly Ala Gly Thr Thr Leu Thr Val Leu
            100                 105

<210> SEQ ID NO 4
<211> LENGTH: 127
<212> TYPE: PRT
<213> ORGANISM: Artificial Sequence
<220> FEATURE:
<223> OTHER INFORMATION: synthetic sequence

<400> SEQUENCE: 4

Ala Val Thr Leu Asp Glu Ser Gly Gly Leu Gln Thr Pro Gly Gly
1               5                   10                  15

Ala Leu Ser Leu Val Cys Lys Ala Ser Gly Phe Asp Phe Ser Ser Tyr
            20                  25                  30

Ala Met Asn Trp Val Arg Gln Ala Pro Gly Lys Gly Leu Glu Trp Val
        35                  40                  45

Ala Gly Ile Gly Ser Thr Gly Ser Ser Thr Gly Tyr Gly Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Ala Ile Tyr Tyr Cys
                85                  90                  95

Ala Lys Ser Val Gly Asn Gly Asn Ser Trp Ser Gly Tyr Ile Ala Thr
            100                 105                 110

Ser Ile Asp Ala Trp Gly His Gly Thr Glu Val Ile Val Ser Ser
        115                 120                 125

<210> SEQ ID NO 5
<211> LENGTH: 103
<212> TYPE: PRT
<213> ORGANISM: Artificial Sequence
<220> FEATURE:
<223> OTHER INFORMATION: synthetic sequence

<400> SEQUENCE: 5

Ala Leu Thr Gln Pro Ser Ser Val Ser Ala Asn Leu Gly Gly Thr Val
1               5                   10                  15

Lys Leu Thr Cys Ser Gly Gly Ser Ser Gly Tyr Gly Trp Tyr Gln Gln
            20                  25                  30

Lys Ser Pro Gly Ser Ala Pro Val Thr Val Ile Tyr Ser Asn Asp Lys
        35                  40                  45

Arg Pro Ser Asp Ile Pro Ser Arg Phe Ser Gly Ser Leu Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Ser Thr Asp Asn Ser Tyr Val Gly Ile Phe Gly Ala
                85                  90                  95

Gly Thr Thr Leu Thr Val Leu
            100

<210> SEQ ID NO 6
<211> LENGTH: 128
<212> TYPE: PRT
<213> ORGANISM: Artificial Sequence
<220> FEATURE:
<223> OTHER INFORMATION: synthetic sequence

<400> SEQUENCE: 6
```

```
Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Ser Ile Ser Ser Tyr
            20                  25                  30

Thr Met Gln Trp Val Arg Gln Ala Pro Gly Lys Gly Leu Glu Trp Val
            35                  40                  45

Ala Gly Ile Tyr Ser Gly Ser Arg Thr Tyr Tyr Gly Ala Ala Val Gln
        50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Tyr Cys Ala
                85                  90                  95

Lys Ser Ser Tyr Cys Thr Ala Trp Thr Gly Cys Asp Val Tyr Ala Gly
            100                 105                 110

Gly Ser Ile Asp Ala Trp Gly His Gly Thr Glu Val Ile Val Ser Ser
            115                 120                 125

<210> SEQ ID NO 7
<211> LENGTH: 107
<212> TYPE: PRT
<213> ORGANISM: Artificial Sequence
<220> FEATURE:
<223> OTHER INFORMATION: synthetic sequence

<400> SEQUENCE: 7

Ala Leu Thr Gln Pro Ser Ser Val Ser Ala Thr Pro Gly Gly Thr Val
1               5                   10                  15

Glu Ile Thr Cys Ser Gly Asp Ser Ser Asp Asp Gly Ser Tyr Tyr Tyr
            20                  25                  30

Gly Trp Tyr Gln Gln Lys Ser Pro Gly Ser Ala Pro Val Thr Val Ile
            35                  40                  45

Tyr Ser Asn Asp Lys Arg Pro Ser Ser Ile Pro Ser Arg Phe Ser Gly
        50                  55                  60

Ser Ala Ser Gly Ser Thr Ala Thr Leu Thr Ile Thr Gly Val Gln Ala
65                  70                  75                  80

Asp Asp Glu Ala Val Tyr Phe Cys Gly Ser Tyr Asp Ser Ser Thr Gly
                85                  90                  95

Ile Phe Gly Ala Gly Thr Thr Leu Thr Val Leu
            100                 105

<210> SEQ ID NO 8
<211> LENGTH: 126
<212> TYPE: PRT
<213> ORGANISM: Artificial Sequence
<220> FEATURE:
<223> OTHER INFORMATION: synthetic sequence

<400> SEQUENCE: 8

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Ser Met Phe Trp Val Arg Arg Ala Pro Gly Lys Gly Leu Glu Trp Val
            35                  40                  45

Ala Gly Ile Asp Ser Gly Ser Thr Thr Phe Tyr Gly Ser Ala Val Lys
        50                  55                  60

Gly Arg Ala Thr Ile Ser Arg Asp Asn Gly Gln Ser Thr Val Arg Leu
```

```
              65                  70                  75                  80
Gln Leu Asn Asn Leu Arg Ala Glu Asp Thr Ala Thr Tyr Tyr Cys Ala
                    85                  90                  95

Lys Asp Ala Tyr Gly Tyr Cys Gly Trp Ser Gly Cys Ser Ala Asp Ser
                100                 105                 110

Ile Asp Ala Trp Gly His Gly Thr Glu Val Ile Val Ser Ser
                115                 120                 125
```

<210> SEQ ID NO 9
<211> LENGTH: 102
<212> TYPE: PRT
<213> ORGANISM: Artificial Sequence
<220> FEATURE:
<223> OTHER INFORMATION: synthetic sequence

<400> SEQUENCE: 9

```
Ala Leu Thr Gln Pro Ser Ser Val Ser Ala Asn Pro Gly Gly Thr Val
1               5                   10                  15

Glu Ile Thr Cys Ser Gly Gly Asn Asn Tyr Tyr Gly Trp Tyr Gln Gln
                20                  25                  30

Lys Ser Pro Gly Ser Ala Pro Val Thr Val Ile Tyr Tyr Asn Asp Lys
                35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Gly Trp Asp Ser Ser Gly Ile Phe Gly Ala Gly
                85                  90                  95

Thr Thr Leu Thr Val Leu
                100
```

<210> SEQ ID NO 10
<211> LENGTH: 128
<212> TYPE: PRT
<213> ORGANISM: Artificial Sequence
<220> FEATURE:
<223> OTHER INFORMATION: synthetic sequence

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Asp Met Gly Trp Val Arg Gln Ala Pro Gly Lys Gly Leu Glu Trp Val
                35                  40                  45

Ala Ser Ile Tyr Ser Ser Ala Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Gly Arg Thr Tyr Arg Gly Trp Ala Thr Tyr Ile Ala
                100                 105                 110

Asp Ser Ile Asp Ala Trp Gly Gln Gly Thr Leu Val Thr Val Ser Ser
                115                 120                 125
```

<210> SEQ ID NO 11
<211> LENGTH: 106

<212> TYPE: PRT
<213> ORGANISM: Artificial Sequence
<220> FEATURE:
<223> OTHER INFORMATION: synthetic sequence

<400> SEQUENCE: 11

Ser Tyr Glu Leu Thr Gln Pro Pro Ser Val Ser Val Ser Pro Gly Gln
1               5                   10                  15

Thr Ala Arg Ile Thr Cys Ser Gly Asp Ser Ser Trp Tyr Gly Tyr Gly
            20                  25                  30

Trp Tyr Gln Gln Lys Pro Gly Gln Ala Pro Val Leu Val Ile Tyr Glu
        35                  40                  45

Ser Gly Lys Arg Pro Ser Gly Ile Pro Glu Arg Phe Ser Gly Ser Ser
    50                  55                  60

Ser Gly Thr Thr Val Thr Leu Thr Ile Ser Gly Val Gln Ala Glu Asp
65                  70                  75                  80

Glu Ala Asp Tyr Tyr Cys Gly Ser Ala Asp Ser Asn Ser Ile Gly Ile
                85                  90                  95

Phe Gly Gly Gly Thr Lys Leu Thr Val Leu
            100                 105

<210> SEQ ID NO 12
<211> LENGTH: 127
<212> TYPE: PRT
<213> ORGANISM: Artificial Sequence
<220> FEATURE:
<223> OTHER INFORMATION: synthetic sequence

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Ala Met Asn Trp Val Arg Gln Ala Pro Gly Lys Gly Leu Glu Trp Val
        35                  40                  45

Ala Gly Ile Gly Ser Thr Gly Ser Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Gly Asn Gly Asn Ser Trp Ser Gly Tyr Ile Ala Thr
            100                 105                 110

Ser Ile Asp Ala Trp Gly Gln Gly Thr Leu Val Thr Val Ser Ser
        115                 120                 125

<210> SEQ ID NO 13
<211> LENGTH: 104
<212> TYPE: PRT
<213> ORGANISM: Artificial Sequence
<220> FEATURE:
<223> OTHER INFORMATION: synthetic sequence

<400> SEQUENCE: 13

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Ser Gly Tyr Gly Trp Tyr
            20                  25                  30

Gln Gln Lys Pro Gly Gln Ala Pro Val Leu Val Ile Tyr Ser Asn Asp

-continued

```
                35                  40                  45
Lys Arg Pro Ser Gly Ile Pro Glu Arg Phe Ser Gly Ser Ser Gly
 50                  55                  60

Thr Thr Val Thr Leu Thr Ile Ser Gly Val Gln Ala Glu Asp Glu Ala
 65                  70                  75                  80

Asp Tyr Tyr Cys Gly Ser Thr Asp Asn Ser Tyr Val Gly Ile Phe Gly
                 85                  90                  95

Gly Gly Thr Lys Leu Thr Val Leu
            100
```

<210> SEQ ID NO 14
<211> LENGTH: 128
<212> TYPE: PRT
<213> ORGANISM: Artificial Sequence
<220> FEATURE:
<223> OTHER INFORMATION: synthetic sequence

<400> SEQUENCE: 14

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Ile Ser Ser Tyr
             20                  25                  30

Thr Met Gln Trp Val Arg Gln Ala Pro Gly Lys Gly Leu Glu Trp Val
         35                  40                  45

Ala Gly Ile Tyr Ser Gly Ser Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Ser Tyr Cys Thr Ala Trp Thr Gly Cys Asp Val Tyr Ala Gly
            100                 105                 110

Gly Ser Ile Asp Ala Trp Gly Gln Gly Thr Leu Val Thr Val Ser Ser
        115                 120                 125
```

<210> SEQ ID NO 15
<211> LENGTH: 105
<212> TYPE: PRT
<213> ORGANISM: Artificial Sequence
<220> FEATURE:
<223> OTHER INFORMATION: synthetic sequence

<400> SEQUENCE: 15

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Asp Gly Ser Tyr Tyr Tyr Gly
             20                  25                  30

Trp Tyr Gln Gln Lys Pro Gly Gln Ala Pro Val Leu Val Ile Tyr Ser
         35                  40                  45

Asn Asp Lys Arg Pro Ser Gly Ile Pro Glu Arg Phe Ser Gly Ser Ser
 50                  55                  60

Ser Gly Thr Thr Val Thr Leu Thr Ile Ser Gly Val Gln Ala Glu Asp
 65                  70                  75                  80

Glu Ala Asp Tyr Tyr Cys Gly Ser Tyr Asp Ser Ser Thr Gly Ile Phe
                 85                  90                  95

Gly Gly Gly Thr Lys Leu Thr Val Leu
            100                 105
```

```
<210> SEQ ID NO 16
<211> LENGTH: 126
<212> TYPE: PRT
<213> ORGANISM: Artificial Sequence
<220> FEATURE:
<223> OTHER INFORMATION: synthetic sequence

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Phe Trp Val Arg Gln Ala Pro Gly Lys Gly Leu Glu Trp Val
        35                  40                  45

Ala Gly Ile Asp Ser Gly Ser Thr Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Ala Tyr Gly Tyr Cys Gly Trp Ser Gly Cys Ser Ala Asp Ser
            100                 105                 110

Ile Asp Ala Trp Gly Gln Gly Thr Leu Val Thr Val Ser Ser
        115                 120                 125

<210> SEQ ID NO 17
<211> LENGTH: 103
<212> TYPE: PRT
<213> ORGANISM: Artificial Sequence
<220> FEATURE:
<223> OTHER INFORMATION: synthetic sequence

<400> SEQUENCE: 17

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Asn Tyr Tyr Gly Trp Tyr
            20                  25                  30

Gln Gln Lys Pro Gly Gln Ala Pro Val Leu Val Ile Tyr Tyr Asn Asp
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Gly Trp Asp Ser Ser Gly Ile Phe Gly Gly
                85                  90                  95

Gly Thr Lys Leu Thr Val Leu
            100

<210> SEQ ID NO 18
<211> LENGTH: 127
<212> TYPE: PRT
<213> ORGANISM: Artificial Sequence
<220> FEATURE:
<223> OTHER INFORMATION: synthetic sequence

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ala Met Ser Trp Val Arg Gln Ala Pro Gly Lys Gly Leu Glu Trp Val
            35                  40                  45

Ala Gly Ile Ser Ser Ser Gly Arg Tyr Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Val Gly Asn Gly Asn Ser Trp Ser Gly Tyr Ile Ala Thr
            100                 105                 110

Ser Ile Asp Ala Trp Gly Gln Gly Thr Leu Val Thr Val Ser Ser
            115                 120                 125

<210> SEQ ID NO 19
<211> LENGTH: 105
<212> TYPE: PRT
<213> ORGANISM: Artificial Sequence
<220> FEATURE:
<223> OTHER INFORMATION: synthetic sequence

<400> SEQUENCE: 19

Ser Tyr Glu Leu Thr Gln Pro Pro Ser Val Ser Val Ser Pro Gly Gln
 1               5                  10                  15

Thr Ala Arg Ile Thr Cys Ser Gly Gly Ser Gly Ser Tyr Gly Trp Tyr
            20                  25                  30

Gln Gln Lys Pro Gly Gln Ala Pro Val Leu Val Ile Tyr Gly Thr Asn
            35                  40                  45

Lys Arg Pro Ser Gly Ile Pro Glu Arg Phe Ser Gly Ser Ser Ser Gly
 50                  55                  60

Thr Thr Val Thr Leu Thr Ile Ser Gly Val Gln Ala Glu Asp Glu Ala
 65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105

<210> SEQ ID NO 20
<211> LENGTH: 127
<212> TYPE: PRT
<213> ORGANISM: Artificial Sequence
<220> FEATURE:
<223> OTHER INFORMATION: synthetic sequence

<400> SEQUENCE: 20

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ala Gly Ile Ser Ser Ser Gly Arg Tyr Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Lys Ser Val Gly Asn Gly Asn Ser Trp Ser Gly Tyr Ile Ala Thr
            100                 105                 110

Ser Ile Asp Ala Trp Gly Gln Gly Thr Leu Val Thr Val Ser Ser
        115                 120                 125

<210> SEQ ID NO 21
<211> LENGTH: 105
<212> TYPE: PRT
<213> ORGANISM: Artificial Sequence
<220> FEATURE:
<223> OTHER INFORMATION: synthetic sequence

<400> SEQUENCE: 21

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Trp Tyr
            20                  25                  30

Gln Gln Lys Pro Gly Gln Ala Pro Val Thr Val Ile Tyr Gly Thr Asn
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105

<210> SEQ ID NO 22
<211> LENGTH: 11
<212> TYPE: PRT
<213> ORGANISM: Artificial Sequence
<220> FEATURE:
<223> OTHER INFORMATION: synthetic sequence

<400> SEQUENCE: 22

Cys Ser Gly Asp Ser Ser Trp Tyr Gly Tyr Gly
1               5                   10

<210> SEQ ID NO 23
<211> LENGTH: 8
<212> TYPE: PRT
<213> ORGANISM: Artificial Sequence
<220> FEATURE:
<223> OTHER INFORMATION: synthetic sequence

<400> SEQUENCE: 23

Ile Tyr Glu Ser Gly Lys Arg Pro
1               5

<210> SEQ ID NO 24
<211> LENGTH: 12
<212> TYPE: PRT
<213> ORGANISM: Artificial Sequence
<220> FEATURE:
<223> OTHER INFORMATION: synthetic sequence

<400> SEQUENCE: 24

Cys Gly Ser Ala Asp Ser Asn Ser Ile Gly Ile Phe
1               5                   10

<210> SEQ ID NO 25
<211> LENGTH: 12

```
<212> TYPE: PRT
<213> ORGANISM: Artificial Sequence
<220> FEATURE:
<223> OTHER INFORMATION: synthetic sequence

<400> SEQUENCE: 25

Gly Phe Ser Phe Ser Ser Tyr Asp Met Gly Trp Val
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic sequence

<400> SEQUENCE: 26

Val Ala Ser Ile Tyr Ser Ser Ala Ser Ser Thr Tyr Tyr Ala
1               5                   10

<210> SEQ ID NO 27
<211> LENGTH: 22
<212> TYPE: PRT
<213> ORGANISM: Artificial Sequence
<220> FEATURE:
<223> OTHER INFORMATION: synthetic sequence

<400> SEQUENCE: 27

Cys Ala Lys Ala Ala Gly Arg Thr Tyr Arg Gly Trp Ala Thr Tyr Ile
1               5                   10                  15

Ala Asp Ser Ile Asp Ala
            20

<210> SEQ ID NO 28
<211> LENGTH: 9
<212> TYPE: PRT
<213> ORGANISM: Artificial Sequence
<220> FEATURE:
<223> OTHER INFORMATION: synthetic sequence

<400> SEQUENCE: 28

Cys Ser Gly Gly Ser Ser Gly Tyr Gly
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic sequence

<400> SEQUENCE: 29

Ile Tyr Ser Asn Asp Lys Arg Pro
1               5

<210> SEQ ID NO 30
<211> LENGTH: 12
<212> TYPE: PRT
<213> ORGANISM: Artificial Sequence
<220> FEATURE:
<223> OTHER INFORMATION: synthetic sequence

<400> SEQUENCE: 30

Cys Gly Ser Thr Asp Asn Ser Tyr Val Gly Ile Phe
1               5                   10
```

```
<210> SEQ ID NO 31
<211> LENGTH: 12
<212> TYPE: PRT
<213> ORGANISM: Artificial Sequence
<220> FEATURE:
<223> OTHER INFORMATION: synthetic sequence

<400> SEQUENCE: 31

Gly Phe Asp Phe Ser Ser Tyr Ala Met Asn Trp Val
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic sequence

<400> SEQUENCE: 32

Val Ala Gly Ile Gly Ser Thr Gly Ser Ser Thr Gly Tyr Gly
1               5                   10

<210> SEQ ID NO 33
<211> LENGTH: 21
<212> TYPE: PRT
<213> ORGANISM: Artificial Sequence
<220> FEATURE:
<223> OTHER INFORMATION: synthetic sequence

<400> SEQUENCE: 33

Cys Ala Lys Ser Val Gly Asn Gly Asn Ser Trp Ser Gly Tyr Ile Ala
1               5                   10                  15

Thr Ser Ile Asp Ala
            20

<210> SEQ ID NO 34
<211> LENGTH: 14
<212> TYPE: PRT
<213> ORGANISM: Artificial Sequence
<220> FEATURE:
<223> OTHER INFORMATION: synthetic sequence

<400> SEQUENCE: 34

Cys Ser Gly Asp Ser Ser Asp Asp Gly Ser Tyr Tyr Tyr Gly
1               5                   10

<210> SEQ ID NO 35

<400> SEQUENCE: 35

000

<210> SEQ ID NO 36
<211> LENGTH: 11
<212> TYPE: PRT
<213> ORGANISM: Artificial Sequence
<220> FEATURE:
<223> OTHER INFORMATION: synthetic sequence

<400> SEQUENCE: 36

Cys Gly Ser Tyr Asp Ser Ser Thr Gly Ile Phe
1               5                   10

<210> SEQ ID NO 37
<211> LENGTH: 12
<212> TYPE: PRT
<213> ORGANISM: Artificial Sequence
```

```
<220> FEATURE:
<223> OTHER INFORMATION: synthetic sequence

<400> SEQUENCE: 37

Gly Phe Ser Ile Ser Ser Tyr Thr Met Gln Trp Val
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic sequence

<400> SEQUENCE: 38

Val Ala Gly Ile Tyr Ser Gly Ser Arg Thr Tyr Tyr Gly
1               5                   10

<210> SEQ ID NO 39
<211> LENGTH: 23
<212> TYPE: PRT
<213> ORGANISM: Artificial Sequence
<220> FEATURE:
<223> OTHER INFORMATION: synthetic sequence

<400> SEQUENCE: 39

Cys Ala Lys Ser Ser Tyr Cys Thr Ala Trp Thr Gly Cys Asp Val Tyr
1               5                   10                  15

Ala Gly Gly Ser Ile Asp Ala
            20

<210> SEQ ID NO 40
<211> LENGTH: 9
<212> TYPE: PRT
<213> ORGANISM: Artificial Sequence
<220> FEATURE:
<223> OTHER INFORMATION: synthetic sequence

<400> SEQUENCE: 40

Cys Ser Gly Gly Asn Asn Tyr Tyr Gly
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic sequence

<400> SEQUENCE: 41

Ile Tyr Tyr Asn Asp Lys Arg Pro
1               5

<210> SEQ ID NO 42
<211> LENGTH: 11
<212> TYPE: PRT
<213> ORGANISM: Artificial Sequence
<220> FEATURE:
<223> OTHER INFORMATION: synthetic sequence

<400> SEQUENCE: 42

Cys Gly Gly Trp Asp Ser Ser Gly Gly Ile Phe
1               5                   10

<210> SEQ ID NO 43
<211> LENGTH: 12
```

```
<212> TYPE: PRT
<213> ORGANISM: Artificial Sequence
<220> FEATURE:
<223> OTHER INFORMATION: synthetic sequence

<400> SEQUENCE: 43

Gly Phe Thr Phe Ser Ser Tyr Ser Met Phe Trp Val
1               5                   10

<210> SEQ ID NO 44
<211> LENGTH: 13
<212> TYPE: PRT
<213> ORGANISM: Artificial Sequence
<220> FEATURE:
<223> OTHER INFORMATION: synthetic sequence

<400> SEQUENCE: 44

Val Ala Gly Ile Asp Ser Gly Ser Thr Thr Phe Tyr Gly
1               5                   10

<210> SEQ ID NO 45
<211> LENGTH: 21
<212> TYPE: PRT
<213> ORGANISM: Artificial Sequence
<220> FEATURE:
<223> OTHER INFORMATION: synthetic sequence

<400> SEQUENCE: 45

Cys Ala Lys Asp Ala Tyr Gly Tyr Cys Gly Trp Ser Gly Cys Ser Ala
1               5                   10                  15

Asp Ser Ile Asp Ala
            20

<210> SEQ ID NO 46
<211> LENGTH: 14
<212> TYPE: PRT
<213> ORGANISM: Artificial Sequence
<220> FEATURE:
<223> OTHER INFORMATION: synthetic sequence

<400> SEQUENCE: 46

Val Ala Gly Ile Gly Ser Thr Gly Ser Ser Thr Gly Tyr Ala
1               5                   10

<210> SEQ ID NO 47
<211> LENGTH: 11
<212> TYPE: PRT
<213> ORGANISM: Artificial Sequence
<220> FEATURE:
<223> OTHER INFORMATION: synthetic sequence

<400> SEQUENCE: 47

Cys Ser Gly Asp Asp Gly Ser Tyr Tyr Tyr Gly
1               5                   10

<210> SEQ ID NO 48
<211> LENGTH: 13
<212> TYPE: PRT
<213> ORGANISM: Artificial Sequence
<220> FEATURE:
<223> OTHER INFORMATION: synthetic sequence

<400> SEQUENCE: 48

Val Ala Gly Ile Tyr Ser Gly Ser Arg Thr Tyr Tyr Ala
1               5                   10
```

```
<210> SEQ ID NO 49
<211> LENGTH: 13
<212> TYPE: PRT
<213> ORGANISM: Artificial Sequence
<220> FEATURE:
<223> OTHER INFORMATION: synthetic sequence

<400> SEQUENCE: 49

Val Ala Gly Ile Asp Ser Gly Ser Thr Thr Phe Tyr Ala
1               5                   10

<210> SEQ ID NO 50
<211> LENGTH: 9
<212> TYPE: PRT
<213> ORGANISM: Artificial Sequence
<220> FEATURE:
<223> OTHER INFORMATION: synthetic sequence

<400> SEQUENCE: 50

Cys Ser Gly Gly Ser Gly Ser Tyr Gly
1               5

<210> SEQ ID NO 51
<211> LENGTH: 8
<212> TYPE: PRT
<213> ORGANISM: Artificial Sequence
<220> FEATURE:
<223> OTHER INFORMATION: synthetic sequence

<400> SEQUENCE: 51

Ile Tyr Gly Thr Asn Lys Arg Pro
1               5

<210> SEQ ID NO 52
<211> LENGTH: 13
<212> TYPE: PRT
<213> ORGANISM: Artificial Sequence
<220> FEATURE:
<223> OTHER INFORMATION: synthetic sequence

<400> SEQUENCE: 52

Cys Gly Ser Ala Asp Ser Ser Thr Asn Ala Gly Ile Phe
1               5                   10

<210> SEQ ID NO 53
<211> LENGTH: 12
<212> TYPE: PRT
<213> ORGANISM: Artificial Sequence
<220> FEATURE:
<223> OTHER INFORMATION: synthetic sequence

<400> SEQUENCE: 53

Gly Phe Thr Phe Ser Ser Tyr Ala Met Ser Trp Val
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic sequence

<400> SEQUENCE: 54

Val Ala Gly Ile Ser Ser Ser Gly Arg Tyr Thr Gly Tyr Ala
1               5                   10

<210> SEQ ID NO 55
```

```
<211> LENGTH: 12
<212> TYPE: PRT
<213> ORGANISM: Artificial Sequence
<220> FEATURE:
<223> OTHER INFORMATION: synthetic sequence

<400> SEQUENCE: 55

Gly Phe Thr Phe Ser Ser Tyr Ala Met Asn Trp Val
1               5                   10

<210> SEQ ID NO 56
<211> LENGTH: 5
<212> TYPE: PRT
<213> ORGANISM: Artificial Sequence
<220> FEATURE:
<223> OTHER INFORMATION: synthetic sequence

<400> SEQUENCE: 56

Ser Tyr Ala Met Ser
1               5

<210> SEQ ID NO 57
<211> LENGTH: 18
<212> TYPE: PRT
<213> ORGANISM: Artificial Sequence
<220> FEATURE:
<223> OTHER INFORMATION: synthetic sequence

<400> SEQUENCE: 57

Ser Val Gly Asn Gly Asn Ser Trp Ser Gly Tyr Ile Ala Thr Ser Ile
1               5                   10                  15

Asp Ala

<210> SEQ ID NO 58
<211> LENGTH: 8
<212> TYPE: PRT
<213> ORGANISM: Artificial Sequence
<220> FEATURE:
<223> OTHER INFORMATION: synthetic sequence

<400> SEQUENCE: 58

Ser Gly Gly Ser Gly Ser Tyr Gly
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic sequence

<400> SEQUENCE: 59

Gly Thr Asn Lys Arg Pro Ser
1               5

<210> SEQ ID NO 60
<211> LENGTH: 11
<212> TYPE: PRT
<213> ORGANISM: Artificial Sequence
<220> FEATURE:
<223> OTHER INFORMATION: synthetic sequence

<400> SEQUENCE: 60

Gly Ser Ala Asp Ser Ser Thr Asn Ala Gly Ile
1               5                   10
```

<210> SEQ ID NO 61
<211> LENGTH: 18
<212> TYPE: PRT
<213> ORGANISM: Artificial Sequence
<220> FEATURE:
<223> OTHER INFORMATION: synthetic sequence

<400> SEQUENCE: 61

```
Ser Val Gly Asn Gly Asn Ser Trp Ser Gly Tyr Val Ala Thr Ser Ile
1               5                   10                  15

Asp Ala
```

<210> SEQ ID NO 62
<211> LENGTH: 5
<212> TYPE: PRT
<213> ORGANISM: Artificial Sequence
<220> FEATURE:
<223> OTHER INFORMATION: synthetic sequence

<400> SEQUENCE: 62

```
Ser Tyr Ala Met Asn
1               5
```

<210> SEQ ID NO 63
<211> LENGTH: 18
<212> TYPE: PRT
<213> ORGANISM: Artificial Sequence
<220> FEATURE:
<223> OTHER INFORMATION: synthetic sequence

<400> SEQUENCE: 63

```
Ser Val Gly Ser Gly Val Ser Trp Ser Gly Tyr Val Ala Thr Ser Ile
1               5                   10                  15

Asp Ala
```

<210> SEQ ID NO 64
<211> LENGTH: 8
<212> TYPE: PRT
<213> ORGANISM: Artificial Sequence
<220> FEATURE:
<223> OTHER INFORMATION: synthetic sequence

<400> SEQUENCE: 64

```
Ser Ala Gly Ser Gly Leu Tyr Gly
1               5
```

<210> SEQ ID NO 65
<211> LENGTH: 18
<212> TYPE: PRT
<213> ORGANISM: Artificial Sequence
<220> FEATURE:
<223> OTHER INFORMATION: synthetic sequence

<400> SEQUENCE: 65

```
Ser Met Gly Ser Gly Val Ser Trp Ser Gly Tyr Val Ala Thr Ser Ile
1               5                   10                  15

Asp Ala
```

<210> SEQ ID NO 66
<211> LENGTH: 18
<212> TYPE: PRT
<213> ORGANISM: Artificial Sequence
<220> FEATURE:
<223> OTHER INFORMATION: synthetic sequence

<400> SEQUENCE: 66

```
Ser Met Gly Ser Gly Val Ser Trp Ser Gly Tyr Val Ala Thr Ser Ile
1               5                   10                  15

Asp Val

<210> SEQ ID NO 67
<211> LENGTH: 18
<212> TYPE: PRT
<213> ORGANISM: Artificial Sequence
<220> FEATURE:
<223> OTHER INFORMATION: synthetic sequence

<400> SEQUENCE: 67

Ser Val Gly Ser Gly Val Ser Trp Ser Gly Tyr Val Ala Thr Ser Leu
1               5                   10                  15

Asp Ala

<210> SEQ ID NO 68
<211> LENGTH: 7
<212> TYPE: PRT
<213> ORGANISM: Artificial Sequence
<220> FEATURE:
<223> OTHER INFORMATION: synthetic sequence

<400> SEQUENCE: 68

Gly Thr Tyr Lys Arg Pro Ser
1               5

<210> SEQ ID NO 69
<211> LENGTH: 18
<212> TYPE: PRT
<213> ORGANISM: Artificial Sequence
<220> FEATURE:
<223> OTHER INFORMATION: synthetic sequence

<400> SEQUENCE: 69

Ser Val Gly Ser Gly Val Ser Trp Ser Gly Tyr Val Ala Thr Ser Leu
1               5                   10                  15

Asp Val

<210> SEQ ID NO 70
<211> LENGTH: 11
<212> TYPE: PRT
<213> ORGANISM: Artificial Sequence
<220> FEATURE:
<223> OTHER INFORMATION: synthetic sequence

<400> SEQUENCE: 70

Gly Ser Asn Asp Ala Ser Thr Asn Ala Gly Ile
1               5                   10

<210> SEQ ID NO 71
<211> LENGTH: 5
<212> TYPE: PRT
<213> ORGANISM: Artificial Sequence
<220> FEATURE:
<223> OTHER INFORMATION: synthetic sequence

<400> SEQUENCE: 71

Ser Tyr Gly Met Ser
1               5

<210> SEQ ID NO 72
<211> LENGTH: 17
<212> TYPE: PRT
```

<213> ORGANISM: Artificial Sequence
<220> FEATURE:
<223> OTHER INFORMATION: synthetic sequence

<400> SEQUENCE: 72

Gly Ile Gly Ser Ser Gly Ile Tyr Thr His Tyr Ala Asp Ser Val Lys
1               5                   10                  15

Gly

<210> SEQ ID NO 73
<211> LENGTH: 26
<212> TYPE: PRT
<213> ORGANISM: Artificial Sequence
<220> FEATURE:
<223> OTHER INFORMATION: synthetic sequence

<400> SEQUENCE: 73

Ser Pro Gly Asp Ser Asp Trp Cys Gly Trp Ala Gly Tyr Gly Ile Tyr
1               5                   10                  15

Ser Cys Arg Val Ala Gly Phe Ile Asp Ala
            20                  25

<210> SEQ ID NO 74
<211> LENGTH: 9
<212> TYPE: PRT
<213> ORGANISM: Artificial Sequence
<220> FEATURE:
<223> OTHER INFORMATION: synthetic sequence

<400> SEQUENCE: 74

Ser Gly Gly Tyr Asn Gly His Tyr Gly
1               5

<210> SEQ ID NO 75
<211> LENGTH: 9
<212> TYPE: PRT
<213> ORGANISM: Artificial Sequence
<220> FEATURE:
<223> OTHER INFORMATION: synthetic sequence

<400> SEQUENCE: 75

Gly Gly Tyr Asp Ser Ser Ala Gly Ile
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic sequence

<400> SEQUENCE: 76

Gly Tyr Ala Met Ser
1               5

<210> SEQ ID NO 77
<211> LENGTH: 17
<212> TYPE: PRT
<213> ORGANISM: Artificial Sequence
<220> FEATURE:
<223> OTHER INFORMATION: synthetic sequence

<400> SEQUENCE: 77

Gly Ile Tyr Ser Ser Gly Ser Tyr Thr Phe Tyr Ala Asp Ser Val Lys
1               5                   10                  15

Gly

<210> SEQ ID NO 78
<211> LENGTH: 20
<212> TYPE: PRT
<213> ORGANISM: Artificial Sequence
<220> FEATURE:
<223> OTHER INFORMATION: synthetic sequence

<400> SEQUENCE: 78

```
Gly Thr Gly Tyr Cys Asp Trp Ser Gly Trp Cys Tyr Ser Gly Ala Ala
1               5                   10                  15

Asn Ile Asp Ala
            20
```

<210> SEQ ID NO 79
<211> LENGTH: 11
<212> TYPE: PRT
<213> ORGANISM: Artificial Sequence
<220> FEATURE:
<223> OTHER INFORMATION: synthetic sequence

<400> SEQUENCE: 79

```
Gly Ser Glu Asp Ser Ser Ser Gly Ala Gly Ile
1               5                   10
```

<210> SEQ ID NO 80
<211> LENGTH: 5
<212> TYPE: PRT
<213> ORGANISM: Artificial Sequence
<220> FEATURE:
<223> OTHER INFORMATION: synthetic sequence

<400> SEQUENCE: 80

```
Ser Tyr Asp Met Gly
1               5
```

<210> SEQ ID NO 81
<211> LENGTH: 17
<212> TYPE: PRT
<213> ORGANISM: Artificial Sequence
<220> FEATURE:
<223> OTHER INFORMATION: synthetic sequence

<400> SEQUENCE: 81

```
Ser Ile Tyr Ser Ser Ala Ser Ser Thr Tyr Tyr Ala Pro Ala Val Lys
1               5                   10                  15

Gly
```

<210> SEQ ID NO 82
<211> LENGTH: 19
<212> TYPE: PRT
<213> ORGANISM: Artificial Sequence
<220> FEATURE:
<223> OTHER INFORMATION: synthetic sequence

<400> SEQUENCE: 82

```
Ala Ala Gly Arg Thr Tyr Arg Gly Trp Ala Thr Tyr Ile Ala Asp Ser
1               5                   10                  15

Ile Asp Ala
```

<210> SEQ ID NO 83
<211> LENGTH: 10
<212> TYPE: PRT
<213> ORGANISM: Artificial Sequence

```
<220> FEATURE:
<223> OTHER INFORMATION: synthetic sequence

<400> SEQUENCE: 83

Ser Gly Asp Ser Ser Trp Tyr Gly Tyr Gly
1               5                   10

<210> SEQ ID NO 84
<211> LENGTH: 7
<212> TYPE: PRT
<213> ORGANISM: Artificial Sequence
<220> FEATURE:
<223> OTHER INFORMATION: synthetic sequence

<400> SEQUENCE: 84

Glu Ser Gly Lys Arg Pro Ser
1               5

<210> SEQ ID NO 85
<211> LENGTH: 10
<212> TYPE: PRT
<213> ORGANISM: Artificial Sequence
<220> FEATURE:
<223> OTHER INFORMATION: synthetic sequence

<400> SEQUENCE: 85

Gly Ser Ala Asp Ser Asn Ser Ile Gly Ile
1               5                   10

<210> SEQ ID NO 86
<211> LENGTH: 17
<212> TYPE: PRT
<213> ORGANISM: Artificial Sequence
<220> FEATURE:
<223> OTHER INFORMATION: synthetic sequence

<400> SEQUENCE: 86

Gly Ile Gly Ser Thr Gly Ser Ser Thr Gly Tyr Gly Pro Ala Val Lys
1               5                   10                  15

Gly

<210> SEQ ID NO 87
<211> LENGTH: 8
<212> TYPE: PRT
<213> ORGANISM: Artificial Sequence
<220> FEATURE:
<223> OTHER INFORMATION: synthetic sequence

<400> SEQUENCE: 87

Ser Gly Gly Ser Ser Gly Tyr Gly
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic sequence

<400> SEQUENCE: 88

Ser Asn Asp Lys Arg Pro Ser
1               5

<210> SEQ ID NO 89
<211> LENGTH: 10
<212> TYPE: PRT
```

```
<213> ORGANISM: Artificial Sequence
<220> FEATURE:
<223> OTHER INFORMATION: synthetic sequence

<400> SEQUENCE: 89

Gly Ser Thr Asp Asn Ser Tyr Val Gly Ile
1               5                   10

<210> SEQ ID NO 90
<211> LENGTH: 5
<212> TYPE: PRT
<213> ORGANISM: Artificial Sequence
<220> FEATURE:
<223> OTHER INFORMATION: synthetic sequence

<400> SEQUENCE: 90

Ser Tyr Thr Met Gln
1               5

<210> SEQ ID NO 91
<211> LENGTH: 16
<212> TYPE: PRT
<213> ORGANISM: Artificial Sequence
<220> FEATURE:
<223> OTHER INFORMATION: synthetic sequence

<400> SEQUENCE: 91

Gly Ile Tyr Ser Gly Ser Arg Thr Tyr Tyr Gly Ala Ala Val Gln Gly
1               5                   10                  15

<210> SEQ ID NO 92
<211> LENGTH: 20
<212> TYPE: PRT
<213> ORGANISM: Artificial Sequence
<220> FEATURE:
<223> OTHER INFORMATION: synthetic sequence

<400> SEQUENCE: 92

Ser Ser Tyr Cys Thr Ala Trp Thr Gly Cys Asp Val Tyr Ala Gly Gly
1               5                   10                  15

Ser Ile Asp Ala
            20

<210> SEQ ID NO 93
<211> LENGTH: 13
<212> TYPE: PRT
<213> ORGANISM: Artificial Sequence
<220> FEATURE:
<223> OTHER INFORMATION: synthetic sequence

<400> SEQUENCE: 93

Ser Gly Asp Ser Ser Asp Asp Gly Ser Tyr Tyr Tyr Gly
1               5                   10

<210> SEQ ID NO 94
<211> LENGTH: 9
<212> TYPE: PRT
<213> ORGANISM: Artificial Sequence
<220> FEATURE:
<223> OTHER INFORMATION: synthetic sequence

<400> SEQUENCE: 94

Gly Ser Tyr Asp Ser Ser Thr Gly Ile
1               5

<210> SEQ ID NO 95
```

```
<211> LENGTH: 5
<212> TYPE: PRT
<213> ORGANISM: Artificial Sequence
<220> FEATURE:
<223> OTHER INFORMATION: synthetic sequence

<400> SEQUENCE: 95

Ser Tyr Ser Met Phe
1               5

<210> SEQ ID NO 96
<211> LENGTH: 16
<212> TYPE: PRT
<213> ORGANISM: Artificial Sequence
<220> FEATURE:
<223> OTHER INFORMATION: synthetic sequence

<400> SEQUENCE: 96

Gly Ile Asp Ser Gly Ser Thr Thr Phe Tyr Gly Ser Ala Val Lys Gly
1               5                   10                  15

<210> SEQ ID NO 97
<211> LENGTH: 18
<212> TYPE: PRT
<213> ORGANISM: Artificial Sequence
<220> FEATURE:
<223> OTHER INFORMATION: synthetic sequence

<400> SEQUENCE: 97

Asp Ala Tyr Gly Tyr Cys Gly Trp Ser Gly Cys Ser Ala Asp Ser Ile
1               5                   10                  15

Asp Ala

<210> SEQ ID NO 98
<211> LENGTH: 8
<212> TYPE: PRT
<213> ORGANISM: Artificial Sequence
<220> FEATURE:
<223> OTHER INFORMATION: synthetic sequence

<400> SEQUENCE: 98

Ser Gly Gly Asn Asn Tyr Tyr Gly
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic sequence

<400> SEQUENCE: 99

Tyr Asn Asp Lys Arg Pro Ser
1               5

<210> SEQ ID NO 100
<211> LENGTH: 9
<212> TYPE: PRT
<213> ORGANISM: Artificial Sequence
<220> FEATURE:
<223> OTHER INFORMATION: synthetic sequence

<400> SEQUENCE: 100

Gly Gly Trp Asp Ser Ser Gly Gly Ile
1               5
```

```
<210> SEQ ID NO 101
<211> LENGTH: 17
<212> TYPE: PRT
<213> ORGANISM: Artificial Sequence
<220> FEATURE:
<223> OTHER INFORMATION: synthetic sequence

<400> SEQUENCE: 101

Gly Ile Ser Ser Ser Gly Arg Tyr Thr Gly Tyr Ala Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: synthetic sequence

<400> SEQUENCE: 102

Gly Ile Gly Ser Thr Gly Ser Ser Thr Gly Tyr Ala Asp Ser Val Lys
1               5                   10                  15

Gly

<210> SEQ ID NO 103
<211> LENGTH: 127
<212> TYPE: PRT
<213> ORGANISM: Artificial Sequence
<220> FEATURE:
<223> OTHER INFORMATION: synthetic sequence

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Gly Asn Gly Asn Ser Trp Ser Gly Tyr Val Ala Thr
            100                 105                 110

Ser Ile Asp Ala Trp Gly Gln Gly Thr Leu Val Thr Val Ser Ser
        115                 120                 125

<210> SEQ ID NO 104
<211> LENGTH: 105
<212> TYPE: PRT
<213> ORGANISM: Artificial Sequence
<220> FEATURE:
<223> OTHER INFORMATION: synthetic sequence

<400> SEQUENCE: 104

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Trp Tyr
            20                  25                  30
```

Gln Gln Lys Pro Gly Gln Ala Pro Val Leu Val Ile Tyr Gly Thr Asn
        35                  40                  45

Lys Arg Pro Ser Gly Ile Pro Glu Arg Phe Ser Gly Ser Ser Ser Gly
 50                  55                  60

Thr Thr Val Thr Leu Thr Ile Ser Gly Val Gln Ala Glu Asp Glu Ala
 65                  70                  75                  80

Asp Tyr Tyr Cys Gly Ser Ala Asp Ser Ser Thr Asn Ala Gly Ile Phe
                 85                  90                  95

Gly Gly Gly Thr Lys Leu Thr Val Leu
            100                 105

<210> SEQ ID NO 105
<211> LENGTH: 127
<212> TYPE: PRT
<213> ORGANISM: Artificial Sequence
<220> FEATURE:
<223> OTHER INFORMATION: synthetic sequence

<400> SEQUENCE: 105

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Val Gly Ser Gly Val Ser Trp Ser Gly Tyr Val Ala Thr
            100                 105                 110

Ser Ile Asp Ala Trp Gly Gln Gly Thr Leu Val Thr Val Ser Ser
        115                 120                 125

<210> SEQ ID NO 106
<211> LENGTH: 105
<212> TYPE: PRT
<213> ORGANISM: Artificial Sequence
<220> FEATURE:
<223> OTHER INFORMATION: synthetic sequence

<400> SEQUENCE: 106

Ser Tyr Glu Leu Thr Gln Pro Pro Ser Val Ser Val Ser Pro Gly Gln
 1               5                  10                  15

Thr Ala Arg Ile Thr Cys Ser Ala Gly Ser Gly Leu Tyr Gly Trp Tyr
            20                  25                  30

Gln Gln Lys Pro Gly Gln Ala Pro Val Leu Val Ile Tyr Gly Thr Asn
        35                  40                  45

Lys Arg Pro Ser Gly Ile Pro Glu Arg Phe Ser Gly Ser Ser Ser Gly
 50                  55                  60

Thr Thr Val Thr Leu Thr Ile Ser Gly Val Gln Ala Glu Asp Glu Ala
 65                  70                  75                  80

Asp Tyr Tyr Cys Gly Ser Ala Asp Ser Ser Thr Asn Ala Gly Ile Phe
                 85                  90                  95

Gly Gly Gly Thr Lys Leu Thr Val Leu
            100                 105

<210> SEQ ID NO 107
<211> LENGTH: 127
<212> TYPE: PRT
<213> ORGANISM: Artificial Sequence
<220> FEATURE:
<223> OTHER INFORMATION: synthetic sequence

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Met Gly Ser Gly Val Ser Trp Ser Gly Tyr Val Ala Thr
            100                 105                 110

Ser Ile Asp Ala Trp Gly Gln Gly Thr Leu Val Thr Val Ser Ser
        115                 120                 125

<210> SEQ ID NO 108
<211> LENGTH: 105
<212> TYPE: PRT
<213> ORGANISM: Artificial Sequence
<220> FEATURE:
<223> OTHER INFORMATION: synthetic sequence

<400> SEQUENCE: 108

Ser Tyr Glu Leu Thr Gln Pro Pro Ser Val Ser Val Ser Pro Gly Gln
1               5                   10                  15

Thr Ala Arg Ile Thr Cys Ser Ala Gly Ser Gly Leu Tyr Gly Trp Tyr
            20                  25                  30

Gln Gln Lys Pro Gly Gln Ala Pro Val Leu Val Ile Tyr Gly Thr Asn
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105

<210> SEQ ID NO 109
<211> LENGTH: 127
<212> TYPE: PRT
<213> ORGANISM: Artificial Sequence
<220> FEATURE:
<223> OTHER INFORMATION: synthetic sequence

<400> SEQUENCE: 109

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Met Gly Ser Gly Val Ser Trp Ser Gly Tyr Val Ala Thr
            100                 105                 110

Ser Ile Asp Val Trp Gly Gln Gly Thr Leu Val Thr Val Ser Ser
        115                 120                 125

<210> SEQ ID NO 110
<211> LENGTH: 105
<212> TYPE: PRT
<213> ORGANISM: Artificial Sequence
<220> FEATURE:
<223> OTHER INFORMATION: synthetic sequence

<400> SEQUENCE: 110

Ser Tyr Glu Leu Thr Gln Pro Pro Ser Val Ser Val Ser Pro Gly Gln
1               5                   10                  15

Thr Ala Arg Ile Thr Cys Ser Ala Gly Ser Gly Leu Tyr Gly Trp Tyr
            20                  25                  30

Gln Gln Lys Pro Gly Gln Ala Pro Val Leu Val Ile Tyr Gly Thr Asn
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105

<210> SEQ ID NO 111
<211> LENGTH: 127
<212> TYPE: PRT
<213> ORGANISM: Artificial Sequence
<220> FEATURE:
<223> OTHER INFORMATION: synthetic sequence

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Val Gly Ser Gly Val Ser Trp Ser Gly Tyr Val Ala Thr
            100                 105                 110

Ser Leu Asp Ala Trp Gly Gln Gly Thr Leu Val Thr Val Ser Ser
            115                 120                 125
```

<210> SEQ ID NO 112
<211> LENGTH: 105
<212> TYPE: PRT
<213> ORGANISM: Artificial Sequence
<220> FEATURE:
<223> OTHER INFORMATION: synthetic sequence

<400> SEQUENCE: 112

```
Ser Tyr Glu Leu Thr Gln Pro Pro Ser Val Ser Val Ser Pro Gly Gln
1               5                   10                  15

Thr Ala Arg Ile Thr Cys Ser Ala Gly Ser Gly Leu Tyr Gly Trp Tyr
            20                  25                  30

Gln Gln Lys Pro Gly Gln Ala Pro Val Leu Val Ile Tyr Gly Thr Asn
            35                  40                  45

Lys Arg Pro Ser Gly Ile Pro Glu Arg Phe Ser Gly Ser Ser Ser Gly
50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105
```

<210> SEQ ID NO 113
<211> LENGTH: 127
<212> TYPE: PRT
<213> ORGANISM: Artificial Sequence
<220> FEATURE:
<223> OTHER INFORMATION: synthetic sequence

<400> SEQUENCE: 113

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ala Gly Ile Ser Ser Ser Gly Arg Tyr Thr Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Met Gly Ser Gly Val Ser Trp Ser Gly Tyr Val Ala Thr
            100                 105                 110

Ser Ile Asp Ala Trp Gly Gln Gly Thr Leu Val Thr Val Ser Ser
            115                 120                 125
```

<210> SEQ ID NO 114
<211> LENGTH: 105
<212> TYPE: PRT
<213> ORGANISM: Artificial Sequence
<220> FEATURE:
<223> OTHER INFORMATION: synthetic sequence

<400> SEQUENCE: 114

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Trp Tyr
            20                  25                  30

Gln Gln Lys Pro Gly Gln Ala Pro Val Leu Val Ile Tyr Gly Thr Tyr
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100                 105

<210> SEQ ID NO 115
<211> LENGTH: 127
<212> TYPE: PRT
<213> ORGANISM: Artificial Sequence
<220> FEATURE:
<223> OTHER INFORMATION: synthetic sequence

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Met Gly Ser Gly Val Ser Trp Ser Gly Tyr Val Ala Thr
            100                 105                 110

Ser Leu Asp Val Trp Gly Gln Gly Thr Leu Val Thr Val Ser Ser
        115                 120                 125

<210> SEQ ID NO 116
<211> LENGTH: 105
<212> TYPE: PRT
<213> ORGANISM: Artificial Sequence
<220> FEATURE:
<223> OTHER INFORMATION: synthetic sequence

<400> SEQUENCE: 116

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Trp Tyr
            20                  25                  30

Gln Gln Lys Pro Gly Gln Ala Pro Val Leu Val Ile Tyr Gly Thr Tyr
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100             105

<210> SEQ ID NO 117
<211> LENGTH: 127
<212> TYPE: PRT
<213> ORGANISM: Artificial Sequence
<220> FEATURE:
<223> OTHER INFORMATION: synthetic sequence

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Gly Ser Gly Val Ser Trp Ser Gly Tyr Val Ala Thr
            100                 105                 110

Ser Leu Asp Val Trp Gly Gln Gly Thr Leu Val Thr Val Ser Ser
        115                 120                 125

<210> SEQ ID NO 118
<211> LENGTH: 105
<212> TYPE: PRT
<213> ORGANISM: Artificial Sequence
<220> FEATURE:
<223> OTHER INFORMATION: synthetic sequence

<400> SEQUENCE: 118

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Trp Tyr
            20                  25                  30

Gln Gln Lys Pro Gly Gln Ala Pro Val Leu Val Ile Tyr Gly Thr Tyr
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Ala Asp Ser Ser Thr Asn Ala Gly Ile Phe
                85                  90                  95

Gly Gly Gly Thr Lys Leu Thr Val Leu
            100             105

<210> SEQ ID NO 119
<211> LENGTH: 127
<212> TYPE: PRT

```
<213> ORGANISM: Artificial Sequence
<220> FEATURE:
<223> OTHER INFORMATION: synthetic sequence

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Gly Ile Ser Ser Ser Gly Arg Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Gly Ser Gly Val Ser Trp Ser Gly Tyr Val Ala Thr
            100                 105                 110

Ser Leu Asp Val Trp Gly Gln Gly Thr Leu Val Thr Val Ser Ser
        115                 120                 125

<210> SEQ ID NO 120
<211> LENGTH: 105
<212> TYPE: PRT
<213> ORGANISM: Artificial Sequence
<220> FEATURE:
<223> OTHER INFORMATION: synthetic sequence

<400> SEQUENCE: 120

Ser Tyr Glu Leu Thr Gln Pro Pro Ser Val Ser Val Ser Pro Gly Gln
1               5                   10                  15

Thr Ala Arg Ile Thr Cys Ser Ala Gly Ser Gly Leu Tyr Gly Trp Tyr
            20                  25                  30

Gln Gln Lys Pro Gly Gln Ala Pro Val Leu Val Ile Tyr Gly Thr Asn
        35                  40                  45

Lys Arg Pro Ser Gly Ile Pro Glu Arg Phe Ser Gly Ser Ser Ser Gly
    50                  55                  60

Thr Thr Val Thr Leu Thr Ile Ser Gly Val Gln Ala Glu Asp Glu Ala
65                  70                  75                  80

Asp Tyr Tyr Cys Gly Ser Asn Asp Ala Ser Thr Asn Ala Gly Ile Phe
                85                  90                  95

Gly Gly Gly Thr Lys Leu Thr Val Leu
            100                 105

<210> SEQ ID NO 121
<211> LENGTH: 135
<212> TYPE: PRT
<213> ORGANISM: Artificial Sequence
<220> FEATURE:
<223> OTHER INFORMATION: synthetic sequence

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45
```

Ala Gly Ile Gly Ser Ser Gly Ile Tyr Thr His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Gly Asp Ser Asp Trp Cys Gly Trp Ala Gly Tyr Gly
            100                 105                 110

Ile Tyr Ser Cys Arg Val Ala Gly Phe Ile Asp Ala Trp Gly Gln Gly
        115                 120                 125

Thr Leu Val Thr Val Ser Ser
        130                 135

<210> SEQ ID NO 122
<211> LENGTH: 104
<212> TYPE: PRT
<213> ORGANISM: Artificial Sequence
<220> FEATURE:
<223> OTHER INFORMATION: synthetic sequence

<400> SEQUENCE: 122

Ser Tyr Glu Leu Thr Gln Pro Pro Ser Val Ser Val Ser Pro Gly Gln
1               5                   10                  15

Thr Ala Arg Ile Thr Cys Ser Gly Gly Tyr Asn Gly His Tyr Gly Trp
            20                  25                  30

Tyr Gln Gln Lys Pro Gly Gln Ala Pro Val Leu Val Ile Tyr Gly Thr
        35                  40                  45

Asn Lys Arg Pro Ser Gly Ile Pro Glu Arg Phe Ser Gly Ser Ser Ser
    50                  55                  60

Gly Thr Thr Val Thr Leu Thr Ile Ser Gly Val Gln Ala Glu Asp Glu
65                  70                  75                  80

Ala Asp Tyr Tyr Cys Gly Gly Tyr Asp Ser Ser Ala Gly Ile Phe Gly
                85                  90                  95

Gly Gly Thr Lys Leu Thr Val Leu
            100

<210> SEQ ID NO 123
<211> LENGTH: 129
<212> TYPE: PRT
<213> ORGANISM: Artificial Sequence
<220> FEATURE:
<223> OTHER INFORMATION: synthetic sequence

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ala Gly Ile Tyr Ser Ser Gly Ser Tyr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Gly Tyr Cys Asp Trp Ser Gly Trp Cys Tyr Ser Gly

-continued

```
               100                 105                 110
Ala Ala Asn Ile Asp Ala Trp Gly Gln Gly Thr Leu Val Thr Val Ser
        115                 120                 125
Ser

<210> SEQ ID NO 124
<211> LENGTH: 108
<212> TYPE: PRT
<213> ORGANISM: Artificial Sequence
<220> FEATURE:
<223> OTHER INFORMATION: synthetic sequence

<400> SEQUENCE: 124

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
        35                  40                  45

Gly Thr Asn Lys Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Ser Glu Asp Ser Ser Ser Gly Ala
                85                  90                  95

Gly Ile Phe Gly Gly Gly Thr Lys Leu Thr Val Leu
            100                 105

<210> SEQ ID NO 125
<211> LENGTH: 17
<212> TYPE: PRT
<213> ORGANISM: Artificial Sequence
<220> FEATURE:
<223> OTHER INFORMATION: synthetic sequence

<400> SEQUENCE: 125

Gly Ile Ser Ser Ser Gly Arg Tyr Thr Gly Tyr Ala Asp Ser Val Lys
1               5                   10                  15

Gly

<210> SEQ ID NO 126
<211> LENGTH: 18
<212> TYPE: PRT
<213> ORGANISM: Artificial Sequence
<220> FEATURE:
<223> OTHER INFORMATION: synthetic sequence

<400> SEQUENCE: 126

Ser Met Gly Ser Gly Val Ser Trp Ser Gly Tyr Val Ala Thr Ser Leu
1               5                   10                  15

Asp Val

<210> SEQ ID NO 127
<211> LENGTH: 103
<212> TYPE: PRT
<213> ORGANISM: Artificial Sequence
<220> FEATURE:
<223> OTHER INFORMATION: synthetic sequence

<400> SEQUENCE: 127

Ala Leu Thr Gln Pro Ser Ser Val Ser Ala Asn Pro Gly Glu Thr Val
```

```
1               5                   10                  15
Lys Ile Thr Cys Ser Gly Gly Tyr Asn Gly His Tyr Gly Trp Tyr Gln
                20                  25                  30

Gln Lys Ser Pro Gly Ser Ala Pro Val Thr Val Ile Tyr Ser Asn Asn
            35                  40                  45

Gln Arg Pro Ser Asn Ile Pro Ser Arg Phe Ser Gly Ser Thr Ser Gly
        50                  55                  60

Ser Thr Ser Thr Leu Thr Ile Thr Gly Val Arg Ala Glu Asp Glu Ala
65                  70                  75                  80

Val Tyr Phe Cys Gly Gly Tyr Asp Ser Ser Ala Gly Ile Phe Gly Ala
                85                  90                  95

Gly Thr Thr Leu Thr Val Leu
                100

<210> SEQ ID NO 128
<211> LENGTH: 104
<212> TYPE: PRT
<213> ORGANISM: Artificial Sequence
<220> FEATURE:
<223> OTHER INFORMATION: synthetic sequence

<400> SEQUENCE: 128

Ser Tyr Glu Leu Thr Gln Pro Pro Ser Val Ser Val Ser Pro Gly Gln
1               5                   10                  15

Thr Ala Arg Ile Thr Cys Ser Gly Gly Tyr Asn Gly His Tyr Gly Trp
                20                  25                  30

Tyr Gln Gln Lys Pro Gly Gln Ala Pro Val Leu Val Ile Tyr Ser Asn
            35                  40                  45

Asn Gln Arg Pro Ser Gly Ile Pro Glu Arg Phe Ser Gly Ser Ser Ser
        50                  55                  60

Gly Thr Thr Val Thr Leu Thr Ile Ser Gly Val Gln Ala Glu Asp Glu
65                  70                  75                  80

Ala Asp Tyr Tyr Cys Gly Gly Tyr Asp Ser Ser Ala Gly Ile Phe Gly
                85                  90                  95

Gly Gly Thr Lys Leu Thr Val Leu
                100

<210> SEQ ID NO 129
<211> LENGTH: 106
<212> TYPE: PRT
<213> ORGANISM: Artificial Sequence
<220> FEATURE:
<223> OTHER INFORMATION: synthetic sequence

<400> SEQUENCE: 129

Ala Leu Thr Gln Pro Ser Ser Val Ser Ala Asn Pro Gly Glu Thr Val
1               5                   10                  15

Lys Ile Thr Cys Ser Gly Gly Gly Ser Ser Asn Tyr Tyr Gly Trp Tyr
                20                  25                  30

Gln Gln Lys Ser Pro Gly Ser Ala Pro Val Thr Leu Ile Tyr Gly Thr
            35                  40                  45

Asn Lys Arg Pro Ser Asp Ile Pro Ser Arg Phe Ser Gly Ser Lys Ser
        50                  55                  60

Gly Ser Thr Gly Thr Leu Thr Ile Thr Gly Val Gln Ala Asp Asp Glu
65                  70                  75                  80

Ala Val Tyr Phe Cys Gly Ser Ala Asp Ser Ser Thr Asn Ala Gly Ile
                85                  90                  95
```

```
Phe Gly Ala Gly Thr Thr Leu Thr Val Leu
            100                 105
```

<210> SEQ ID NO 130
<211> LENGTH: 110
<212> TYPE: PRT
<213> ORGANISM: Artificial Sequence
<220> FEATURE:
<223> OTHER INFORMATION: synthetic sequence

<400> SEQUENCE: 130

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Ser Asn Tyr Ala Gly
            20                  25                  30

Trp Tyr Gly Tyr Tyr Gln Gln Lys Pro Gly Gln Ala Pro Val Thr Val
        35                  40                  45

Ile Tyr Gly Thr Asn Lys Arg Pro Ser Gly Ile Pro Glu Arg Phe Ser
    50                  55                  60

Gly Ser Ser Ser Gly Thr Thr Val Thr Leu Thr Ile Ser Gly Val Gln
65                  70                  75                  80

Ala Glu Asp Glu Ala Val Tyr Tyr Cys Gly Ser Ala Asp Ser Ser Thr
                85                  90                  95

Asn Ala Gly Ile Phe Gly Ala Gly Thr Lys Leu Thr Val Leu
            100                 105                 110
```

<210> SEQ ID NO 131
<211> LENGTH: 107
<212> TYPE: PRT
<213> ORGANISM: Artificial Sequence
<220> FEATURE:
<223> OTHER INFORMATION: synthetic sequence

<400> SEQUENCE: 131

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
        35                  40                  45

Gly Thr Asn Lys Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Ser Thr Asp Ser Asn Tyr Val Gly
                85                  90                  95

Ile Phe Gly Gly Gly Thr Lys Leu Thr Val Leu
            100                 105
```

<210> SEQ ID NO 132
<211> LENGTH: 105
<212> TYPE: PRT
<213> ORGANISM: Artificial Sequence
<220> FEATURE:
<223> OTHER INFORMATION: synthetic sequence

<400> SEQUENCE: 132

```
Ser Tyr Glu Leu Thr Gln Pro Pro Ser Val Ser Val Ser Pro Gly Gln
1               5                   10                  15

Thr Ala Arg Ile Thr Cys Ser Gly Gly Tyr Asn Gly His Tyr Gly Trp
```

```
            20                  25                  30
Tyr Gln Gln Lys Pro Gly Gln Ala Pro Val Leu Val Ile Tyr Ser Asn
            35                  40                  45

Asn Gln Arg Pro Ser Gly Ile Pro Glu Arg Phe Ser Gly Ser Ser Ser
        50                  55                  60

Gly Thr Thr Val Thr Leu Thr Ile Ser Gly Val Gln Ala Glu Asp Glu
65                  70                  75                  80

Ala Asp Tyr Tyr Cys Gly Asn Ala Asp Ser Asn Tyr Val Gly Ile Phe
                85                  90                  95

Gly Gly Gly Thr Lys Leu Thr Val Leu
            100                 105

<210> SEQ ID NO 133
<211> LENGTH: 107
<212> TYPE: PRT
<213> ORGANISM: Artificial Sequence
<220> FEATURE:
<223> OTHER INFORMATION: synthetic sequence

<400> SEQUENCE: 133

Ser Tyr Glu Leu Thr Gln Pro Pro Ser Val Ser Val Ser Pro Gly Gln
1               5                   10                  15

Thr Ala Arg Ile Thr Cys Ser Gly Gly Gly Ser Ser Asn Tyr Tyr Gly
            20                  25                  30

Trp Tyr Gln Gln Lys Pro Gly Gln Ala Pro Val Leu Val Ile Tyr Ser
            35                  40                  45

Asn Asn Gln Arg Pro Ser Gly Ile Pro Glu Arg Phe Ser Gly Ser Ser
        50                  55                  60

Ser Gly Thr Thr Val Thr Leu Thr Ile Ser Gly Val Gln Ala Glu Asp
65                  70                  75                  80

Glu Ala Asp Tyr Tyr Cys Gly Ser Ala Asp Ser Ser Thr Asn Ala Gly
                85                  90                  95

Ile Phe Gly Gly Gly Thr Lys Leu Thr Val Leu
            100                 105

<210> SEQ ID NO 134
<211> LENGTH: 108
<212> TYPE: PRT
<213> ORGANISM: Artificial Sequence
<220> FEATURE:
<223> OTHER INFORMATION: synthetic sequence

<400> SEQUENCE: 134

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
            35                  40                  45

Ser Asn Asn Gln Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Ser Ala Asp Ser Ser Thr Asn Ala
                85                  90                  95

Gly Ile Phe Gly Gly Gly Thr Lys Leu Thr Val Leu
            100                 105
```

```
<210> SEQ ID NO 135
<211> LENGTH: 108
<212> TYPE: PRT
<213> ORGANISM: Artificial Sequence
<220> FEATURE:
<223> OTHER INFORMATION: synthetic sequence

<400> SEQUENCE: 135

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
        35                  40                  45

Gly Thr Asn Lys Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Ser Ala Asp Ser Ser Thr Asn Ala
                85                  90                  95

Gly Ile Phe Gly Gly Gly Thr Lys Leu Thr Val Leu
            100                 105

<210> SEQ ID NO 136
<211> LENGTH: 18
<212> TYPE: PRT
<213> ORGANISM: Artificial Sequence
<220> FEATURE:
<223> OTHER INFORMATION: synthetic sequence

<400> SEQUENCE: 136

Gly Gln Ser Ser Arg Ser Ser Gly Gly Gly Ser Ser Gly Gly Gly
1               5                   10                  15

Gly Ser

<210> SEQ ID NO 137
<211> LENGTH: 5
<212> TYPE: PRT
<213> ORGANISM: Artificial Sequence
<220> FEATURE:
<223> OTHER INFORMATION: synthetic sequence

<400> SEQUENCE: 137

Gly Gly Gly Gly Ser
1               5

<210> SEQ ID NO 138
<211> LENGTH: 5
<212> TYPE: PRT
<213> ORGANISM: Artificial Sequence
<220> FEATURE:
<223> OTHER INFORMATION: synthetic sequence

<400> SEQUENCE: 138

Gly Gly Gly Gly Ala
1               5

<210> SEQ ID NO 139
<211> LENGTH: 7
<212> TYPE: PRT
<213> ORGANISM: Artificial Sequence
<220> FEATURE:
<223> OTHER INFORMATION: synthetic sequence
```

```
<400> SEQUENCE: 139

Gly Phe Ser Phe Ser Ser Tyr
1               5

<210> SEQ ID NO 140
<211> LENGTH: 8
<212> TYPE: PRT
<213> ORGANISM: Artificial Sequence
<220> FEATURE:
<223> OTHER INFORMATION: synthetic sequence

<400> SEQUENCE: 140

Tyr Ser Ser Ala Ser Ser Thr Tyr
1               5

<210> SEQ ID NO 141
<211> LENGTH: 7
<212> TYPE: PRT
<213> ORGANISM: Artificial Sequence
<220> FEATURE:
<223> OTHER INFORMATION: synthetic sequence

<400> SEQUENCE: 141

Gly Phe Asp Phe Ser Ser Tyr
1               5

<210> SEQ ID NO 142
<211> LENGTH: 6
<212> TYPE: PRT
<213> ORGANISM: Artificial Sequence
<220> FEATURE:
<223> OTHER INFORMATION: synthetic sequence

<400> SEQUENCE: 142

Gly Ser Thr Gly Ser Ser
1               5

<210> SEQ ID NO 143
<211> LENGTH: 7
<212> TYPE: PRT
<213> ORGANISM: Artificial Sequence
<220> FEATURE:
<223> OTHER INFORMATION: synthetic sequence

<400> SEQUENCE: 143

Gly Phe Ser Ile Ser Ser Tyr
1               5

<210> SEQ ID NO 144
<211> LENGTH: 5
<212> TYPE: PRT
<213> ORGANISM: Artificial Sequence
<220> FEATURE:
<223> OTHER INFORMATION: synthetic sequence

<400> SEQUENCE: 144

Tyr Ser Gly Ser Arg
1               5

<210> SEQ ID NO 145
<211> LENGTH: 7
<212> TYPE: PRT
<213> ORGANISM: Artificial Sequence
<220> FEATURE:
<223> OTHER INFORMATION: synthetic sequence
```

```
<400> SEQUENCE: 145

Gly Phe Thr Phe Ser Ser Tyr
1               5

<210> SEQ ID NO 146
<211> LENGTH: 5
<212> TYPE: PRT
<213> ORGANISM: Artificial Sequence
<220> FEATURE:
<223> OTHER INFORMATION: synthetic sequence

<400> SEQUENCE: 146

Asp Ser Gly Ser Thr
1               5

<210> SEQ ID NO 147
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 147

Ser Gly Gly Ser Gly Ser Tyr Gly Tyr Tyr Gly
1               5                   10
```

CLAUDIN 6 ANTIBODIES AND USES THEREOF

CROSS-REFERENCE TO RELATED APPLICATIONS

This application claims priority to U.S. Provisional Application No. 62/806,048, filed Feb. 15, 2019, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: INM-003 122086-5003 Sequence Listing; date recorded: Aug. 30, 2021; file size: 81,920 bytes).

BACKGROUND

Claudin 6 is a receptor that is overexpressed on cancer cells. Targeting Claudin 6 with antibodies that are specific to Claudin 6 can help activate a cytotoxic response against Claudin 6 expressing cancers. Thus, there is a need for antibodies that can bind to Claudin 6 and antibodies that can modulate the activity of Claudin 6. The present disclosure provides for these needs as well as others.

SUMMARY

In some embodiments, isolated antibodies are provided that bind to a protein or a nucleic acid molecule encoding the same.

In some embodiments, methods of using the antibodies are provided for herein.

In some embodiments, antibodies that binds to claudin 6 with an affinity of less than 10 nM and with at least 100 fold greater $EC_{50}$ than claudin 9, claudin 3, and/or claudin 4 are provided.

In some embodiments, peptides comprising, consisting of, or consisting essentially of a sequence as provided herein, or a variant thereof, are provided.

In some embodiments, peptides comprising, consisting of, or consisting essentially of a sequence that is 90-99% identical to a sequence as provided herein, or a variant thereof, are provided.

In some embodiments, antibodies, such as a monoclonal antibody or ScFv, that bind to an epitope on Claudin 6 (SEQ ID NO: 1) whose binding residues include T33, N38, D68, P74, D76, D146, V152, A153, E154, Q156, R158, or any combination thereof, are provided. In some embodiments, the antibody binds to an epitope on Claudin 6 that includes residues E48, D68, P74, D76, and R158 of Claudin 6 (SEQ ID NO: 1). In some embodiments, the antibody binds to an epitope on Claudin 6 that includes residues T33, N38, E48, D76, A153, E154, Q156, and R158 of Claudin 6 (SEQ ID NO: 1). In some embodiments, the antibody binds to an epitope of Claudin 6 that includes residues N38, E48, Y67, P74, D76, D146, V152, E154, Q156, and R158 on Claudin 6. In some embodiments, the antibody binds to an epitope of Claudin 6 that includes residues E48, Y67, Q156, and R158 of Claudin 6.

In some embodiments, bi-specific antibodies comprising a first $V_H$ peptide that binds to Claudin 6 and second $V_H$ peptide that binds to a different moiety are provided herein.

In some embodiments, nucleic acid molecules encoding an antibody or an amino acid sequence described herein are provided. In some embodiments, vectors comprising the nucleic acid molecules are provided. In some embodiments, cells comprising the vectors or the nucleic acid molecules are provided herein.

In some embodiments, antibodies, or an isolated form thereof, that binds to claudin 6 with an affinity of less than 10 nM and with at least 100 fold greater $EC_{50}$ than claudin 9, claudin 3, and/or claudin 4 are provided.

In some embodiments, antibodies, or an isolated form thereof, wherein the antibody comprises a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, 95, 139, 141, 143, or 145, or a variant of any of the foregoing; the heavy chain CDR2 has the amino acid sequence of SEQ ID NO: 26, 32, 38, 44, 46, 48, 49, 54, 125, 72, 77, 81, 86, 91, 96, 101, 102, 140, 142, 144, or 146, or a variant of any of the foregoing; and the heavy chain CDR3 sequence has the amino acid sequence of SEQ ID NO: 27, 33, 39, 45, 57, 61, 63, 65, 66, 67, 126, 69, 73, 82, 57, 92, or 97, or a variant of any of the foregoing.

In some embodiments, the antibody of any one of claims 1-3, wherein the antibody comprises a light chain variable region comprising a sequence of any one of sequences as set forth in SEQ ID NOs: 127-135 are provided.

In some embodiments, antibodies comprising a light chain variable region comprising light chain CDR1, CDR2, and CDR3 sequences, wherein the light chain CDR1 sequence has the amino acid sequence of SEQ ID NO: 22, 28, 34, 40, 47, 50, 58, 64, 74, 83, 87, 93, or 98; the light chain CDR2 sequence has the amino acid sequence of SEQ ID NO: 23, 29, 41, 51, 59, 68, 84, 88, or 99, and the light chain CDR3 sequence has the amino acid sequence of SEQ ID NO: 24, 30, 36, 42, 52, 60, 70, 75, 79, 85, 89, 94, or variants of any of the foregoing, are provided.

In some embodiments, antibodies, or antigen binding fragments thereof, wherein the antibodies, or antigen binding fragments thereof, comprise: (i) a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing; and (ii) a light chain variable region comprising light chain CDR1, CDR2, and CDR3 sequences, wherein the light chain CDR1 sequence has the amino acid sequence 22, 28, 34, 40, 47, 50, 58, 64, 74, 83, 87, 93, or 98; the light chain CDR2 sequence has the amino acid sequence of 23, 29, 41, 51, 59, 68, 84, 88, or 99, and the light chain CDR3 sequence has the amino acid sequence of 24, 30, 36, 42, 52, 60, 70, 75, 79, 85, 89, 94, or variants of any of the foregoing, are provided.

In some embodiments, a peptide comprising, consisting of, or consisting essentially of a sequence as provided herein, or a variant thereof, is provided.

In some embodiments, antibodies, such as a monoclonal antibody or scFv, that bind to an epitope on Claudin 6 whose residues include T33, N38, D68, P74, D76, D146, V152, A153, E154, Q156, R158, or any combination thereof, are provided.

In some embodiments, antibodies, such as a monoclonal antibody or a scFv, that bind preferentially to Claudin 6 as compared to Claudin 9, wherein the antibody binds to an epitope on Claudin 6 that comprises Q156 are provided.

In some embodiments, bi-specific antibodies comprising a first $V_H$ peptide that binds to Claudin 6 and second $V_H$ peptide that binds to a different moiety are provided.

In some embodiments, pharmaceutical composition are provided comprising one or more antibodies described herein or a nucleic acid molecule encoding the same.

In some embodiments, nucleic acid molecules encoding an antibody or an amino acid sequence provided herein are provided.

In some embodiments, methods of modulating Claudin 6 activity by contacting a cell expressing Claudin 6 with a Claudin 6 antibody or a pharmaceutical composition comprising the same that binds to Claudin 6 on the cell surface are provided.

In some embodiments, methods for inhibiting the function of Claudin 6 by contacting a cell expressing Claudin 6 with an antibody or a pharmaceutical composition comprising the same that inhibits the function of Claudin 6 by binding to Claudin 6 are provided.

In some embodiments, methods of treating a subject with a Claudin 6 mediated disorder, the method comprising administering a pharmaceutical composition comprising a Claudin 6 antibody to the subject, such as any antibody provided herein or a nucleic acid molecule encoding the same are provided.

In some embodiments, methods of treating cancer in a subject, the method comprising administering a therapeutic that specifically binds to claudin 6 and binds to CD3 and/or 4-1BB are provided.

In some embodiments, methods of treating cancer in a subject, the method comprising administering to the subject a pharmaceutical composition comprising an antibody that binds to residue Q156 of Claudin 6 or nucleic acid molecule encoding the same are provided.

In some embodiments, chimeric receptors comprising an antibody domain as provided herein are provided.

In some embodiments, compositions comprising an antibody an antibody domain as provided herein linked to a drug or other therapeutic are provided.

In some embodiments, compositions comprising a peptide as provided herein, such as a peptide comprising one or more sequences of SEQ ID NO: 2-135 are provided.

In some embodiments, methods of detecting the presence or absence of Claudin 6 in a sample comprising contacting a sample with an antibody as provided herein and any of the preceding claims and detecting the binding to a Claudin 6 antigen by the antibody, wherein the detection of the binding indicates the presence Claudin 6; or the absence of the detection of the binding to the Claudin 6 indicates the absence of the Claudin 6 are provided.

In some embodiments, methods of delivering a composition to a cell expressing Claudin 6, the method comprising contacting a cell with an antibody as provided herein, wherein the antibody is linked to another molecule to be delivered to the cell expressing Claudin 6 are provided.

In some embodiments, methods of contacting a composition to a cell expressing Claudin 6, the method comprising contacting a cell with an antibody as provided herein, wherein the antibody is linked to another molecule to contact with the cell expressing Claudin 6 are provided.

BRIEF DESCRIPTION OF DRAWINGS

FIG. 5 illustrates various embodiments as provided for herein, including MAb binding to PA-1 cells naturally expressing Claudin-6, which was detected by flow cytometry.

FIG. 8 illustrates various embodiments as provided herein.

DETAILED DESCRIPTION

Figure 1:
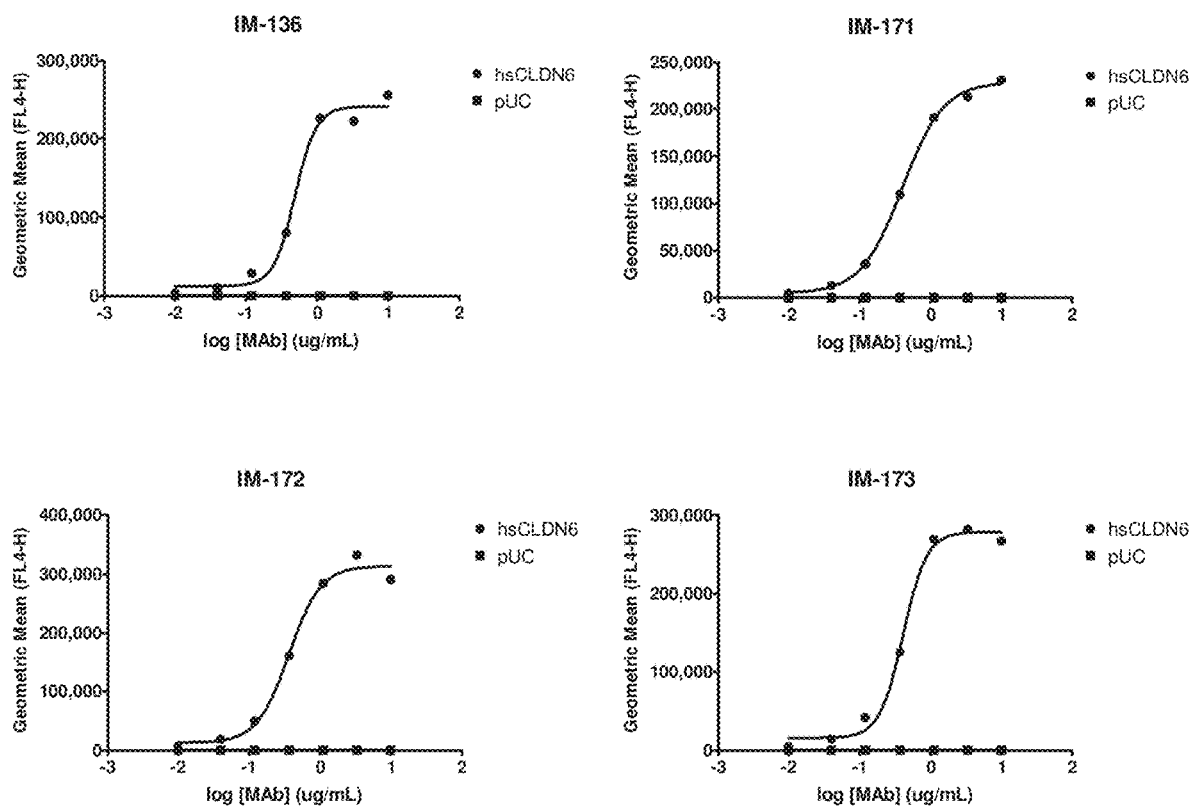
FIG. 1 illustrates the binding of exemplary, not-limiting, embodiments of antibodies that bind to Claudin 6.

Here it is described and disclosed the isolation and characterization of MAbs (monoclonal antibodies) that recognize Claudin 6. In some embodiments, MAbs against Claudin 6 were generated using virus-like particles (VLPs) to present this multispanning membrane protein in its native conformation. In some embodiments, the antibodies bind to Claudin 6, but do not significantly bind to Claudin 9. In some embodiments, the antibody binds to the Claudin 6 with an affinity, $EC_{50}$, or $K_D$ at least, or about, 10, 20, 30, 40, 50, 75, 100, 200, or 300 times greater than it binds to Claudin 9. In some embodiments, the antibodies bind to Claudin 6, but do not significantly bind to Claudin 3. In some embodiments, the antibody binds to the Claudin 6 with an affinity, $EC_{50}$, or $K_D$ at least, or about, 10, 20, 30, 40, 50, 75, 100, 200, or 300 times greater than it binds to Claudin 3. In some embodiments, the antibodies bind to Claudin 6, but do not significantly bind to Claudin 4. In some embodiments, the antibody binds to the Claudin 6 with an affinity, $EC_{50}$, or $K_D$ at least, or about, 10, 20, 30, 40, 50, 75, 100, 200, or 300 times greater than it binds to Claudin 4.

In some embodiments, Claudin 6 comprises an amino acid sequence comprising:

```
Claudin 6 (human)  SEQ ID NO: 1  MASAGMQILGVVLTLLGWVNGLVSCALPMWKVTAFIGN
                                 SIVVAQVVWEGLWMSCVVQSTGQMQCKVYDSLLALPQD
                                 LQAARALCVIALLVALFGLLVYLAGAKCTTCVEEKDSK
                                 ARLVLTSGIVFVISGVLTLIPVCWTAHAVIRDFYNPLV
                                 AEAQKRELGASLYLGWAASGLLLLGGGLLCCTCPSGGS
                                 QGPSHYMARYSTSAPAISRGPSEYPTKNYV
```

The term "antibody" as used herein is meant in a broad sense and includes immunoglobulin or antibody molecules including polyclonal antibodies, monoclonal antibodies including murine, human, humanized and chimeric monoclonal antibodies and antibody fragments, such as ScFv or hexabodies (PLOS Biology 1 DOI:10.1371/journal.pbio.1002344 Jan. 6, 2016, which is hereby incorporated by reference in its entirety).

The term "humanized antibody", "engineered antibody", "human framework adapted", and "HFA" as used herein, is intended to include antibodies having variable region frameworks derived from sequences of human origin. Furthermore, if the antibody contains a constant region, the constant region can be derived from such human sequences, e.g., human germline sequences, or naturally occurring (e.g., allotypes) or mutated versions of human germline sequences. The humanized antibodies may include amino acid residues not encoded by human sequences (e.g., mutations introduced by random or site-specific mutagenesis in vitro or by somatic mutation in vivo).

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragment" means a portion of an intact antibody, generally the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies.

The term "antigen" as used herein means any molecule that has the ability to generate antibodies either directly or indirectly. Included within the definition of "antigen" is a protein-encoding nucleic acid.

As used herein, "specific binding" or "immunospecific binding" or "binds immunospecifically" refer to antibody binding to a predetermined antigen (e.g. Claudin 6) or epitope present on the antigen. In some embodiments, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing Claudin 6" and "an antibody specific for Claudin 6" are used interchangeably herein with the term "an antibody which binds immunospecifically to Claudin 6." Reference in the present disclosure may be made to Claudin 6. In some embodiments, the antibody is specific for Claudin 6 and does not specifically bind to claudin 3, claudin 4, and/or claudin 9.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

The term "homolog" means protein sequences having between 40% and 100% sequence identity to a reference sequence. Percent identity between two peptide chains can be determined by pair wise alignment using the default settings of the AlignX module of Vector NTI v.9.0.0 (Invitrogen Corp., Carlsbad, Calif.). In some embodiments, the an antibody or fragment thereof has at least 50, 60, 70, 80, 90, 91, 92, 93, 94, 95, 96, 97, 98, or 99% identity to a sequence described herein. In some embodiments, the antibody has conservative substitutions as compared to a sequence described herein. In some embodiments, the number of substitutions can be 1, 2, 3, 4, 5, 6, 7, 8, or 9. These molecules that differ based on % identity or substitutions can also be referred to as "variants." Antibodies having conservative substitutions in the heavy and light chain sequences are shown below in Table 1, and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the Table 1 below.

TABLE

Exemplary Conservative Substitutions:

| Original Residue | Exemplary Conservative Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |

TABLE-continued

Exemplary Conservative Substitutions:

| Original Residue | Exemplary Conservative Substitutions |
|---|---|
| Trp | Tyr, Phe |
| Tyr | Trp, Phe, Thr, Ser |
| Val | Ile, Met, Leu, Phe, Ala |

The term "in combination with" as used herein means that the described agents can be administered to an animal together in a mixture, concurrently as single agents or sequentially as single agents in any order.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495 497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273 3277 (1984); Morrison et al., Proc. Natl. Acad. Sci. USA 81:6851 6855 (1984); Boulianne et al., Nature 312:643 646 (1984); Cabilly et al., European Patent Application 125023 (published Nov. 14, 1984); Neuberger et al., Nature 314:268 270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066 1074 (1986); Robinson et al., International Patent Publication WO 1987/002671 (published May 7, 1987); Liu et al., Proc. Natl. Acad. Sci. USA 84:3439 3443 (1987); Sun et al., Proc. Natl. Acad. Sci. USA 84:214 218 (1987); Better et al., Science 240:1041 1043 (1988); and Harlow and Lane Antibodies. a Laboratory Manual Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

The modifier "monoclonal" indicates the substantially homogeneous character of the antibody and does not require production of the antibody by any particular method. For example, murine mAbs can be made by the hybridoma method of Kohler et al., Nature 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., Proc. Natl. Acad. Sci. (USA), 86:10029-10032 (1989) and Hodgson et al., Bio/Technology, 9:421 (1991).

In addition to the antibodies described herein, exemplary human framework sequences useful for humanization are disclosed at www"dot"ncbi"dot"nlm"dot"nih"dot"gov/entrez/query"dot"fcgi; www"dot"ncbi"dot"nih"dot"gov/ig-blast; www"dot"atcc"dot"org/phage/hdb"dot"html; www"dot"mrc-cpe"dot"cam"dot"ac"dot"uk/ALIGNMENTS"dot"php; "dot" www"dot"kabatdatabase"dot"com/top"dot"html; ftp"dot"ncbi"dot"nih"dot"gov/repository/kabat; www"dot"sciquest"dot"com; www"dot"abcam"dot"com; www"dot"antibodyresource-"dot"com/onlinecomp"dot"html; www"dot"public"dot"iastate"dot"edu/"dot"about"dot"pedro/research_tools"dot"html; www"dot"whfreeman"dot"com/immunology/CH05/kuby05"dot"htm; www"dot"hhmi"dot"org/grants/lectures/1996/vlab; www"dot"path"dot"cam"dot"ac"dot"uk/"dot"about-"dot"mrc7/mikeimages"dot"html; mcb"dot"harvard "dot"edu/BioLinks/Immunology"dot"html; www"dot"immunologylink"dot"com; pathbox"dot"wustl"dot"edu/"dot"about"dot"hcenter/index"dot"html; www"dot"appliedbiosystems"dot"com; www"dot"nal"dot"usda"dot"gov/awic/pubs/antibody; www"dot"m"dot"ehime-u"dot"ac"dot"jp/"dot"about"dot"yasuhito/Elisa"dot"html; www"dot"biodesign"dot"com; www"dot"cancerresearchuk"dot"org; www"dot"biotech"dot"ufl"dot"edu; www"dot"isac-net"dot"org; baserv"dot"uci"dot"kun"dot"nl/"dot"about-"dot"jraats/links1 "dot"html; www"dot"recab"dot"uni-hd- "dot"de/immuno"dot"bme"dot"nwu"dot"edu; www"dot"mrc-cpe "dot"cam"dot"ac"dot"uk; www"dot"ibt"dot"unam"dot"mx/vir/V_mice"dot"html; http://www"dot"bioinf"dot"org"dot"uk/abs; antibody"dot"bath"dot"ac"dot"uk; www"dot"unizh" dot"ch; www"dot"cryst"dot"bbk"dot"ac-"dot"uk/"dot" about"dot"ubcg07s; www"dot"nimr "dot"mrc"dot"ac"dot"uk/CC/ccaewg/ccaewg"dot"html; www"dot"path"dot"cam"dot"ac"dot"uk/"dot"about-"dot"mrc7/humanisation/TAHHP"dot"html; www"dot"ibt-"dot"unam"dot"mx/vir/structure/stat_aim"dot"html; www"dot"bio sci"dot"missouri"dot"edu/smithgp/index"dot"html; www"dot"jerini"dot"de; imgt-"dot"cines"dot"fr; and Kabat et al., Sequences of Proteins of Immunological Interest, U.S. Dept. Health (1987), each entirely incorporated herein by reference. The "dot" in the world wide web addresses referenced herein can be replaced with a "." as appropriate.

The antibodies described herein can include, but are not limited to, at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$) which binds a portion of a Claudin 6 and can be used to detect the antigen. The antibodies can also be monoclonal antibodies that are made by immunizing chickens. The variable chains from the nucleic acid sequences encoding the isolated monoclonal antibodies can be isolated by using techniques, such as but not limited to, PCR. The variable chains isolated by these techniques can then be placed in a scFv vector with a human Fc. Accordingly, the antibodies can be antibodies that have a human Fc and two scFv arms. The antibodies, such as those described here and throughout the present disclosure can then be modified to be human or humanized antibodies. Examples of how to modify an antibody, including chicken antibodies, can be found in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vasquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in chickens, goats, rabbits, or other small animals.

As used herein, the term "antigen binding region" refers to that portion of an antibody molecule which contains the amino acid residues that interact with an antigen (e.g. Claudin 6) and confer on the antibody its specificity and affinity for the antigen. The antibody region includes the "framework" amino acid residues necessary to maintain the proper conformation of the antigen-binding residues. In some embodiments, the antigen binding region will be of murine origin. In some embodiments, the antigen binding region can be derived from other animal species, in particular rodents such as rabbit, rat or hamster, or birds such as chickens. It has been shown that the antigen-binding function of an antibody can be performed by fragments of a full-length antibody. Examples of binding fragments encompassed within the term "antigen-binding portion" of an antibody include a Fab fragment, a monovalent fragment having the VL, VH, CL and CH1 domains; a F(ab)$_2$ fragment, a bivalent fragment comprising two Fab fragments linked by a disulfide bridge(s) at a hinge region; a Fd fragment having the VH and CH1 domains; a Fv fragment having the VL and VH domains of a single arm of an antibody; a domain antibody or dAb fragment (Ward et al., 1989 Nature 341:544-546), which consists of a VH domain; and an isolated complementarity determining region (CDR), especially a CDR3 (See for example the WO03/025019, the contents of which are incorporated herein by reference).

The term "Complementarity Determining Regions (CDRs)" is based on sequence variability (Wu and Kabat, J. Exp. Med. 132:211-250, 1970). There are six CDRs—three in the variable heavy chain, or VH, and are typically designated H-CDR1, H-CDR2, and H-CDR3, and three CDRs in the variable light chain, or VL, and are typically designated L-CDR1, L-CDR2, and L-CDR3 (Kabat et al., Sequences of Proteins of Immunological Interest, 5th Ed. Public Health Service, National Institutes of Health, Bethesda, Md., 1991). "Hypervariable region", "HVR", or "HV" refer to the regions of an antibody variable domain which are variable in structure as defined by Chothia and Lesk (Chothia and Lesk, Mol. Biol. 196:901-917, 1987). There are six HVRs, three in VH (H1, H2, H3) and three in VL (L1, L2, L3). Chothia and Lesk refer to structurally conserved HVs as "canonical structures." Another method of describing the regions that form the antigen-binding site has been proposed by Lefranc (Lefranc et al., Developmental & Comparative Immunology 27:55-77, 2003) based on the comparison of V domains from immunoglobulins and T-cell receptors (Lefranc et al., Developmental & Comparative Immunology 27:55-77, 2003). The antigen-binding site can also be delineated based on "Specificity Determining Residue Usage (SDRU)", according to Almagro (Almagro, Mol. Recognit. 17:132-43, 2004), where SDRU refers to amino acid residues of an immunoglobulin that are directly involved in antigen contact.

Furthermore, although the two domains of the Fv fragment, VL and VH, are encoded by separate genes naturally, they can be joined, using recombinant methods, by a synthetic linker that enables them to be made as a single protein chain in which the VL and VH regions pair to form monovalent molecules (known as single chain Fv (scFv); see e.g., Bird et al., 1988 Science 242:423-426; and Huston et al., 1988 Proc. Nat. Acad. Sci. 85:5879-5883). Such single chain antibodies are encompassed by the term "antigen-binding portion" of an antibody. These antibody fragments are obtained using conventional techniques known to those of skill in the art, and can be used in the same manner as intact antibodies.

An "isolated antibody," as used herein, refers to an antibody that is substantially free of other antibodies having different antigenic specificities (e.g., an isolated antibody that specifically binds Claudin 6 is substantially free of antibodies that specifically bind antigens other than Claudin 6). Moreover, an isolated antibody may be substantially free of other cellular material and/or chemicals. An isolated antibody can also be sterile or pyrogen free or formulated as injectable pharmaceutical as described herein.

In some embodiments, the source for the DNA encoding a non-human antibody include cell lines which produce antibody, such as hybrid cell lines commonly known as hybridomas.

An "antigen" is a molecule or a portion of a molecule capable of being bound by an antibody which is additionally capable of inducing an animal to produce antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens. In some embodiments, antigens that bind antibodies, fragments and regions of the antibodies include at least 5 amino acids. In some embodiments, the antigen is the Claudin 6 protein expressed on the surface of a cell or particle. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. By expressing the receptor on the surface of the cell or particle, e.g. lipoparticle, the receptor can present conformational epitopes that may otherwise not be present if purified protein is used. An example is provided herein. In some embodiments, an adjuvant is not used, but an adjuvant can be used. In some embodiments, the particles are injected into a bird (e.g. chicken) to stimulate an immune response and generate antibodies against the protein present on the surface of the particle. Particles suitable for the generation of antibodies are described in U.S. Pat. Nos. 8,377,691, 7,763,258, 8,158,130 and U.S. Patent Application Publication Nos. 20050123563 and 20120195882, each of which is hereby incorporated by reference. These publications and patents describe the generation of various particles, including lipoparticles, that can be used to express membrane spanning proteins (e.g. multiple-membrane spanning proteins, ion channels, and the like).

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain). In some embodiments, murine and chimeric antibodies, fragments and regions comprise individual heavy (H) and/or light (L) immunoglobulin chains.

Antibodies, fragments or derivatives having chimeric H chains and L chains of the same or different variable region binding specificity, can also be prepared by appropriate association of the individual polypeptide chains, according to known method steps, e.g., according to Ausubel infra, Harlow infra, and Colligan infra, the contents of which references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated.

Alternatively, the hosts can be co-cultured and the chains allowed to associate spontaneously in the culture medium, followed by recovery of the assembled immunoglobulin, fragment or derivative.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3X63Ag8 (ATCC TIB9), or its derivatives. See, e.g., Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. This will lead to a more effective response. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vasquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

The antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference.

The cell fusions are accomplished by standard procedures well known to those skilled in the field of immunology.

Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

The antigen-specific murine or chimeric mAb can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In some embodiments, the antibody is a MAb which binds to Claudin 6. In some embodiments, the antibody binds to amino acids of an epitope of the Claudin 6. The epitopes are described herein, such as in the Tables provided in the figures and described in the Examples. In some embodiments, the antibody binds specifically to the proteins and antigens described herein.

In some embodiments, the antibody comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to Claudin 6. The CDRs and antibody sequences provided herein also be humanized or made fully human according to known methods. The sequences can also be made into chimeric antibodies as described herein.

In some embodiments, the antibody comprises an amino acid sequence comprising a sequence provided for herein or a fragment thereof. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

Fragments include, for example, Fab, Fab', F(ab')$_2$ and Fv. These fragments lack the Fc fragment of intact antibody, clear more rapidly from the circulation, and can have less non-specific tissue binding than an intact antibody (Wahl et al., J. Nucl. Med. 24:316 325 (1983)). These fragments are produced from intact antibodies using methods well known in the art, for example by proteolytic cleavage with enzymes such as papain (to produce Fab fragments) or pepsin (to produce F(ab')$_f$ fragments).

The identification of these antigen binding region and/or epitopes recognized by Abs described herein provide the information necessary to generate additional monoclonal antibodies with similar binding characteristics and therapeutic or diagnostic utility that parallel the embodiments of this application.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a Claudin 6 antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C regions genes can be derived from any human cell including those which express and produce human immunoglobulins. The human $C_H$ region can be derived from any of the known classes or isotypes of human H chains, including gamma, t, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa or lambda.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH$_1$ domain and hinge region of the H chain, followed by a translational stop codon to yield the truncated molecule.

Generally, the murine, human or murine and chimeric antibodies, fragments and regions of the antibodies described herein are produced by cloning DNA segments encoding the H and L chain antigen-binding regions of a Claudin 6 antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to some of the embodiments described herein involve several steps, as exemplified below: 1. isolation of messenger RNA (mRNA) from the cell line producing an anti-Claudin 6 antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region (Cγ-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human Cγ-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M or higher, such as at least about 10-s M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a Kd equal or less than $10^{-9}$M, $10^{-10}$M, or $10^{-11}$M for its binding partner (e.g. antigen). In some embodiments, the capture reagent has a Ka greater than or equal to $10^9 M^{-1}$ for its binding partner.

Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

In addition to the fragments described herein, non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)₃ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

These antibodies can be obtained using conventional techniques known to those skilled in the art and described herein, and the fragments are used in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and biosensor analysis, to identify one or more hybridomas that produce an antibody that specifically interacts with a molecule or compound of interest.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Administration, Compositions, and Kits Comprising the Antibodies

Whereas, an isolated antibody binds an epitope on a Claudin 6 protein, or other protein described herein, and displays in vitro and/or in vivo Claudin 6 inhibiting or therapeutic activities, the antibodies or antigen binding fragments thereof, capable of inhibiting Claudin 6 function, are suitable both as therapeutic and prophylactic agents for treating or preventing Claudin 6-associated conditions in humans and animals. These conditions include, but are not limited to, benign and metastatic forms of cancer, for example, ovarian cancer (e.g. ovarian carcinoma), reproductive cancers (breast, cervical, testicular, uterine, and placental cancers), lung cancer, gastric cancer, hepatic cancer, pancreatic cancer, bile duct cancer, cancer of the urinary bladder, kidney cancer, colon cancer, small bowel cancer, skin cancer, head and neck cancer, sarcoma, and germ cell tumors, among others.

In some embodiments, the methods comprise administering a therapeutically or prophylactically effective amount of one or more monoclonal antibodies or antigen binding fragments of the antibodies described herein to a susceptible subject or to one exhibiting a condition in which Claudin 6 is known to have caused the pathology observed. Any active form of the antibody can be administered, including, but not limited to Fab and F(ab')2 fragments.

As used herein, a Claudin 6 associated pathology refers to conditions that are caused by the function or aberrant function of a Claudin 6 receptor. These conditions include, but are not limited to, benign and metastatic forms of cancer, for example, ovarian cancer (e.g. ovarian carcinoma), reproductive cancers (breast, cervical, testicular, uterine, and placental cancers), lung cancer, gastric cancer, hepatic cancer, pancreatic cancer, bile duct cancer, cancer of the urinary bladder, kidney cancer, colon cancer, small bowel cancer, skin cancer, head and neck cancer, sarcoma, germ cell tumors, and the like.

In some embodiments, the antibodies used are compatible with the recipient species such that the immune response to the MAbs does not result in an unacceptably short circulating half-life or induce an immune response to the MAbs in the subject. In some embodiments, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies described herein. The antibodies can be provided in a kit as described below. The antibodies can be used or administered alone or in admixture with another therapeutic, analgesic, or diagnostic agent. In providing a patient with an antibody, or fragment thereof, capable of binding to Claudin 6, or an antibody capable of protecting against Claudin 6, pathology in a recipient patient, the dosage of administered agent will vary depending upon such factors as the patient's age, weight, height, sex, general medical condition, previous medical history, etc.

Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41). Additional pharmaceutical methods may be employed to control the duration of action. Controlled release preparations may be achieved through the use of polymers to complex or absorb the compounds. Another possible method to control the duration of action by controlled release preparations is to incorporate the compounds of into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The antibody compositions described herein can be prepared for use for parenteral (subcutaneous, intramuscular or intravenous) or any other administration particularly in the form of liquid solutions or suspensions. The formulation can also be suitable for an injectable formulation. In some embodiments, the injectable formulation is sterile. In some embodiments, the injectable formulation is pyrogen free. In some embodiments, the formulation is free of other antibodies that bind to other antigens other than an antigen described herein.

An antibody, capable treating a condition associated with Claudin 6 activity or use to treat a Claudin 6 related pathology, is intended to be provided to subjects in an amount sufficient to affect a reduction, resolution, or amelioration in the Claudin 6 related symptom or pathology. Such a pathology includes benign or metastatic cancer, for example, ovarian cancer (e.g., ovarian carcinoma), reproductive cancer (breast, cervical, testicular, uterine, or placental cancer), lung cancer, gastric cancer, hepatic cancer, pancreatic cancer, bile duct cancer, cancer of the urinary bladder, kidney cancer, colon cancer, small bowel cancer, skin cancer, head and neck cancer, sarcoma, or germ cell tumor, in a subject.

An amount is said to be sufficient or a "therapeutically effective amount" to "affect" the reduction of symptoms if the dosage, route of administration, and dosing schedule of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient. In some embodiments, an amount is a therapeutically effective amount if it is an amount that can be used to treat, ameliorate or prevent benign and metastatic forms of cancer, for example, ovarian cancer (e.g., ovarian carcinomas), reproductive cancers (breast, cervical, testicular, uterine, and placental cancers), lung cancer, gastric cancer, hepatic cancer, pancreatic cancer, bile duct cancer, cancer of the urinary bladder, kidney cancer, colon cancer, small bowel cancer, skin cancer, head and neck cancer, sarcoma, and germ cell tumors, by, for example, but not limited to modulating Claudin 6 function, Claudin 6-mediated regulation of the tight junction integrity, and the like. In some embodiments, the antibody or the therapeutic does not bind to other claudin proteins, such as but not limited to claudin 9, claudin 3, and/or claudin 4. In some embodiments, the antibody is specific for Claudin 6.

The antibodies can be formulated according to known methods to prepare pharmaceutically useful compositions, whereby these materials, or their functional derivatives, are combined in admixture with a pharmaceutically acceptable carrier vehicle. The treatment may be given in a single dose schedule, or a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting Claudin 6 protein in a biological sample. The kit includes a container holding one or more antibodies which binds an epitope of Claudin 6 protein and instructions for using the antibody for the purpose of binding to Claudin 6 protein to form an immunological complex and detecting the formation of the immunological complex such that the presence or absence of the immunological complex correlates with presence or absence of Claudin 6 protein in the sample. Examples of containers include multiwell plates which allow simultaneous detection of Claudin 6 protein in multiple samples.

In some embodiments, antibodies that bind to a Claudin 6 protein are provided. In some embodiments, antibodies, such as a monoclonal antibody or ScFv, that bind to an epitope on Claudin 6 whose binding residues include T33, N38, D68, P74, D76, D146, V152, A153, E154, Q156, R158, or any combination thereof, are provided. In some embodiments, the antibody binds to an epitope on Claudin 6 that includes residues E48, D68, P74, D76, and R158 of Claudin 6. In some embodiments, the antibody binds to an epitope on Claudin 6 that includes residues T33, N38, E48, D76, A153, E154, Q156, and R158 of Claudin 6. In some embodiments, the antibody binds to an epitope of Claudin 6 that includes residues N38, E48, Y67, P74, D76, D146, V152, E154, Q156, and R158 on Claudin 6. In some embodiments, the antibody binds to an epitope of Claudin 6 that includes residues E48, Y67, Q156, and R158 of Claudin 6. In some embodiments, the antibody binds to an epitope of Claudin 6 that includes residue Q156.

In some embodiments, the antibody is isolated. In some embodiments, the antibody binds specifically. In some embodiments, the antibody binds to a Claudin 6 protein that is properly folded. In some embodiments, the antibody binds to a Claudin 6 protein in a cell membrane. In some embodiments, the antibody binds to a Claudin 6 protein that is in a cell membrane in an intact cell. In some embodiments, the antibody inhibits or neutralizes the function of a Claudin 6 protein. As used herein, the term "neutralize" means that the activity or function of the protein is inhibited. In some embodiments, the antibody inhibits regulation of the tight junction integrity by Claudin 6. In some embodiments, the antibody is used as a targeting moiety to deliver another therapeutic to the cells expressing (e.g. tumor cells) to Claudin 6. In some embodiments, the claudin 6 antibody is part of a multi-specific therapeutic where one part of the molecule binds to Claudin 6 and another part of the therapeutic binds to another target. In some embodiments, the other part is CD3 binding molecule (e.g. CD3 antibody) or another molecule that facilitates ADC, ADCC, or CAR-T therapy. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the interactions or functions facilitated by Claudin 6.

In some embodiments, the antibody comprises a sequence as provided for herein or antigen binding fragment thereof. In some embodiments, the antibody comprises a heavy chain CDR or an antigen binding fragment thereof described herein. The heavy chain may be one or more of the heavy chains described herein. In some embodiments, the antibody comprises a light chain, or an antigen binding fragment thereof as described herein.

In some embodiments, methods of treating, inhibiting or ameliorating a Claudin 6, associated pathology are provided. In some embodiments, the methods comprise administering an antibody described herein or a pharmaceutical composition described herein to a subject to treat, inhibit or ameliorate a Claudin 6 associated pathology. In some embodiments, the pathology is benign or metastatic cancer, for example, ovarian cancer (e.g., ovarian carcinoma), reproductive cancer (breast, cervical, testicular, uterine, endometrial, or placental cancer), lung cancer, gastric cancer, stomach cancer, hepatic cancer, pancreatic cancer, bile duct cancer, cancer of the urinary bladder, kidney cancer, colon cancer, small bowel cancer, lung cancer (e.g. lung adenocarcinoma), skin cancer, head and neck cancer, sarcoma, or germ cell tumor.

In some embodiments, the antibodies provided herein are administered to the subject as nucleic acid molecule encoding the antibody. In some embodiments, the nucleic acid molecule is a DNA molecule, RNA, or mRNA molecule encoding the antibody. The nucleic acid molecule can be delivered in any form suitable for expression in vivo, such as a viral vector, plasmid, linear nucleic acid molecule, and the like. In some embodiments, the antibody produced by the nucleic acid molecule can function as a vaccine or circulating antibody that is used to identify and kill cells that express Claudin 6. The expression of the antibody can be prolonged or controlled expression that is stimulated. Without being bound to any theory, in some embodiments, a subject that develops cancer that expresses Claudin 6 would be treated by the circulating antibody that would recognize the cancer cell. Thus, in some embodiments, the antibody being delivered by a nucleic acid molecule can be used to treat or prevent the growth of the cancer. In some embodiments, the nucleic acid molecule encoding the antibody is integrated into the genome of a cell of the subject so that the expression is persistent. Examples of viral vectors that could be used include, but are not limited to, AAV, AV, retroviral vectors that integrate intot the genome, and the like.

In some embodiments, methods of detecting the presence or absence of a Claudin 6 in a sample are provided, the method comprising contacting a sample with one or more antibodies described herein detecting the binding to a Claudin 6 antigen by the antibody. In some embodiments, the detection of the binding indicates the presence Claudin 6 antigen; or the absence of the detection of the binding to the Claudin 6 antigen indicates the absence of the Claudin 6 antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody that binds to an epitope on Claudin 6 protein, are provided, the method comprising contacting a test antibody with the epitope on Claudin 6 protein and determining whether the test antibody binds to the epitope. In some embodiments, the determining comprises determining whether the test antibody binds to the protein and is competitively inhibited by an antibody comprising a sequence as provided herein. In some embodiments, the determining comprises mutating one or more residues of epitope or protein and determining binding of the test antibody to the mutated epitope, wherein if the mutation reduces binding of the test antibody as compared to the non-mutated epitope, the test antibody is deemed to bind to that epitope.

In some embodiments, methods of inducing an immune response against a Claudin 6 antigen are provided, the methods comprising administering a Claudin 6 antigen to a subject under conditions sufficient to induce an immune response. In some embodiments, the Claudin 6 antigen is delivered as a nucleic acid molecule encoding the Claudin 6 antigen. As discussed herein, in some embodiments, the methods comprise administering a lipoparticle comprising a Claudin 6 antigen to the subject to induce the immune response. In some embodiments, antibodies produced by the immune response are isolated. The antibodies can then be cloned, isolated and/or otherwise modified as described herein. In some embodiments, the subject is a chicken.

In some of the embodiments of the methods provided herein, the antibody is any antibody or fragment thereof as provided herein.

In some embodiments, the antibody comprises a $V_H$ and a $V_L$ sequence as forth in the following table:

| IM Ab ID | VH | VL |
|---|---|---|
| 136 | AVTLDESGGGLQTPGGVLSLVCKASGFSFSS YDMGWVRQAPGKGLEWVASIYSSASSTYYAP AVKGRATITRDNGQSTVRLQLNNLRAEDTGT YYCAKAAGRTYRGWATYIADSIDAWGHGTEV IVSS (SEQ ID NO: 2) | ALTQPSSVSANPGESVEITCSGDSSWYGYGWYQ QKSPGSAPVTLIYESGKRPSDIPSRFSGSTSGS TATLTITGVQADDEAVYYCGSADSNSIGIFGAG TTLTVL (SEQ ID NO: 3) |
| 171 | AVTLDESGGGLQTPGGALSLVCKASGFDFSS YAMNWVRQAPGKGLEWVAGIGSTGSSTGYGP AVKGRATISRDNGQSTLRLQLNNLRAEDTAI YYCAKSVGNGNSWSGYIATSIDAWGHGTEVI VSS (SEQ ID NO: 4) | ALTQPSSVSANLGGTVKLTCSGGSSGYGWYQQK SPGSAPVTVIYSNDKRPSDIPSRFSGSLSGSTG TLTITGVQADDEAVYFCGSTDNSYVGIFGAGTT LTVL (SEQ ID NO: 5) |
| 172 | AVTLDESGGGLQTPGGALSLVCKGSGFSISS YTMQWVRQAPGKGLEWVAGIYSGSRTYYGAA VQGRATISRDNGQSTVRLQLNNLRAEDTGTY YCAKSSYCTAWTGCDVYAGGSIDAWGHGTEV IVSS (SEQ ID NO: 6) | ALTQPSSVSATPGGTVEITCSGDSSDDGSYYYG WYQQKSPGSAPVTVIYSNDKRPSSIPSRFSGSA SGSTATLTITGVQADDEAVYFCGSYDSSTGIFG AGTTLTVL (SEQ ID NO: 7) |
| 173 | AVTLDESGGGLQTPGGALSLVCKASGFTFSS YSMFWVRRAPGKGLEWVAGIDSGSTTFYGSA VKGRATISRDNGQSTVRLQLNNLRAEDTATY YCAKDAYGYCGWSGCSADSIDAWGHGTEVIV SS (SEQ ID NO: 8) | ALTQPSSVSANPGGTVEITCSGGNNYYGWYQQK SPGSAPVTVIYYNDKRPSDIPSRFSGSKSGSTG TLTITGVQADDEAVYFCGGWDSSGGIFGAGTTL TVL (SEQ ID NO: 9) |
| 179 | EVQLLESGGGLVQPGGSLRLSCAASGFSFSS YDMGWVRQAPGKGLEWVASIYSSASSTYYAD SVKGRFTISRDNSKNTLYLQMNSLRAEDTAV YYCAKAAGRTYRGWATYIADSIDAWGQGTLV TVSS (SEQ ID NO: 10) | SYELTQPPSVSVSPGQTARITCSGDSSWYGYGW YQQKPGQAPVLVIYESGKRPSGIPERFSGSSSG TTVTLTISGVQAEDEADYYCGSADSNSIGIFGG GTKLTVL (SEQ ID NO: 11) |
| 180 | EVQLLESGGGLVQPGGSLRLSCAASGFDFSS YAMNWVRQAPGKGLEWVAGIGSTGSSTGYAD SVKGRFTISRDNSKNTLYLQMNSLRAEDTAV YYCAKSVGNGNSWSGYIATSIDAWGQGTLVT VSS (SEQ ID NO: 12) | SYELTQPPSVSVSPGQTARITCSGGSSGYGWYQ QKPGQAPVLVIYSNDKRPSGIPERFSGSSSGTT VTLTISGVQAEDEADYYCGSTDNSYVGIFGGGT KLTVL (SEQ ID NO: 13) |
| 181 | EVQLLESGGGLVQPGGSLRLSCAASGFSISS YTMQWVRQAPGKGLEWVAGIYSGSRTYYADS | SYELTQPPSVSVSPGQTARITCSGDDGSYYYGW YQQKPGQAPVLVIYSNDKRPSGIPERFSGSSSG |

-continued

| IM Ab ID | VH | VL |
|---|---|---|
| | VKGRFTISRDNSKNTLYLQMNSLRAEDTAVY YCAKSSYCTAWTGCDVYAGGSIDAWGQGTLV TVSS (SEQ ID NO: 14) | TTVTLTISGVQAEDEADYYCGSYDSSTGIFGGG TKLTVL (SEQ ID NO: 15) |
| 182 | EVQLLESGGGLVQPGGSLRLSCAASGFTFSS YSMFWVRQAPGKGLEWVAGIDSGSTTFYADS VKGRFTISRDNSKNTLYLQMNSLRAEDTAVY YCAKDAYGYCGWSGCSADSIDAWGQGTLVTV SS (SEQ ID NO: 16) | SYELTQPPSVSVSPGQTARITCSGGNNYYGWYQ QKPGQAPVLVIYYNDKRPSGIPERFSGSSSGTT VTLTISGVQAEDEADYYCGGWDSSGIFGGGTK LTVL (SEQ ID NO: 17) |
| 271 | EVQLLESGGGLVQPGGSLRLSCAASGFTFSS YAMSWVRQAPGKGLEWVAGISSSGRYTGYAD SVKGRFTISRDNSKNTLYLQMNSLRAEDTAV YYCAKSVGNGNSWSGYIATSIDAWGQGTLVT VSS (SEQ ID NO: 18) | SYELTQPPSVSVSPGQTARITCSGGSGSYGWYQ QKPGQAPVLVIYGTNKRPSGIPERFSGSSSGTT VTLTISGVQAEDEADYYCGSADSSTNAGIFGGG TKLTVL (SEQ ID NO: 19) |
| 272 | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSVGNGNSWSGYIATSIDAWGQGTLVT VSS (SEQ ID NO: 20) | SYELTQPPSVSVSPGQTARITCSGGSGSYGWYQ QKPGQAPVTVIYGTNKRPSGIPERFSGSSSGTT VTLTISGVQAEDEADYYCGSADSSTNAGIFGGG TKLTVL (SEQ ID NO: 21) |
| CH-HAMF 5-1HAQ | EVQLLESGGGLVQPGGSLRLSCAASGFTFSS YAMSWVRQAPGKGLEWVAGISSSGRYTGYAD SVKGRFTISRDNSKNTLYLQMNSLRAEDTAV YYCAKSVGNGNSWSGYVATSIDAWGQGTLVT VSS (SEQ ID NO: 103) | SYELTQPPSVSVSPGQTARITCSGGSGSYGWYQ QKPGQAPVLVIYGTNKRPSGIPERFSGSSSGTT VTLTISGVQAEDEADYYCGSADSSTNAGIFGGG TKLTVL (SEQ ID NO: 104) |
| CH-HAMF 5-1HBF | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSVGSGVSWSGYVATSIDAWGQGTLVT VSS (SEQ ID NO: 105) | SYELTQPPSVSVSPGQTARITCSAGSGLYGWYQ QKPGQAPVLVIYGTNKRPSGIPERFSGSSSGTT VTLTISGVQAEDEADYYCGSADSSTNAGIFGGG TKLTVL (SEQ ID NO: 106) |
| CH-HAMF 5-1HBG | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSMGSGVSWSGYVATSIDAWGQGTLVT VSS (SEQ ID NO: 107) | SYELTQPPSVSVSPGQTARITCSAGSGLYGWYQ QKPGQAPVLVIYGTNKRPSGIPERFSGSSSGTT VTLTISGVQAEDEADYYCGSADSSTNAGIFGGG TKLTVL (SEQ ID NO: 108) |
| CH-HAMF 5-1HFJ | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSMGSGVSWSGYVATSIDVWGQGTLVT VSS (SEQ ID NO: 109) | SYELTQPPSVSVSPGQTARITCSAGSGLYGWYQ QKPGQAPVLVIYGTNKRPSGIPERFSGSSSGTT VTLTISGVQAEDEADYYCGSADSSTNAGIFGGG TKLTVL (SEQ ID NO: 110) |
| CH-HAMF 5-MEP | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSVGSGVSWSGYVATSLDAWGQGTLVT VSS (SEQ ID NO: 111) | SYELTQPPSVSVSPGQTARITCSAGSGLYGWYQ QKPGQAPVLVIYGTNKRPSGIPERFSGSSSGTT VTLTISGVQAEDEADYYCGSADSSTNAGIFGGG TKLTVL (SEQ ID NO: 112) |
| CH-HAMF 5-1HFB | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSMGSGVSWSGYVATSIDAWGQGTLVT VSS (SEQ ID NO: 113) | SYELTQPPSVSVSPGQTARITCSGGSGSYGWYQ QKPGQAPVLVIYGTYKRPSGIPERFSGSSSGTT VTLTISGVQAEDEADYYCGSADSSTNAGIFGGG TKLTVL (SEQ ID NO: 114) |
| CH-HAMF 5-1HHR | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSMGSGVSWSGYVATSLDVWGQGTLVT VSS (SEQ ID NO: 115) | SYELTQPPSVSVSPGQTARITCSGGSGSYGWYQ QKPGQAPVLVIYGTYKRPSGIPERFSGSSSGTT VTLTISGVQAEDEADYYCGSADSSTNAGIFGGG TKLTVL (SEQ ID NO: 116) |
| CH-HAMF 5-1HHP | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSVGSGVSWSGYVATSLDVWGQGTLVT VSS (SEQ ID NO: 117) | SYELTQPPSVSVSPGQTARITCSGGSGSYGWYQ QKPGQAPVLVIYGTYKRPSGIPERFSGSSSGTT VTLTISGVQAEDEADYYCGSADSSTNAGIFGGG TKLTVL (SEQ ID NO: 118) |
| CH-HAMF 5-1HGT | EVQLLESGGGLVQPGGSLRLSCAASGFTFSS YAMNWVRQAPGKGLEWVAGISSSGRYTGYAD SVKGRFTISRDNSKNTLYLQMNSLRAEDTAV YYCAKSVGSGVSWSGYVATSLDVWGQGTLVT VSS (SEQ ID NO: 119) | SYELTQPPSVSVSPGQTARITCSAGSGLYGWYQ QKPGQAPVLVIYGTNKRPSGIPERFSGSSSGTT VTLTISGVQAEDEADYYCGSNDASTNAGIFGGG TKLTVL (SEQ ID NO: 120) |

-continued

| IM Ab ID | VH | VL |
|---|---|---|
| 35-N1F09-1HA | EVQLLESGGGLVQPGGSLRLSCAASGFTFSS YGMSWVRQAPGKGLEWVAGIGSSGIYTHYAD SVKGRFTISRDNSKNTLYLQMNSLRAEDTAV YYCAKSPGDSDWCGWAGYGIYSCRVAGFIDA WGQGTLVTVSS (SEQ ID NO: 121) | SYELTQPPSVSVSPGQTARITCSGGYNGHYGWY QQKPGQAPVLVIYGTNKRPSGIPERFSGSSSGT TVTLTISGVQAEDEADYYCGGYDSSAGIFGGGT KLTVL (SEQ ID NO: 122) |
| 35-N2H07-1HA | EVQLLESGGGLVQPGGSLRLSCAASGFTFSG YAMSWVRQAPGKGLEWVAGIYSSGSYTFYAD SVKGRFTISRDNSKNTLYLQMNSLRAEDTAV YYCAKGTGYCDWSGWCYSGAANIDAWGQGTL VTVSS (SEQ ID NO: 123) | SYELTQPPSVSVSPGQTARITCSGGSGSYGYYG WYQQKPGQAPVLVIYGTNKRPSGIPERFSGSSS GTTVTLTISGVQAEDEADYYCGSEDSSSGAGIF GGGTKLTVL (SEQ ID NO: 124) |

As provided herein, variants of any of the sequences described herein are also provided for. For example, in some embodiments, peptides that are at least, or about, 90%, 91%, 92%, 93%, 94%, 95%, 96%, 97%, 98%, or 99% are also provided. In some embodiments, the a protein comprising a sequence that is at least, or about, 60%, 70%, 80%, 85%, 90%, 91%, 92%, 93%, 94%, 95%, 96%, 97%, 98%, or 99% identical to such sequences disclosed herein are provided. In some embodiments, the sequences or variants have 1, 2, 3, 4, 5, 6, 7, 8, or 9 substitutions as compared to the sequences provided for herein. In some embodiments, the substitution is a conservative substitution. In some embodiments, the mutation or substitution is in the framework region of the light chain or the heavy chain. In some embodiments, the substitution is in the CDR regions, such as CDR1, CDR2, or CDR3. In some embodiments, the mutation or substitution is in CDR1 and not in CDR2 or CDR3. In some embodiments, the heavy chain comprises substitutions or changes in the framework region and not in the CDR regions as provided herein. In some embodiments, the heavy chain proteins are provided wherein the sequence is at least, or about 50%, 60%, 70%, 80%, 90%, 91%, 92%, 93%, 94%, 95%, 96%, 97%, 98%, or 99% identical to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, provided that the sequence comprises a first amino acid sequence or a first CDR selected from the group consisting of: SEQ ID NOs: 25, 31, 37, 43, 53, 55, 56, 62, 71, 76, 80, 90, 95, 139, 141, 143, or 145; a second amino acid sequence or second CDR selected from the group consisting of: 26, 32, 38, 44, 46, 48, 49, 54, 125, 72, 77, 81, 86, 91, 96, 101, 102, 140, 142, 144, or 146; and a third amino acid sequence or third CDR selected from the group consisting of: 27, 33, 39, 45, 57, 61, 63, 65, 66, 67, 126, 69, 73, 82, 57, 92, or 97. Thus, in some embodiments, the CDRs of the heavy chains are not variants of those provided herein.

In some embodiments, the antibody comprises a V$_H$ chain comprising the sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, or SEQ ID NO: 123, or a variant thereof.

In some embodiments, the light chain proteins are provided wherein the sequence is at least, or about 50%, 60%, 70%, 80%, 90%, 91%, 92%, 93%, 94%, 95%, 96%, 97%, 98%, or 99% identical to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, or SEQ ID NO: 124, provided that the sequence comprise a first amino acid sequence or a first CDR selected from the group consisting of: SEQ ID NOs: 22, 28, 34, 40, 47, 50, 58, 64, 74, 83, 87, 93, or 98; a second amino acid sequence or second CDR selected from the group consisting of: 23, 29, 41, 51, 59, 68, 84, 88, or 99; and a third amino acid sequence or third CDR selected from the group consisting of: 24, 30, 36, 42, 52, 60, 70, 75, 79, 85, 89, 94. Thus, in some embodiments, the CDRs of the heavy chains are not variants of those provided herein.

In some embodiments, the antibody comprises a V$_L$ chain comprising the sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, or SEQ ID NO: 124, or a variant thereof.

In some embodiments, the antibody comprises a V$_H$ and a V$_L$ chain comprising the sequence of SEQ ID NO: 2 and SEQ ID NO: 3, SEQ ID NO: 4 and SEQ ID NO: 5, SEQ ID NO: 6 and SEQ ID NO: 7, SEQ ID NO: 8 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 18 and SEQ ID NO: 19, SEQ ID NO: 20 and SEQ ID NO: 21, SEQ ID NO: 103 and SEQ ID NO: 104, SEQ ID NO: 105 and SEQ ID NO: 106, SEQ ID NO: 107 and SEQ ID NO: 108, SEQ ID NO: 109 and SEQ ID NO: 110, SEQ ID NO: 111 and SEQ ID NO: 112, SEQ ID NO: 113 and SEQ ID NO: 114, SEQ ID NO: 115 and SEQ ID NO: 116, SEQ ID NO: 117 and SEQ ID NO: 118, SEQ ID NO: 119 and SEQ ID NO: 120, SEQ ID NO: 121 and SEQ ID NO: 122, or SEQ ID NO: 123 and SEQ ID NO: 123.

In some embodiments, the sequence is at least 80, 85, 90, 91, 92, 93, 94, 95, 96, 97, 98, or 99% homologous or identical to the sequence provided herein, which includes the V$_H$, V$_L$, and/or CDR sequences provided for herein. The sequences can also be a variant if it has 1, 2, 3, 4, 5, 6, 7, 8, or 9 substitutions, deletions, or insertions. In some embodiments, the substitution (mutation) is a conservative substitution.

In some embodiments, the CDRs of the peptides or antibodies are as follows:

| ID# | LCDR1 | LCDR2 | LCDR3 | HCDR1 | HCDR2 | HCDR3 |
|---|---|---|---|---|---|---|
| 136 | CSGDSSWYGYG (SEQ ID NO: 22) | IYESGKRP (SEQ ID NO: 23) | CGSADSNSIGIF (SEQ ID NO: 24) | GFSFSSYDMGWV (SEQ ID NO: 25) | VASIYSSASSTYYA (SEQ ID NO: 26) | CAKAAGRTYRGWATYIADSIDA (SEQ ID NO: 27) |
| 171 | CSGGSSGYG (SEQ ID NO: 28) | IYSNDKRP (SEQ ID NO: 29) | CGSTDNSYVGIF (SEQ ID NO: 30) | GFDFSSYANINVVV (SEQ ID NO: 31) | VAGIGSTGSSTGYG (SEQ ID NO: 32) | CAKSVGNGNSWSGYIATSIDA (SEQ ID NO: 33) |
| 172 | CSGDSSDDGSYYYG (SEQ ID NO: 34) | IYSNDKRP (SEQ ID NO: 29) | CGSYDSSTGIF (SEQ ID NO: 36) | GFSISSYTMQWV (SEQ ID NO: 37) | VAGIYSGSRTYYG (SEQ ID NO: 38) | CAKSSYCTAWTGCDVYAGGSIDA (SEQ ID NO: 39) |
| 173 | CSGGNNYYG (SEQ ID NO: 40) | IYYNDKRP (SEQ ID NO: 41) | CGGWDSSGGIF (SEQ ID NO: 42) | GFTFSSYSMFWV (SEQ ID NO: 43) | VAGIDSGSTTFYG (SEQ ID NO: 44) | CAKDAYGYCGWSGCSADSIDA (SEQ ID NO: 45) |
| 179 | CSGDSSWYGYG (SEQ ID NO: 22) | IYESGKRP (SEQ ID NO: 23) | CGSADSNSIGIF (SEQ ID NO: 24) | GFSFSSYDMGWV (SEQ ID NO: 25) | VASIYSSASSTYYA (SEQ ID NO: 26) | CAKAAGRTYRGWATYIADSIDA (SEQ ID NO: 27) |
| 55 | CSGGSSGYG (SEQ ID NO: 28) | IYSNDKRP (SEQ ID NO: 29) | CGSTDNSYVGIF (SEQ ID NO: 30) | GFDFSSYANINVVV (SEQ ID NO: 31) | VAGIGSTGSSTGYA (SEQ ID NO: 46) | CAKSVGNGNSWSGYIATSIDA (SEQ ID NO: 33) |
| 181 | CSGDDGSYYYG (SEQ ID NO: 47) | IYSNDKRP (SEQ ID NO: 29) | CGSYDSSTGIF (SEQ ID NO: 36) | GFSISSYTMQWV (SEQ ID NO: 37) | VAGIYSGSRTYYA (SEQ ID NO: 48) | CAKSSYCTAWTGCDVYAGGSIDA (SEQ ID NO: 39) |
| 182 | CSGGNNYYG (SEQ ID NO: 40) | IYYNDKRP (SEQ ID NO: 41) | CGGWDSSGGIF (SEQ ID NO: 42) | GFTFSSYSMFWV (SEQ ID NO: 43) | VAGIDSGSTTFYA (SEQ ID NO: 49) | CAKDAYGYCGWSGCSADSIDA (SEQ ID NO: 45) |
| 271 | CSGGSGSYG (SEQ ID NO: 50) | IYGTNKRP (SEQ ID NO: 51) | CGSADSSTNAGIF (SEQ ID NO: 52) | GFTFSSYANISWV (SEQ ID NO: 53) | VAGISSSGRYTGYA (SEQ ID NO: 54) | CAKSVGNGNSWSGYIATSIDA (SEQ ID NO: 33) |
| 272 | CSGGSGSYG (SEQ ID NO: 50) | IYGTNKRP (SEQ ID NO: 51) | CGSADSSTNAGIF (SEQ ID NO: 52) | GFTFSSYAMNVVV (SEQ ID NO: 55) | VAGISSSGRYTGYA (SEQ ID NO: 54) | CAKSVGNGNSWSGYIATSIDA (SEQ ID NO: 33) |

In some embodiments, the CDRs of the peptides or antibodies are as follows:

| ID# | HCDR1 | HCDR2 | HCDR3 | LCDR1 | LCDR2 | LCDR3 |
|---|---|---|---|---|---|---|
| VH-CH-HAMF5-1HU | SYAMS (SEQ ID NO: 56) | GISSSGRYTGYADSVKG (SEQ ID NO: 125) | SVGNGNSWSGYIATSIDA (SEQ ID NO: 57) | SGGSGSYG (SEQ ID NO: 58) | GTNKRPS (SEQ ID NO: 59) | GSADSSTNAGI (SEQ ID NO: 60) |
| VH-CH-HAMF5-1HAQ | SYAMS (SEQ ID NO: 56) | GISSSGRYTGYADSVKG (SEQ ID NO: 125) | SVGNGNSWSGYVATSIDA (SEQ ID NO: 61) | SGGSGSYG (SEQ ID NO: 58) | GTNKRPS (SEQ ID NO: 59) | GSADSSTNAGI (SEQ ID NO: 60) |
| VH-CH-HAMF5-1HBF | SYAMN (SEQ ID NO: 62) | GISSSGRYTGYADSVKG (SEQ ID NO: 125) | SVGSGVSWSGYVATSIDA (SEQ ID NO: 63) | SAGSGLYG (SEQ ID NO: 64) | GTNKRPS (SEQ ID NO: 59) | GSADSSTNAGI (SEQ ID NO: 60) |
| VH-CH-HAMF5-1HBG | SYAMN (SEQ ID NO: 62) | GISSSGRYTGYADSVKG (SEQ ID NO: 125) | SMGSGVSWSGYVATSIDA (SEQ ID NO: 65) | SAGSGLYG (SEQ ID NO: 64) | GTNKRPS (SEQ ID NO: 59) | GSADSSTNAGI (SEQ ID NO: 60) |
| VH-CH-HAMF5-1HFJ | SYAMN (SEQ ID NO: 62) | GISSSGRYTGYADSVKG (SEQ ID NO: 125) | SMGSGVSWSGYVATSIDV (SEQ ID NO: 66) | SAGSGLYG (SEQ ID NO: 64) | GTNKRPS (SEQ ID NO: 59) | GSADSSTNAGI (SEQ ID NO: 60) |
| VH-CH-HAMF5-1HEP | SYAMN (SEQ ID NO: 62) | GISSSGRYTGYADSVKG (SEQ ID NO: 125) | SVGSGVSWSGYVATSLDA (SEQ ID NO: 67) | SAGSGLYG (SEQ ID NO: 64) | GTNKRPS (SEQ ID NO: 59) | GSADSSTNAGI (SEQ ID NO: 60) |
| VH-CH-HAMF5-1HFB | SYAMN (SEQ ID NO: 62) | GISSSGRYTGYADSVKG (SEQ ID NO: 125) | SMGSGVSWSGYVATSIDA (SEQ ID NO: 65) | SGGSGSYG (SEQ ID NO: 58) | GTYKRPS (SEQ ID NO: 68) | GSADSSTNAGI (SEQ ID NO: 60) |
| VH-CH-HAMF5-1HHR | SYAMN (SEQ ID NO: 62) | GISSSGRYTGYADSVKG (SEQ ID NO: 125) | SMGSGVSWSGYVATSLDV (SEQ ID NO: 126) | SGGSGSYG (SEQ ID NO: 58) | GTYKRPS (SEQ ID NO: 68) | GSADSSTNAGI (SEQ ID NO: 60) |
| VH-CH-HAMF5-1HHP | SYAMN (SEQ ID NO: 62) | GISSSGRYTGYADSVKG (SEQ ID NO: 125) | SVGSGVSWSGYVATSLDV (SEQ ID NO: 69) | SGGSGSYG (SEQ ID NO: 58) | GTYKRPS (SEQ ID NO: 68) | GSADSSTNAGI (SEQ ID NO: 60) |

| ID# | HCDR1 | HCDR2 | HCDR3 | LCDR1 | LCDR2 | LCDR3 |
|---|---|---|---|---|---|---|
| VH-CH-HAMF5-1HGT | SYAMN (SEQ ID NO: 62) | GISSSG RYTGYA DSVKG (SEQ ID NO: 125) | SVGSGV SWSGYV ATSLDV (SEQ ID NO: 69) | SAGSGL YG (SEQ ID NO: 64) | GTNKR PS (SEQ ID NO: 59) | GSNDAS TNAGI (SEQ ID NO: 70) |
| VH-35-N1F09-1HA | SYGMS (SEQ ID NO: 71) | GIGSSG IYTHYA DSVKG (SEQ ID NO: 72) | SPGDSD WCGWAG YGIYSC RVAGFI DA (SEQ ID NO: 73) | SGGYNG HYG (SEQ ID NO: 74) | GTNKR PS (SEQ ID NO: 59) | GGYDSS AGI (SEQ ID NO: 75) |
| VH-35-N2H07-1HA | GYAMS (SEQ ID NO: 76) | GIYSSG SYTFYA DSVKG (SEQ ID NO: 77) | GTGYCD WSGWCY SGAANI DA (SEQ ID NO: 78) | SGGSGS YG (SEQ ID NO: 58) | GTNKR PS (SEQ ID NO: 59) | GSEDSS SGAGI (SEQ ID NO: 79) |
| VH-30-08F12-1CA | SYDMG (SEQ ID NO: 80) | SIYSSA SSTYYA PAVKG (SEQ ID NO: 81) | AAGRTY RGWATY IADSID A (SEQ ID NO: 82) | SGDSSW YGYG (SEQ ID NO: 83) | ESGKR PS (SEQ ID NO: 84) | GSADSN SIGI (SEQ ID NO: 85) |
| VH-30-18G01-1CA | SYAMN (SEQ ID NO: 62) | GIGSTG SSTGYG PAVKG (SEQ ID NO: 86) | SVGNGN SWSGYI ATSIDA (SEQ ID NO: 57) | SGGSSG YG (SEQ ID NO: 87) | SNDKR PS (SEQ ID NO: 88) | GSTDNS YVGI (SEQ ID NO: 89) |
| VH-30-19B06-1CA | SYTMQ (SEQ ID NO: 90) | GIYSGS RTYYGA AVQG (SEQ ID NO: 91) | SSYCTA WTGCDV YAGGSI DA (SEQ ID NO: 92) | SGDSSD DGSYYY G (SEQ ID NO: 93) | SNDKR PS (SEQ ID NO: 88) | GSYDSS TGI (SEQ ID NO: 94) |
| VH-30-20D10-1CA | SYSMF (SEQ ID NO: 95) | GIDSGS TTFYGS AVKG (SEQ ID NO: 96) | DAYGYC GWSGCS ADSIDA (SEQ ID NO: 97) | SGGNNY YG (SEQ ID NO: 98) | YNDKR PS (SEQ ID NO: 99) | GGWDSS GGI (SEQ ID NO: 100) |
| VH-CHAMF5-1HQ | SYAMN (SEQ ID NO: 62) | GISSSG RYTGYA DSVKG (SEQ ID NO: 101) | SVGNGN SWSGYI ATSIDA (SEQ ID NO: 57) | SGGSGS YG (SEQ ID NO: 58) | GTNKR PS (SEQ ID NO: 59) | GSADSS TNAGI (SEQ ID NO: 60) |
| 30-18G01-1HA | SYAMN (SEQ ID NO: 62) | GIGSTG SSTGYA DSVKG (SEQ ID NO: 102) | SVGNGN SWSGYI ATSIDA (SEQ ID NO: 57) | SGGSSG YG (SEQ ID NO: 87) | PSNDK RS (SEQ ID NO: 88) | GSTDNS YVGI (SEQ ID NO: 89) |

In some embodiments, the $V_H$ chain comprises one or more CDRs selected from the tables provided herein or from the group consisting of: GFSFSSY (SEQ ID NO: 139); YSSASSTY (SEQ ID NO: 140); AAGRTYRGWATYIADSIDA (SEQ ID NO: 82); GFDFSSY (SEQ ID NO: 141); GSTGSS (SEQ ID NO: 142); SVGNGNSWSGYIATSIDA (SEQ ID NO: 57); GFSISSY (SEQ ID NO: 143); YSGSR (SEQ ID NO: 144); SSYCTAWTGCDVYAGGSIDA (SEQ ID NO: 92); GFTFSSY (SEQ ID NO: 145); DSGST (SEQ ID NO: 146); DAYGYCGWSGCSADSIDA (SEQ ID NO: 97); CSGDSSWYGYG (SEQ ID NO: 22); IYESGKRP (SEQ ID NO: 23); CGSADSNSIGIF (SEQ ID NO: 24); GFSFSSYDMGWV (SEQ ID NO: 25); VASIYSSASSTYYA (SEQ ID NO: 26); CAKAAGRTYRGWATYIADSIDA (SEQ ID NO: 27); CSGGSSGYG (SEQ ID NO: 28); IYSNDKRP (SEQ ID NO: 29); CGSTDNSYVGIF (SEQ ID NO: 30); GFDFSSYAMNWV (SEQ ID NO: 31); VAGIGSTGSSTGYG (SEQ ID NO: 32); CAKSVGNGNSWSGYIATSIDA (SEQ ID NO: 33); CSGDSSDDGSYYYG (SEQ ID NO: 34); IYSNDKRP (SEQ ID NO: 29); CGSYDSSTGIF (SEQ ID NO: 36); GFSISSYTMQWV (SEQ ID NO: 37); VAGIYSGSRTYYG (SEQ ID NO: 38); CAKSSYCTAWTGCDVYAGGSIDA (SEQ ID NO: 39); CSGGNNYYG (SEQ ID NO: 40); IYYNDKRP (SEQ ID NO: 41); CGGWDSSGGIF (SEQ ID NO: 42); GFTFSSYSMFWV (SEQ ID NO: 43); VAGIDSGSTTFYG (SEQ ID NO: 44); CAKDAYGYCGWSGCSADSIDA (SEQ ID NO: 45); CSGDSSWYGYG (SEQ ID NO: 22); IYESGKRP (SEQ ID NO: 23); CGSADSNSIGIF (SEQ ID NO: 24); GFSFSSYDMGWV (SEQ ID NO: 25); VASIYSSASSTYYA (SEQ ID NO: 26); CAKAAGRTYRGWATYIADSIDA (SEQ ID NO: 27); CSGGSSGYG (SEQ ID NO: 28); IYSNDKRP (SEQ ID NO: 29); CGSTDNSYVGIF (SEQ ID NO: 30); GFDFSSYAMNWV (SEQ ID NO: 31); VAGIGSTGSSTGYA (SEQ ID NO: 46); CAKSVGNGNSWSGYIATSIDA (SEQ ID NO: 33); CSGDDGSYYYG (SEQ ID NO: 47); IYSNDKRP (SEQ ID NO: 29); CGSYDSSTGIF (SEQ ID NO: 36); GFSISSYTMQWV (SEQ ID NO: 37); VAGIYSGSRTYYA (SEQ ID NO: 48); CAKSSYCTAWTGCDVYAGGSIDA (SEQ ID NO: 39); CSGGNNYYG (SEQ ID NO: 40); IYYNDKRP (SEQ ID NO: 41); CGGWDSSGGIF (SEQ ID NO: 42); GFTFSSYSMFWV (SEQ ID NO: 43); VAGIDSGSTTFYA (SEQ ID NO: 49); CAKDAYGYCGWSGCSADSIDA (SEQ ID NO: 45); CSGGSGSYG (SEQ ID NO: 50); IYGTNKRP (SEQ ID NO: 51); CGSADSSTNAGIF (SEQ ID NO: 52); GFTFSSYAMSWV (SEQ ID NO: 53); VAGISSSGRYTGYA (SEQ ID NO: 54); CAKSVGNGNSWSGYIATSIDA (SEQ ID NO: 33); CSGGSGSYG (SEQ ID NO: 50); IYGTNKRP (SEQ ID NO: 51); CGSADSSTNAGIF (SEQ ID NO: 52); GFTFSSYAMNWV (SEQ ID NO: 55); VAGISSSGRYTGYA (SEQ ID NO: 54); CAKSVGNGNSWSGYIATSIDA (SEQ ID NO: 33), SYAMS (SEQ ID NO: 56); GISSSGRYTGYADSVKG (SEQ ID NO: 101); SVGNGNSWSGYIATSIDA (SEQ ID NO: 57); SVGNGNSWSGYVATSIDA (SEQ ID NO: 61); SYAMN (SEQ ID NO: 62); SVGSGVSWSGYVATSIDA (SEQ ID NO: 63); GISSSGRYTGYADSVKG (SEQ ID NO: 101); SMGSGVSWSGYVATSIDA (SEQ ID NO: 65); SMGSGVSWSGYVATSIDV (SEQ ID NO: 66); SVGSGVSWSGYVATSLDA (SEQ ID NO: 67); SMGSGVSWSGYVATSIDA (SEQ ID NO: 65); SMGSGVSWSGYVATSLDV (SEQ ID NO: 126); SVGSGVSWSGYVATSLDV (SEQ ID NO: 69); SVGSGVSWSGYVATSLDV (SEQ ID NO: 69); SYGMS (SEQ ID NO: 71); GIGSSGIYTHYADSVKG (SEQ ID NO: 72); SPGDSDWCGWAGYGIYSCRVAGFIDA (SEQ ID NO: 73); GYAMS (SEQ ID NO: 76); GIYSSGSYTFYADSVKG (SEQ ID NO: 77); GTGYCDWSGWCYSGAANIDA (SEQ ID NO: 78); SYDMG (SEQ ID NO: 80); SIYSSASSTYYAPAVKG (SEQ ID NO: 81); AAGRTYRGWATYIADSIDA (SEQ ID NO: 82); GIGSTGSSTGYGPAVKG (SEQ ID NO: 86); SVGNGN SWSGYIATSIDA (SEQ ID NO: 57); SYTMQ (SEQ ID NO: 90); GIYSGSRTYYGAAVQG (SEQ ID NO: 91); SSYCTAWTGCDVYAGGSIDA (SEQ ID NO: 92); SYSMF (SEQ ID NO: 95); GIDSGSTTFYGSAVKG (SEQ ID NO: 96); DAYGYCGWSGCSADSIDA (SEQ ID NO: 97); GISSSGRYTGYADSVKG (SEQ ID NO: 101); SVGNGNSWSGYIATSIDA (SEQ ID NO: 57); GIGSTGSSTGYADSVKG (SEQ ID NO: 102); or SVGNGNSWSGYIATSIDA (SEQ ID NO: 57).

In some embodiments, the $V_H$ chain comprise the CDRs of:

1H.
```
                                           (SEQ ID NO: 139)
GFSFSSY;

(SEQ ID NO: 140)
YSSASSTY;
and (SEQ ID NO: 82)
AAGRTYRGWATYIADSIDA;
or
```

2H.
```
                                           (SEQ ID NO: 141)
GFDFSSY;

(SEQ ID NO: 142)
GSTGSS;
and (SEQ ID NO: 57)
SVGNGNSWSGYIATSIDA;
or
```

3H.
```
                                           (SEQ ID NO: 143)
GFSISSY;

(SEQ ID NO: 144)
YSGSR;
and (SEQ ID NO: 92)
SSYCTAWTGCDVYAGGSIDA;
or
```

4H.
```
                                           (SEQ ID NO: 145)
GFTFSSY;

(SEQ ID NO: 146)
DSGST;
and (SEQ ID NO: 97)
DAYGYCGWSGCSADSIDA;
or
```

5H.
```
                                           (SEQ ID NO: 25)
GFSFSSYDMGWV;

(SEQ ID NO: 26)
VASIYSSASSTYYA;
and (SEQ ID NO: 27)
CAKAAGRTYRGWATYIADSIDA;
or
```

6H.
```
                                           (SEQ ID NO: 31)
GFDFSSYAMNWV;

(SEQ ID NO: 32)
VAGIGSTGSSTGYG;
and (SEQ ID NO: 33)
CAKSVGNGNSWSGYIATSIDA;
or
```

7H.
```
                                           (SEQ ID NO: 37)
GFSISSYTMQWV;

(SEQ ID NO: 38)
VAGIYSGSRTYYG;
and (SEQ ID NO: 39)
CAKSSYCTAWTGCDVYAGGSIDA;
or
```

8H.
```
                                           (SEQ ID NO: 43)
GFTFSSYSMFWV;

(SEQ ID NO: 44)
VAGIDSGSTTFYG;
and (SEQ ID NO: 45)
CAKDAYGYCGWSGCSADSIDA;
or
```

9H.
```
                                           (SEQ ID NO: 25)
GFSFSSYDMGWV;

(SEQ ID NO: 26)
VASIYSSASSTYYA;
and (SEQ ID NO: 27)
CAKAAGRTYRGWATYIADSIDA;
or
```

10H.
```
                                           (SEQ ID NO: 31)
GFDFSSYAMNWV;

(SEQ ID NO: 46)
VAGIGSTGSSTGYA;
and (SEQ ID NO: 33)
CAKSVGNGNSWSGYIATSIDA;
or
```

11H.
```
                                           (SEQ ID NO: 37)
GFSISSYTMQWV;

(SEQ ID NO: 48)
VAGIYSGSRTYYA;
and (SEQ ID NO: 39)
CAKSSYCTAWTGCDVYAGGSIDA;
or
```

-continued 12H.
(SEQ ID NO: 43)
GFTFSSYSMFWV;

(SEQ ID NO: 49)
VAGIDSGSTTFYA;
and (SEQ ID NO: 45)
CAKDAYGYCGWSGCSADSIDA;
or 13H.
(SEQ ID NO: 53)
GFTFSSYAMSWV;

(SEQ ID NO: 54)
VAGISSSGRYTGYA;
and (SEQ ID NO: 33)
CAKSVGNGNSWSGYIATSIDA;
or 14H.
(SEQ ID NO: 55)
GFTFSSYAMNWV;

(SEQ ID NO: 54)
VAGISSSGRYTGYA;
and (SEQ ID NO: 33)
CAKSVGNGNSWSGYIATSIDA;
or 15H.
(SEQ ID NO: 56)
SYAMS;

(SEQ ID NO: 101)
GISSSGRYTGYADSVKG;
and (SEQ ID NO: 57)
SVGNGNSWSGYIATSIDA;
or 16H.
(SEQ ID NO: 56)
SYAMS;

(SEQ ID NO: 101)
GISSSGRYTGYADSVKG;
and (SEQ ID NO: 61)
SVGNGNSWSGYVATSIDA;
or 17H.
(SEQ ID NO: 62)
SYAMN;

(SEQ ID NO: 101)
GISSSGRYTGYADSVKG;
and (SEQ ID NO: 63)
SVGSGVSWSGYVATSIDA;
or

-continued 18H.
(SEQ ID NO: 62)
SYAMN;

(SEQ ID NO: 101)
GISSSGRYTGYADSVKG;
and (SEQ ID NO: 65)
SMGSGVSWSGYVATSIDA;
or 19H.
(SEQ ID NO: 62)
SYAMN;

(SEQ ID NO: 101)
GISSSGRYTGYADSVKG;
and (SEQ ID NO: 66)
SMGSGVSWSGYVATSIDV;
or 20H.
(SEQ ID NO: 62)
SYAMN;

(SEQ ID NO: 101)
GISSSGRYTGYADSVKG;
and (SEQ ID NO: 67)
SVGSGVSWSGYVATSLDA;
or 21H.
(SEQ ID NO: 62)
SYAMN;

(SEQ ID NO: 101)
GISSSGRYTGYADSVKG;
and (SEQ ID NO: 65)
SMGSGVSWSGYVATSIDA;
or 22H.
(SEQ ID NO: 62)
SYAMN;

(SEQ ID NO: 101)
GISSSGRYTGYADSVKG;
and (SEQ ID NO: 126)
SMGSGVSWSGYVATSLDV;
or 23H.
(SEQ ID NO: 62)
SYAMN;

(SEQ ID NO: 101)
GISSSGRYTGYADSVKG;
and (SEQ ID NO: 69)
SVGSGVSWSGYVATSLDV;
or

24H.

SYAMN; (SEQ ID NO: 62)

GISSSGRYTGYADSVKG; (SEQ ID NO: 101)
and

SVGSGVSWSGYVATSLDV; (SEQ ID NO: 69)
or

25H.

SYGMS; (SEQ ID NO: 71)

GIGSSGIYTHYADSVKG; (SEQ ID NO: 72)
and

SPGDSDWCGWAGYGIYSCRVAGFIDA; (SEQ ID NO: 73)
or

26H.

GYAMS; (SEQ ID NO: 76)

GIYSSGSYTFYADSVKG; (SEQ ID NO: 77)
and

GTGYCDWSGWCYSGAANIDA; (SEQ ID NO: 78)
or

27H.

SYDMG; (SEQ ID NO: 80)

SIYSSASSTYYAPAVKG; (SEQ ID NO: 81)
and

AAGRTYRGWATYIADSIDA; (SEQ ID NO: 82)
or

28H.

SYAMN; (SEQ ID NO: 62)

GIGSTGSSTGYGPAVKG; (SEQ ID NO: 86)
and

SVGNGNSWSGYIATSIDA; (SEQ ID NO: 57)
or

29H.

SYTMQ; (SEQ ID NO: 90)

GIYSGSRTYYGAAVQG; (SEQ ID NO: 91)
and

SSYCTAWTGCDVYAGGSIDA; (SEQ ID NO: 92)
or

30H.

SYSMF; (SEQ ID NO: 95)

GIDSGSTTFYGSAVKG; (SEQ ID NO: 96)
and

DAYGYCGWSGCSADSIDA; (SEQ ID NO: 97)
or

31H.

SYAMN; (SEQ ID NO: 62)

GISSSGRYTGYADSVKG; (SEQ ID NO: 101)
and

SVGNGNSWSGYIATSIDA; (SEQ ID NO: 57)
or

32H.

SYAMN; (SEQ ID NO: 62)

GIGSTGSSTGYADSVKG; (SEQ ID NO: 102)
and

SVGNGNSWSGYIATSIDA. (SEQ ID NO: 57)

In some embodiments, the antibody comprises a $V_L$ chain comprising the sequence of:

| IM Ab ID | $V_L$ |
|---|---|
| 136 | ALTQPSSVSANPGESVEITCSGDSSWYGYGWYQQKSPGSAPVTLIYESGKRPSDIPSRFSGSTSGSTATLTITGVQADDEAVYYCGSADSNSIGIFGAGTTLTVL (SEQ ID NO: 3) |
| 171 | ALTQPSSVSANLGGTVKLTCSGGSSGYGWYQQKSPGSAPVTVIYSNDKRPSDIPSRFSGSLSGSTGTLTITGVQADDEAVYFCGSTDNSYVGIFGAGTTLTVL (SEQ ID NO: 5) |
| 172 | ALTQPSSVSATPGGTVEITCSGDSSDDGSYYYGWYQQKSPGSAPVTVIYSNDKRPSSIPSRFSGSASGSTATLTITGVQADDEAVYFCGSYDSSTGIFGAGTTLTVL (SEQ ID NO: 7) |
| 173 | ALTQPSSVSANPGGTVEITCSGGNNYYGWYQQKSPGSAPVTVIYYNDKRPSDIPSRFSGSSKSGSTGTLTITGVQADDEAVYFCGGWDSSGGIFGAGTTLTVL (SEQ ID NO: 9) |
| 179 | SYELTQPPSVSVSPGQTARITCSGDSSWYGYGWYQQKPGQAPVLVIYESGKRPSGIPERFSGSSSGTTVTLTISGVQAEDEADYYCGSADSNSIGIFGGGTKLTVL (SEQ ID NO: 11) |
| 180 | SYELTQPPSVSVSPGQTARITCSGGSSGYGWYQQKPGQAPVLVIYSNDKRPSGIPERFSGSSSGTTVTLTISGVQAEDEADYYCGSTDNSYVGIFGGGTKLTVL (SEQ ID NO: 13) |
| 181 | SYELTQPPSVSVSPGQTARITCSGDDGSYYYGWYQQKPGQAPVLVIYSNDKRPSGIPERFSGSSSGTTVTLTISGVQAEDEADYYCGSYDSSTGIFGGGTKLTVL (SEQ ID NO: 15) |
| 182 | SYELTQPPSVSVSPGQTARITCSGGNNYYGWYQQKPGQAPVLVIYYNDKRPSGIPERFSGSSSGTTVTLTISGVQAEDEADYYCGGWDSSGGIFGGGTKLTVL (SEQ ID NO: 17) |
| 271 | SYELTQPPSVSVSPGQTARITCSGGSGSYGWYQQKPGQAPVLVIYGTNKRPSGIPERFSGSSSGTTVTLTISGVQAEDEADYYCGSADSSTNAGIFGGGTKLTVL (SEQ ID NO: 19) |

In some embodiments, the VL comprises a sequence of:

| IM Ab ID | V_L |
|---|---|
| 272 | SYELTQPPSVSVSPGQTARITCSGGSGSYGWYQQKPGQAPV TVIYGTNKRPSGIPERFSGSSSGTTVTLTISGVQAEDEADY YCGSADSSTNAGIFGGGTKLTVL (SEQ ID NO: 21) |
| CH-HAMF 5-1HAQ | SYELTQPPSVSVSPGQTARITCSGGSGSYGWYQQKPGQAPV LVIYGTNKRPSGIPERFSGSSSGTTVTLTISGVQAEDEADY YCGSADSSTNAGIFGGGTKLTVL (SEQ ID NO: 104) |
| CH-HAMF 5-1HBF | SYELTQPPSVSVSPGQTARITCSAGSGLYGWYQQKPGQAPV LVIYGTNKRPSGIPERFSGSSSGTTVTLTISGVQAEDEADY YCGSADSSTNAGIFGGGTKLTVL (SEQ ID NO: 106) |
| CH-HAMF 5-1HBG | SYELTQPPSVSVSPGQTARITCSAGSGLYGWYQQKPGQAPV LVIYGTNKRPSGIPERFSGSSSGTTVTLTISGVQAEDEADY YCGSADSSTNAGIFGGGTKLTVL (SEQ ID NO: 108) |
| CH-HAMF 5-1HFJ | SYELTQPPSVSVSPGQTARITCSAGSGLYGWYQQKPGQAPV LVIYGTNKRPSGIPERFSGSSSGTTVTLTISGVQAEDEADY YCGSADSSTNAGIFGGGTKLTVL (SEQ ID NO: 110) |
| CH-HAMF 5-1HEP | SYELTQPPSVSVSPGQTARITCSAGSGLYGWYQQKPGQAPV LVIYGTNKRPSGIPERFSGSSSGTTVTLTISGVQAEDEADY YCGSADSSTNAGIFGGGTKLTVL (SEQ ID NO: 112) |
| CH-HAMF 5-1HFB | SYELTQPPSVSVSPGQTARITCSGGSGSYGWYQQKPGQAPV LVIYGTYKRPSGIPERFSGSSSGTTVTLTISGVQAEDEADY YCGSADSSTNAGIFGGGTKLTVL (SEQ ID NO: 114) |
| CH-HAMF 5-1HHR | SYELTQPPSVSVSPGQTARITCSGGSGSYGWYQQKPGQAPV LVIYGTYKRPSGIPERFSGSSSGTTVTLTISGVQAEDEADY YCGSADSSTNAGIFGGGTKLTVL (SEQ ID NO: 116) |
| CH-HAMF 5-1HHP | SYELTQPPSVSVSPGQTARITCSGGSGSYGWYQQKPGQAPV LVIYGTYKRPSGIPERFSGSSSGTTVTLTISGVQAEDEADY YCGSADSSTNAGIFGGGTKLTVL (SEQ ID NO: 118) |
| CH-HAMF 5-1HGT | SYELTQPPSVSVSPGQTARITCSAGSGLYGWYQQKPGQAPV LVIYGTNKRPSGIPERFSGSSSGTTVTLTISGVQAEDEADY YCGSNDASTNAGIFGGGTKLTVL (SEQ ID NO: 120) |
| 35-N1F0 9-1HA | SYELTQPPSVSVSPGQTARITCSGGYNGHYGWYQQKPGQAP VLVIYGTNKRPSGIPERFSGSSSGTTVTLTISGVQAEDEAD YYCGGYDSSAGIFGGGTKLTVL (SEQ ID NO: 122) |
| 35-N2H0 7-1HA | SYELTQPPSVSVSPGQTARITCSGGSGSYGYYGWYQQKPGQ APVLVIYGTNKRPSGIPERFSGSSSGTTVTLTISGVQAEDE ADYYCGSEDSSSGAGIFGGGTKLTVL (SEQ ID NO: 124) |

In some embodiments, the VL comprises a sequence of:

| ID | V_L Sequence |
|---|---|
| F10-VL | ALTQPSSVSANPGETVKITCSGGYNGHYGWYQQKSPGSAPVT VIYSNNQRPSNIPSRFSGSTSGSTSTLTITGVRAEDEAVYFC GGYDSSAGIFGAGTTLTVL (SEQ ID NO: 127) |
| F10h-VL | SYELTQPPSVSVSPGQTARITCSGGYNGHYGWYQQKPGQAPV LVIYSNNQRPSGIPERFSGSSSGTTVTLTISGVQAEDEADYY CGGYDSSAGIFGGGTKLTVL (SEQ ID NO: 128) |
| B9-VL | ALTQPSSVSANPGETVKITCSGGGSSNYYGWYQQKSPGSAPV TLIYGTNKRPSDIPSRFSGSKSGSTGTLTITGVQADDEAVYF CGSADSSTNAGIFGAGTTLTVL (SEQ ID NO: 129) |
| B9h-VL | SYELTQPPSVSVSPGQTARITCSGGGSSNYAGWYGYYQQKPG QAPVTVIYGTNKRPSGIPERFSGSSSGTTVTLTISGVQAEDE AVYYCGSADSSTNAGIFGAGTKLTVL (SEQ ID NO: 130) |
| N6-G3 | SYELTQPPSVSVSPGQTARITCSGGSGSYGYYGWYQQKPGQA PVLVIYGTNKRPSGIPERFSGSSSGTTVTLTISGVQAEDEAD YYCGSTDSNYVGIFGGGTKLTVL (SEQ ID NO: 131) |
| N6-C5 | SYELTQPPSVSVSPGQTARITCSGGYNGHYGWYQQKPGQAPV LVIYSNNQRPSGIPERFSGSSSGTTVTLTISGVQAEDEADYY CGNADSNYVGIFGGGTKLTVL (SEQ ID NO: 132) |
| N6-F11 | SYELTQPPSVSVSPGQTARITCSGGGSSNYYGWYQQKPGQAP VLVIYSNNQRPSGIPERFSGSSSGTTVTLTISGVQAEDEADY YCGSADSSTNAGIFGGGTKLTVL (SEQ ID NO: 133) |
| N5-B4 | SYELTQPPSVSVSPGQTARITCSGGSGSYGYYGWYQQKPGQA PVLVIYSNNQRPSGIPERFSGSSSGTTVTLTISGVQAEDEAD YYCGSADSSTNAGIFGGGTKLTVL (SEQ ID NO: 134) |
| N5-B7 | SYELTQPPSVSVSPGQTARITCSGGSGSYGYYGWYQQKPGQA PVLVIYGTNKRPSGIPERFSGSSSGTTVTLTISGVQAEDEAD YYCGSADSSTNAGIFGGGTKLTVL (SEQ ID NO: 135) |

The VL sequence can comprise a $V_L$ sequence, CDR, CDR set or FW set, or any combination thereof as provided in PCT Application No PCT/US2020/018026, filed Feb. 13, 2020 and/or U.S. application Ser. No. 16/789,626, filed, Feb. 13, 2020, each of which is incorporated by reference in its entirety.

In some embodiments, any of the $V_H$ chains, or a $V_H$ chain comprising one or more (such as 3) CDRs, as provided for herein can be combined with any of the $V_L$ chains provided for herein. As demonstrated herein, the $V_L$ chains can be swapped and the antibodies can still bind to Claudin 6. In some embodiments, the $V_H$ is combined with one of F10-VL; 2. F10h-VL; 3. B9-VL; or B9h-VL.

In some embodiments, the sequence is at least 80, 85, 90, 95, 96, 97, 98, or 99% homologous or identical to the sequence provided herein, which includes the VH, VL, and CDR sequences. In some embodiments, the $V_L$ chain comprises one or more CDRs selected from the group consisting of: SGDSSWYGYG (SEQ ID NO: 83); ESGKRPS (SEQ ID NO: 84); GSADSNSIGI (SEQ ID NO: 85); SGGSSGYG (SEQ ID NO: 87); SNDKRPS (SEQ ID NO: 88); GSTDNSYVGI (SEQ ID NO: 89); SGDSSDDGSYYYG (SEQ ID NO: 93); SNDKRPS (SEQ ID NO: 88); GSYDSSTGI (SEQ ID NO: 94); SGGNNYYG (SEQ ID NO: 98); YNDKRPS (SEQ ID NO: 99); GGWDSSGGI (SEQ ID NO: 100), CSGDSSWYGYG (SEQ ID NO: 22); IYESGKRP (SEQ ID NO: 23); CGSADSNSIGIF (SEQ ID NO: 24); CSGGSSGYG (SEQ ID NO: 28); IYSNDKRP (SEQ ID NO: 29); CGSTDNSYVGIF (SEQ ID NO: 30); CSGDSSDDGSYYYG (SEQ ID NO: 34); IYSNDKRP (SEQ ID NO: 29); CGSYDSSTGIF (SEQ ID NO: 36); CSGGNNYYG (SEQ ID NO: 40); IYYNDKRP (SEQ ID NO: 41); CGGWDSSGGIF (SEQ ID NO: 42); CSGDSSWYGYG (SEQ ID NO: 22); IYESGKRP (SEQ ID NO: 23); CGSADSNSIGIF (SEQ ID NO: 24); CSGGSSGYG (SEQ ID NO: 28); IYSNDKRP (SEQ ID NO: 29); CGSTDNSYVGIF (SEQ ID NO: 30); CSGDDGSYYYG (SEQ ID NO: 47); IYSNDKRP (SEQ ID NO: 29); CGSYDSSTGIF (SEQ ID NO: 36); CSGGNNYYG (SEQ ID NO: 40); IYYNDKRP (SEQ ID NO: 41); CGGWDSSGGIF (SEQ ID NO: 42); CSGGSGSYG (SEQ ID NO: 50); IYGTNKRP (SEQ ID NO: 51); CGSADSSTNAGIF (SEQ ID NO: 52); CSGGSGSYG (SEQ ID NO: 50); IYGTNKRP (SEQ ID NO: 51); and CGSADSSTNAGIF (SEQ ID NO: 52); SGGSGSYG (SEQ ID NO: 58); GTNKRPS (SEQ ID NO: 59); GSADSSTNAGI (SEQ ID NO: 60); SAGSGLYG (SEQ ID NO: 64); GTYKRPS (SEQ ID NO: 68); GSNDASTNAGI (SEQ ID NO: 70); SGGYNGHYG (SEQ ID NO: 74); GGYDSSAGI (SEQ ID NO: 75); SGGSGSYGYYG (SEQ ID NO: 147); or GSEDSSSGAGI (SEQ ID NO: 79).

In some embodiments, the $V_L$ chain comprises the CDRs of:

1L.
```
                                      (SEQ ID NO: 83)
SGDSSWYGYG;

(SEQ ID NO: 84)
ESGKRPS;
and (SEQ ID NO: 85)
GSADSNSIGI;
or
```

2L.
```
                                      (SEQ ID NO: 87)
SGGSSGYG;

(SEQ ID NO: 88)
SNDKRPS;
and (SEQ ID NO: 89)
GSTDNSYVGI;
or
```

3L.
```
                                      (SEQ ID NO: 93)
SGDSSDDGSYYYG;

(SEQ ID NO: 88)
SNDKRPS;
and (SEQ ID NO: 94)
GSYDSSTGI;
or
```

4L.
```
                                      (SEQ ID NO: 98)
SGGNNYYG;

(SEQ ID NO: 99)
YNDKRPS;
and (SEQ ID NO: 100)
GGWDSSGGI;
or
```

5L.
```
                                      (SEQ ID NO: 22)
CSGDSSWYGYG;

(SEQ ID NO: 23)
IYESGKRP;
and (SEQ ID NO: 24)
CGSADSNSIGIF;
or
```

6L.
```
                                      (SEQ ID NO: 28)
CSGGSSGYG;

(SEQ ID NO: 29)
IYSNDKRP;
and (SEQ ID NO: 30)
CGSTDNSYVGIF;
or
```

7L.
```
                                      (SEQ ID NO: 34)
CSGDSSDDGSYYYG;

(SEQ ID NO: 29)
IYSNDKRP;
and (SEQ ID NO: 36)
CGSYDSSTGIF;
or
```

8L.
```
                                      (SEQ ID NO: 40)
CSGGNNYYG;

(SEQ ID NO: 41)
IYYNDKRP;
and (SEQ ID NO: 42)
CGGWDSSGGIF;
or
```

9L.
```
                                      (SEQ ID NO: 22)
CSGDSSWYGYG;

(SEQ ID NO: 23)
IYESGKRP;
and (SEQ ID NO: 24)
CGSADSNSIGIF;
or
```

10L.
```
                                      (SEQ ID NO: 28)
CSGGSSGYG;

(SEQ ID NO: 29)
IYSNDKRP;
and (SEQ ID NO: 30)
CGSTDNSYVGIF;
or
```

11L.
```
                                      (SEQ ID NO: 47)
CSGDDGSYYYG;

(SEQ ID NO: 29)
IYSNDKRP;
and (SEQ ID NO: 36)
CGSYDSSTGIF;
or
```

12L.
```
                                      (SEQ ID NO: 40)
CSGGNNYYG;

(SEQ ID NO: 41)
IYYNDKRP;
and (SEQ ID NO: 42)
CGGWDSSGGIF;
or
```

13L.

CSGGSGSYG; (SEQ ID NO: 50)

IYGTNKRP; (SEQ ID NO: 51)
and

CGSADSSTNAGIF; (SEQ ID NO: 52)
or

14L.

CSGGSGSYG; (SEQ ID NO: 50)

IYGTNKRP; (SEQ ID NO: 51)
and

CGSADSSTNAGIF; (SEQ ID NO: 52)
or

15L.

SGGSGSYG; (SEQ ID NO: 58)

GTNKRPS; (SEQ ID NO: 59)
and

GSADSSTNAGI; (SEQ ID NO: 60)
or

16L.

SGGSGSYG; (SEQ ID NO: 58)

GTNKRPS; (SEQ ID NO: 59)
and

GSADSSTNAGI; (SEQ ID NO: 60)
or

17L.

SAGSGLYG; (SEQ ID NO: 64)

GTNKRPS; (SEQ ID NO: 59)
and

GSADSSTNAGI; (SEQ ID NO: 60)
or

18L.

SAGSGLYG; (SEQ ID NO: 64)

GTNKRPS; (SEQ ID NO: 59)
and

GSADSSTNAGI; (SEQ ID NO: 60)
or

19L.

SAGSGLYG; (SEQ ID NO: 64)

GTNKRPS; (SEQ ID NO: 59)
and

GSADSSTNAGI; (SEQ ID NO: 60)
or

20L.

SAGSGLYG; (SEQ ID NO: 64)

GTNKRPS; (SEQ ID NO: 59)
and

GSADSSTNAGI; (SEQ ID NO: 60)
or

21L.

SGGSGSYG; (SEQ ID NO: 58)

GTYKRPS; (SEQ ID NO: 68)
and

GSADSSTNAGI; (SEQ ID NO: 60)
or

22L.

SGGSGSYG; (SEQ ID NO: 58)

GTYKRPS; (SEQ ID NO: 68)
and

GSADSSTNAGI; (SEQ ID NO: 60)
or

23L.

SGGSGSYG; (SEQ ID NO: 58)

GTYKRPS; (SEQ ID NO: 68)
and

GSADSSTNAGI; (SEQ ID NO: 60)
or

24L.

SAGSGLYG; (SEQ ID NO: 64)

GTNKRPS; (SEQ ID NO: 59)
and

GSNDASTNAGI; (SEQ ID NO: 70)
or

25L.

SGGYNGHYG; (SEQ ID NO: 74)

GTNKRPS; (SEQ ID NO: 59)
and

GGYDSSAGI; (SEQ ID NO: 75)
or

26L.

SGGSGSYGYYG; (SEQ ID NO: 59)
GTNKRPS;
and

GSEDSSSGAGI; (SEQ ID NO: 79)
or

27L.

SGDSSWYGYG; (SEQ ID NO: 83)

ESGKRPS; (SEQ ID NO: 84)
and

GSADSNSIGI; (SEQ ID NO: 85)
or

28L.

SGGSSGYG; (SEQ ID NO: 87)

SNDKRPS; (SEQ ID NO: 88)
and

GSTDNSYVGI; (SEQ ID NO: 89)
or

29L.

SGDSSDDGSYYYG; (SEQ ID NO: 93)

SNDKRPS; (SEQ ID NO: 88)
and

GSYDSSTGI; (SEQ ID NO: 94)
or

30L.

SGGNNYYG; (SEQ ID NO: 98)

YNDKRPS; (SEQ ID NO: 99)
and

GGWDSSGGI; (SEQ ID NO: 100)
or

31L.

SGGSGSYG; (SEQ ID NO: 58)

GTNKRPS; (SEQ ID NO: 59)
and

GSADSSTNAGI; (SEQ ID NO: 60)
or

32L.

SGGSSGYG; (SEQ ID NO: 87)

SNDKRPS; (SEQ ID NO: 88)
and

GSTDNSYVGI. (SEQ ID NO: 89)

In some embodiments, the antibody comprises the CDRs of 1H and 1L, 1H and 2L, 1H and 3L, 1H and 4L, 1H and 5L, 1H and 6L, 1H and 7L, 1H and 8L, 1H and 9L, 1H and 10L, 1H and 11L, 1H and 12L, 1H and 13L, 1H and 14L, 1H and 15L, 1H and 16L, 1H and 17L, 1H and 18L, 1H and 19L, 1H and 20L, 1H and 21L, 1H and 22L, 1H and 23L, 1H and 24L, 1H and 25L, 1H and 26L, 1H and 27L, 1H and 28L, 1H and 29L, 1H and 30L, 1H and 31L, 1H and 32L, 2H and 1L, 2H and 2L, 2H and 3L, 2H and 4L, 2H and 5L, 2H and 6L, 2H and 7L, 2H and 8L, 2H and 9L, 2H and 10L, 2H and 11L, 2H and 12L, 2H and 13L, 2H and 14L, 2H and 15L, 2H and 16L, 2H and 17L, 2H and 18L, 2H and 19L, 2H and 20L, 2H and 21L, 2H and 22L, 2H and 23L, 2H and 24L, 2H and 25L, 2H and 26L, 2H and 27L, 2H and 28L, 2H and 29L, 2H and 30L, 2H and 31L, 2H and 32L, 3H and 1L, 3H and 2L, 3H and 3L, 3H and 4L, 3H and 5L, 3H and 6L, 3H and 7L, 3H and 8L, 3H and 9L, 3H and 10L, 3H and 11L, 3H and 12L, 3H and 13L, 3H and 14L, 3H and 15L, 3H and 16L, 3H and 17L, 3H and 18L, 3H and 19L, 3H and 20L, 3H and 21L, 3H and 22L, 3H and 23L, 3H and 24L, 3H and 25L, 3H and 26L, 3H and 27L, 3H and 28L, 3H and 29L, 3H and 30L, 3H and 31L, 3H and 32L, 4H and 1L, 4H and 2L, 4H and 3L, 4H and 4L, 4H and 5L, 4H and 6L, 4H and 7L, 4H and 8L, 4H and 9L, 4H and 10L, 4H and 11L, 4H and 12L, 4H and 13L, 4H and 14L, 4H and 15L, 4H and 16L, 4H and 17L, 4H and 18L, 4H and 19L, 4H and 20L, 4H and 21L, 4H and 22L, 4H and 23L, 4H and 24L, 4H and 25L, 4H and 26L, 4H and 27L, 4H and 28L, 4H and 29L, 4H and 30L, 4H and 31L, 4H and 32L, 5H and 1L, 5H and 2L, 5H and 3L, 5H and 4L, 5H and 5L, 5H and 6L, 5H and 7L, 5H and 8L, 5H and 9L, 5H and 10L, 5H and 11L, 5H and 12L, 5H and 13L, 5H and 14L, 5H and 15L, 5H and 16L, 5H and 17L, 5H and 18L, 5H and 19L, 5H and 20L, 5H and 21L, 5H and 22L, 5H and 23L, 5H and 24L, 5H and 25L, 5H and 26L, 5H and 27L, 5H and 28L, 5H and 29L, 5H and 30L, 5H and 31L, 5H and 32L, 6H and 1L, 6H and 2L, 6H and 3L, 6H and 4L, 6H and 5L, 6H and 6L, 6H and 7L, 6H and 8L, 6H and 9L, 6H and 10L, 6H and 11L, 6H and 12L, 6H and 13L, 6H and 14L, 6H and 15L, 6H and 16L, 6H and 17L, 6H and 18L, 6H and 19L, 6H and 20L, 6H and 21L, 6H and 22L, 6H and 23L, 6H and 24L, 6H and 25L, 6H and 26L, 6H and 27L, 6H and 28L, 6H and 29L, 6H and 30L, 6H and 31L, 6H and 32L, 7H and 1L, 7H and 2L, 7H and 3L, 7H and 4L, 7H and 5L, 7H and 6L, 7H and 7L, 7H and 8L, 7H and 9L, 7H and 10L, 7H and 11L, 7H and 12L, 7H and 13L, 7H and 14L, 7H and 15L, 7H and 16L, 7H and 17L, 7H and 18L, 7H and 19L, 7H and 20L, 7H and 21L, 7H and 22L, 7H and 23L, 7H and 24L, 7H and 25L, 7H and 26L, 7H and 27L, 7H and 28L, 7H and 29L, 7H and 30L, 7H and 31L, 7H and 32L, 8H and 1L, 8H and 2L, 8H and 3L, 8H and 4L, 8H and 5L, 8H and 6L, 8H and 7L, 8H and 8L, 8H and 9L, 8H and 10L, 8H and 11L, 8H and 12L, 8H and 13L, 8H and 14L, 8H and 15L, 8H and 16L, 8H and 17L, 8H and 18L, 8H and 19L, 8H and 20L, 8H and 21L, 8H and 22L, 8H and 23L, 8H and 24L, 8H and 25L, 8H and 26L, 8H and 27L, 8H and 28L, 8H and 29L, 8H and 30L, 8H and 31L, 8H and 32L, 9H and 1L, 9H and 2L, 9H and 3L, 9H and 4L, 9H and 5L, 9H and 6L, 9H and 7L, 9H and 8L, 9H and 9L, 9H and 10L, 9H and 11L, 9H and 12L, 9H and 13L, 9H and 14L, 9H and 15L, 9H and 16L, 9H and 17L, 9H and 18L, 9H and 19L, 9H and 20L, 9H and 21L, 9H and 22L, 9H and 23L, 9H and 24L, 9H and 25L, 9H and 26L, 9H and 27L, 9H and 28L, 9H and 29L, 9H and 30L, 9H and 31L, 9H and 32L, 10H and 1L, 10H and 2L, 10H and 3L, 10H and 4L, 10H and 5L, 10H and 6L, 10H and 7L, 10H and 8L, 10H and 9L, 10H and 10L, 10H and 11L, 10H and 12L, 10H and 13L, 10H and 14L, 10H and 15L, 10H and 16L, 10H and 17L, 10H and 18L, 10H and 19L, 10H and 20L, 10H and 21L, 10H and 22L, 10H and 23L, 10H and 24L, 10H and 25L, 10H and 26L, 10H and 27L, 10H and 28L, 10H and 29L, 10H and 30L, 10H and 31L, 10H and 32L, 11H and 1L, 11H and 2L, 11H and 3L, 11H and 4L, 11H and 5L, 11H and 6L, 11H and 7L, 11H and 8L, 11H and 9L, 11H and 10L, 11H and 11L, 11H and 12L, 11H and 13L, 11H and 14L, 11H and 15L, 11H and 16L, 11H and 17L, 11H and 18L, 11H and 19L, 11H and 20L, 11H and 21L, 11H and 22L, 11H and 23L, 11H and 24L, 11H and 25L, 11H and 26L, 11H and 27L, 11H and 28L, 11H and 29L, 11H and 30L, 11H and 31L, 11H and 32L, 12H and 1L, 12H and 2L, 12H and 3L, 12H and 4L, 12H and 5L, 12H and 6L, 12H and 7L, 12H and 8L, 12H and 9L, 12H and 10L, 12H and 11L, 12H and 12L, 12H and 13L, 12H and 14L, 12H and 15L, 12H and 16L, 12H and 17L, 12H and 18L, 12H and 19L, 12H and 20L, 12H and 21L, 12H and 22L, 12H and 23L, 12H and 24L, 12H and 25L, 12H and 26L, 12H and 27L, 12H and 28L, 12H and 29L, 12H and 30L, 12H and 31L, 12H and 32L, 13H and 1L, 13H and 2L, 13H and 3L, 13H and 4L, 13H and 5L, 13H and 6L, 13H and 7L, 13H and 8L, 13H and 9L, 13H and 10L, 13H and 11L, 13H and 12L, 13H and 13L, 13H and 14L, 13H and 15L, 13H and 16L, 13H and 17L, 13H and 18L, 13H and 19L, 13H and 20L, 13H and 21L, 13H and 22L, 13H and 23L, 13H and 24L, 13H and 25L, 13H and 26L, 13H and 27L, 13H and 28L, 13H and 29L, 13H and 30L, 13H and 31L, 13H and 32L, 14H and 1L, 14H and 2L, 14H and 3L, 14H and 4L, 14H and 5L, 14H and 6L, 14H and 7L, 14H and 8L, 14H and 9L, 14H and 10L, 14H and 11L, 14H and 12L, 14H and 13L, 14H and 14L, 14H and 15L, 14H and 16L, 14H and 17L, 14H and 18L, 14H and 19L, 14H and 20L, 14H and 21L, 14H and 22L, 14H and 23L, 14H and 24L, 14H and 25L, 14H and 26L, 14H and 27L, 14H and 28L, 14H and 29L, 14H and 30L, 14H and 31L, 14H and 32L, 15H and 1L, 15H and 2L, 15H and 3L, 15H and 4L, 15H and 5L, 15H and 6L, 15H and 7L, 15H and 8L, 15H and 9L, 15H and 10L, 15H and 11L, 15H and 12L, 15H and 13L, 15H and 14L, 15H and 15L, 15H and 16L, 15H and 17L, 15H and 18L, 15H and 19L, 15H and 20L, 15H and 21L, 15H and 22L, 15H and 23L, 15H and 24L, 15H and 25L, 15H and 26L, 15H and 27L, 15H and 28L, 15H and 29L, 15H and 30L, 15H and 31L, 15H and 32L, 16H and 1L, 16H and 2L, 16H and 3L, 16H and 4L, 16H and 5L, 16H and 6L, 16H and 7L, 16H and 8L, 16H and 9L, 16H and 10L, 16H and 11L, 16H and 12L, 16H and 13L, 16H and 14L, 16H and 15L, 16H and 16L, 16H and 17L, 16H and 18L, 16H and 19L, 16H and 20L, 16H and 21L, 16H and 22L, 16H and 23L, 16H and 24L, 16H and 25L, 16H and 26L, 16H and 27L, 16H and 28L, 16H and 29L, 16H and 30L, 16H and 31L, 16H and 32L, 17H and 1L, 17H and 2L, 17H and 3L, 17H and 4L, 17H and 5L, 17H and 6L, 17H and 7L, 17H and 8L, 17H and 9L, 17H and 10L, 17H and 11L, 17H and 12L, 17H and 13L, 17H and 14L, 17H and 15L, 17H and 16L, 17H and 17L, 17H and 18L, 17H and 19L, 17H and 20L, 17H and 21L, 17H and 22L, 17H and 23L, 17H and 24L, 17H and 25L, 17H and 26L, 17H and 27L, 17H and 28L, 17H and 29L, 17H and 30L, 17H and 31L, 17H and 32L, 18H and 1L, 18H and 2L, 18H and 3L, 18H and 4L, 18H and 5L, 18H and 6L, 18H and 7L, 18H and 8L, 18H and 9L, 18H and 10L, 18H and 11L, 18H and 12L, 18H and 13L, 18H and 14L, 18H and 15L, 18H and 16L, 18H and 17L, 18H and 18L, 18H and 19L, 18H and 20L, 18H and 21L, 18H and 22L, 18H and 23L, 18H and 24L, 18H and 25L, 18H and 26L, 18H and 27L, 18H and 28L, 18H and 29L, 18H and 30L, 18H and 31L, 18H and 32L, 19H and 1L, 19H and 2L, 19H and 3L, 19H and 4L, 19H and 5L, 19H and 6L, 19H and 7L, 19H and 8L, 19H and 9L, 19H and 10L, 19H and 11L, 19H and 12L, 19H and 13L, 19H and 14L, 19H and 15L, 19H and 16L, 19H and 17L, 19H and 18L, 19H and 19L, 19H and 20L, 19H and 21L, 19H and 22L, 19H and 23L, 19H and 24L, 19H and 25L, 19H and 26L, 19H and 27L, 19H and 28L, 19H and 29L, 19H and 30L, 19H and 31L, 19H and 32L, 20H and 1L, 20H and 2L, 20H and 3L, 20H and 4L, 20H and 5L, 20H and 6L, 20H and 7L, 20H and 8L, 20H and 9L, 20H and 10L, 20H and 11L, 20H and 12L, 20H and 13L, 20H and 14L, 20H and 15L, 20H and 16L, 20H and 17L, 20H and 18L, 20H and 19L, 20H and 20L, 20H and 21L, 20H and 22L, 20H and 23L, 20H and 24L, 20H and 25L, 20H and 26L, 20H and 27L, 20H and 28L, 20H and 29L, 20H and 30L, 20H and 31L, 20H and 32L, 21H and 1L, 21H and 2L, 21H and 3L, 21H and 4L, 21H and 5L, 21H and 6L, 21H and 7L, 21H and 8L, 21H and 9L, 21H and 10L, 21H and 11L, 21H and 12L, 21H and 13L, 21H and 14L, 21H and 15L, 21H and 16L, 21H and 17L, 21H and 18L, 21H and 19L, 21H and 20L, 21H and 21L, 21H and 22L, 21H and 23L, 21H and 24L, 21H and 25L, 21H and 26L, 21H and 27L, 21H and 28L, 21H and 29L, 21H and 30L, 21H and 31L, 21H and 32L, 22H and 1L, 22H and 2L, 22H and 3L, 22H and 4L, 22H and 5L, 22H and 6L, 22H and 7L, 22H and 8L, 22H and 9L, 22H and 10L, 22H and 11L, 22H and 12L, 22H and 13L, 22H and 14L, 22H and 15L, 22H and 16L, 22H and 17L, 22H and 18L, 22H and 19L, 22H and 20L, 22H and 21L, 22H and 22L, 22H and 23L, 22H and 24L, 22H and 25L, 22H and 26L, 22H and 27L, 22H and 28L, 22H and 29L, 22H and 30L, 22H and 31L, 22H and 32L, 23H and 1L, 23H and 2L, 23H and 3L, 23H and 4L, 23H and 5L, 23H and 6L, 23H and 7L, 23H and 8L, 23H and 9L, 23H and 10L, 23H and 11L, 23H and 12L, 23H and 13L, 23H and 14L, 23H and 15L, 23H and 16L, 23H and 17L, 23H and 18L, 23H and 19L, 23H and 20L, 23H and 21L, 23H and 22L, 23H and 23L, 23H and 24L, 23H and 25L, 23H and 26L, 23H and 27L, 23H and 28L, 23H and 29L, 23H and 30L, 23H and 31L, 23H and 32L, 24H and 1L, 24H and 2L, 24H and 3L, 24H and 4L, 24H and 5L, 24H and 6L, 24H and 7L, 24H and 8L, 24H and 9L, 24H and 10L, 24H and 11L, 24H and 12L, 24H and 13L, 24H and 14L, 24H and 15L, 24H and 16L, 24H and 17L, 24H and 18L, 24H and 19L, 24H and 20L, 24H and 21L, 24H and 22L, 24H and 23L, 24H and 24L, 24H and 25L, 24H and 26L, 24H and 27L, 24H and 28L, 24H and 29L, 24H and 30L, 24H and 31L, 24H and 32L, 25H and 1L, 25H and 2L, 25H and 3L, 25H and 4L, 25H and 5L, 25H and 6L, 25H and 7L, 25H and 8L, 25H and 9L, 25H and 10L, 25H and 11L, 25H and 12L, 25H and 13L, 25H and 14L, 25H and 15L, 25H and 16L, 25H and 17L, 25H and 18L, 25H and 19L, 25H and 20L, 25H and 21L, 25H and 22L, 25H and 23L, 25H and 24L, 25H and 25L, 25H and 26L, 25H and 27L, 25H and 28L, 25H and 29L, 25H and 30L, 25H and 31L, 25H and 32L, 26H and 1L, 26H and 2L, 26H and 3L, 26H and 4L, 26H and 5L, 26H and 6L, 26H and 7L, 26H and 8L, 26H and 9L, 26H and 10L, 26H and 11L, 26H and 12L, 26H and 13L, 26H and 14L, 26H and 15L, 26H and 16L, 26H and 17L, 26H and 18L, 26H and 19L, 26H and 20L, 26H and 21L, 26H and 22L, 26H and 23L, 26H and 24L, 26H and 25L, 26H and 26L, 26H and 27L, 26H and 28L, 26H and 29L, 26H and 30L, 26H and 31L, 26H and 32L, 27H and 1L, 27H and 2L, 27H and 3L, 27H and 4L, 27H and 5L, 27H and 6L, 27H and 7L, 27H and 8L, 27H and 9L, 27H and 10L, 27H and 11L, 27H and 12L, 27H and 13L, 27H and 14L, 27H and 15L, 27H and 16L, 27H and 17L, 27H and 18L, 27H and 19L, 27H and 20L, 27H and 21L, 27H and 22L, 27H and 23L, 27H and 24L, 27H and 25L, 27H and 26L, 27H and 27L, 27H and 28L, 27H and 29L, 27H and 30L, 27H and 31L, 27H and 32L, 28H and 1L, 28H and 2L, 28H and 3L, 28H and 4L, 28H and 5L, 28H and 6L, 28H and 7L, 28H and 8L, 28H and 9L, 28H and 10L, 28H and 11L, 28H and 12L, 28H and 13L, 28H and 14L, 28H and 15L, 28H and 16L, 28H and 17L, 28H and 18L, 28H and 19L, 28H and 20L, 28H and 21L, 28H and 22L, 28H and 23L, 28H and 24L, 28H and 25L, 28H and 26L, 28H and 27L, 28H and 28L, 28H and 29L, 28H and 30L, 28H and 31L, 28H and 32L, 29H and 1L, 29H and 2L, 29H and 3L, 29H and 4L, 29H and 5L, 29H and 6L, 29H and 7L, 29H and 8L, 29H and 9L, 29H and 10L, 29H and 11L, 29H and 12L, 29H and 13L, 29H and 14L, 29H and 15L, 29H and 16L, 29H and 17L, 29H and 18L, 29H and 19L, 29H and 20L, 29H and 21L, 29H and 22L, 29H and 23L, 29H and 24L, 29H and 25L, 29H and 26L, 29H and 27L, 29H and 28L, 29H and 29L, 29H and 30L, 29H and 31L, 29H and 32L, 30H and 1L, 30H and 2L, 30H and 3L, 30H and 4L, 30H and 5L, 30H and 6L, 30H and 7L, 30H and 8L, 30H and 9L, 30H and 10L, 30H and 11L, 30H and 12L, 30H and 13L, 30H and 14L, 30H and 15L, 30H and 16L, 30H and 17L, 30H and 18L, 30H and 19L, 30H and 20L, 30H and 21L, 30H and 22L, 30H and 23L, 30H and 24L, 30H and 25L, 30H and 26L, 30H and 27L, 30H and 28L, 30H and 29L, 30H and 30L, 30H and 31L, 30H and 32L, 31H and 1L, 31H and 2L, 31H and 3L, 31H and 4L, 31H and 5L, 31H and 6L, 31H and 7L, 31H and 8L, 31H and 9L, 31H and 10L, 31H and 11L, 31H and 12L, 31H and 13L, 31H and 14L, 31H and 15L, 31H and 16L, 31H and 17L, 31H and 18L, 31H and 19L, 31H and 20L, 31H and 21L, 31H and 22L, 31H and 23L, 31H and 24L, 31H and 25L, 31H and 26L, 31H and 27L, 31H and 28L, 31H and 29L, 31H and 30L, 31H and 31L, 31H and 32L, 32H and 1L, 32H and 2L, 32H and 3L, 32H and 4L, 32H and 5L, 32H and 6L, 32H and 7L, 32H and 8L, 32H and 9L, 32H and 10L, 32H and 11L, 32H and 12L, 32H and 13L, 32H and 14L, 32H and 15L, 32H and 16L, 32H and 17L, 32H and 18L, 32H and 19L, 32H and 20L, 32H and 21L, 32H and 22L, 32H and 23L, 32H and 24L, 32H and 25L, 32H and 26L, 32H and 27L, 32H and 28L, 32H and 29L, 32H and 30L, 32H and 31L, or 32H and 32L.

In some embodiments, a peptide comprising the CDRs of 1H, 2H, 3H, 4H, 5H, 6H, 7H, 8H, 9H, 10H, 11H, 12H, 13H, 14H, 15H, 16H, 17H, 18H, 19H, 20H, 21H, 22H, 23H, 24H, 25H, 26H, 27H, 28H, 29H, 30H, 31H, or 32H are combined or linked or expressed in conjunction with a peptide comprising SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90, or a variant thereof. In some embodiments, the sequences are at least, or about 90%, 91%, 92%, 93%, 94%, 95%, 96%, 97%, 98%, or 99% identical to the sequence.

In some embodiments, an antibody is provided, including an isolated form thereof, wherein the antibody comprises a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of SEQ ID NO: 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 25; the heavy chain CDR2 has the amino acid sequence of SEQ ID NO: 26; and the heavy chain CDR3 sequence has the amino acid sequence of SEQ ID NO: 27, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 32; and the heavy chain CDR3 sequence has the amino acid sequence of SEQ ID NO: 33, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 38; and the heavy chain CDR3 sequence has the amino acid sequence of SEQ ID NO: 39, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 44; and the heavy chain CDR3 sequence has the amino acid sequence of SEQ ID NO: 45, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 46; and the heavy chain CDR3 sequence has the amino acid sequence of SEQ ID NO: 33, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 48; and the heavy chain CDR3 sequence has the amino acid sequence of SEQ ID NO: 39, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 49; and the heavy chain CDR3 sequence has the amino acid sequence of SEQ ID NO: 45, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 53; the heavy chain CDR2 has the amino acid sequence of SEQ ID NO: 54; and the heavy chain CDR3 sequence has the amino acid sequence of SEQ ID NO: 33, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 54; and the heavy chain CDR3 sequence has the amino acid sequence of SEQ ID NO: 33, or variants of any of the foregoing;

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 57, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 61, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 63, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 66, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 67, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 126, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 71; the heavy chain CDR2 has the amino acid sequence of SEQ ID NO: 72; and the heavy chain CDR3 sequence has the amino acid sequence of SEQ ID NO: 73, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 76; the heavy chain CDR2 has the amino acid sequence of SEQ ID NO: 77; and the heavy chain CDR3 sequence has the amino acid sequence of SEQ ID NO: 78, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 80; the heavy chain CDR2 has the amino acid sequence of SEQ ID NO: 81; and the heavy chain CDR3 sequence has the amino acid sequence of SEQ ID NO: 82, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 86; and the heavy chain CDR3 sequence has the amino acid sequence of SEQ ID NO: 57, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 90; the heavy chain CDR2 has the amino acid sequence of SEQ ID NO: 91; and the heavy chain CDR3 sequence has the amino acid sequence of SEQ ID NO: 92, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 95; the heavy chain CDR2 has the amino acid sequence of SEQ ID NO: 96; and the heavy chain CDR3 sequence has the amino acid sequence of SEQ ID NO: 97, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 101; and the heavy chain CDR3 sequence has the amino acid sequence of SEQ ID NO: 57, or variants of any of the foregoing.

In some embodiments, the antibody, or an isolated form thereof, comprises a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 102; and the heavy chain CDR3 sequence has the amino acid sequence of SEQ ID NO: 57, or variants of any of the foregoing.

In some embodiments, the heavy chain variable region or proteins provided herein are linked to a light chain variable region. In some embodiments, the linker is a peptide linker, such as, but not limited to, GQSSRSSGGGGSSGGGGS (SEQ ID NO: 136); (GGGGS)$_n$ (SEQ ID NO: 137), (GGG-GA)$_n$ (SEQ ID NO: 138), or any combination thereof, wherein each n is independently 1-5. The linked peptide format can be represented by a formula of $V_H$—Z—$V_L$ or $V_L$—Z—$V_H$, wherein Z is the peptide linker. In some embodiments, Z GQSSRSSGGGGSSGGGGS (SEQ ID NO: 136); (GGGGS)$_n$ (SEQ ID NO: 137), (GGGGA)$_n$ (SEQ ID NO: 138), or any combination thereof, wherein each n is independently 1-5.

In some embodiments, the light chain variable region comprising a sequence of any one of sequences as set forth in SEQ ID NOs: 127-135. In some embodiments, the light chain variable region comprises light chain CDR1, CDR2, and CDR3 peptide sequences, wherein the light chain CDR1 sequence has the amino acid sequence of SEQ ID NO: 22, 28, 34, 40, 47, 50, 58, 64, 74, 83, 87, 93, or 98; the light chain CDR2 sequence has the amino acid sequence of SEQ ID NO: 23, 29, 41, 51, 59, 68, 84, 88, or 99, and the light chain CDR3 sequence has the amino acid sequence of SEQ ID NO: 24, 30, 36, 42, 52, 60, 70, 75, 79, 85, 89, 94, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 22; the light chain CDR2 sequence has the amino acid sequence of SEQ ID NO: 23, and the light chain CDR3 sequence has the amino acid sequence of SEQ ID NO: 24, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29, and the light chain CDR3 sequence has the amino acid sequence of SEQ ID NO: 30, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 34; the light chain CDR2 sequence has the amino acid sequence of SEQ ID NO: 29, and the light chain CDR3 sequence has the amino acid sequence of SEQ ID NO: 36, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41, and the light chain CDR3 sequence has the amino acid sequence of SEQ ID NO: 42, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 29, and the light chain CDR3 sequence has the amino acid sequence of SEQ ID NO: 36, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51, and the light chain CDR3 sequence has the amino acid sequence of SEQ ID NO: 52, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59, and the light chain CDR3 sequence has the amino acid sequence of SEQ ID NO: 60, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 60, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68, and the light chain CDR3 sequence has the amino acid sequence of SEQ ID NO: 60, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 70, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 74; the light chain CDR2 sequence has the amino acid sequence of SEQ ID NO: 59, and the light chain CDR3 sequence has the amino acid sequence of SEQ ID NO: 75, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59, and the light chain CDR3 sequence has the amino acid sequence of SEQ ID NO: 79, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 83; the light chain CDR2 sequence has the amino acid sequence of SEQ ID NO: 84, and the light chain CDR3 sequence has the amino acid sequence of SEQ ID NO: 85, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88, and the light chain CDR3 sequence has the amino acid sequence of SEQ ID NO: 89, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 93; the light chain CDR2 sequence has the amino acid sequence of SEQ ID NO: 88, and the light chain CDR3 sequence has the amino acid sequence of SEQ ID NO: 94, or variants of any of the foregoing.

In some embodiments, the antibody, or an isolated form thereof, comprises a light chain variable region comprising light chain CDR1, CDR2, and CDR3 sequences, wherein the light chain CDR1 sequence has the amino acid sequence SEQ ID NO: 98; the light chain CDR2 sequence has the amino acid sequence of SEQ ID NO: 99, and the light chain CDR3 sequence has the amino acid sequence of SEQ ID NO: 100, or variants of any of the foregoing.

In some embodiments, an antibody, or an antigen binding fragment thereof, is provided wherein the antibody, or antigen binding fragment thereof, comprises: (i) a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing; and (ii) a light chain variable region comprising light chain CDR1, CDR2, and CDR3 sequences, wherein the light chain CDR1 sequence has the amino acid sequence 22, 28, 34, 40, 47, 50, 58, 64, 74, 83, 87, 93, or 98; the light chain CDR2 sequence has the amino acid sequence of 23, 29, 41, 51, 59, 68, 84, 88, or 99, and the light chain CDR3 sequence has the amino acid sequence of 24, 30, 36, 42, 52, 60, 70, 75, 79, 85, 89, or 94, or variants of any of the foregoing.

In some embodiments, the following embodiments are provided herein:
1. An antibody, or an isolated form thereof, that binds to claudin 6 with an affinity of less than 10 nM and with at least 100 fold greater $EC_{50}$ than claudin 9, claudin 3, and/or claudin 4.
2. The antibody of embodiment 1, or an isolated form thereof, wherein the antibody comprises a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of SEQ ID NO: 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing.
3. The antibody of embodiment 1, or an isolated form thereof, wherein the antibody comprises:
   a heavy chain variable region comprising heavy chain CDR1, CDR2, and CDR3 sequences, wherein the heavy chain CDR1 sequence has the amino acid sequence of SEQ ID NO: 25; the heavy chain CDR2 has the amino acid sequence of SEQ ID NO: 26; and the heavy chain CDR3 sequence has the amino acid sequence of SEQ ID NO: 27, or variants of any of the foregoing;
   a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 32; and the heavy chain CDR3 sequence has the amino acid sequence of SEQ ID NO: 33, or variants of any of the foregoing;
   a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 38; and the heavy chain CDR3 sequence has the amino acid sequence of SEQ ID NO: 39, or variants of any of the foregoing;
   a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 44; and the heavy chain CDR3 sequence has the amino acid sequence of SEQ ID NO: 45, or variants of any of the foregoing;
   a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 46; and the heavy chain CDR3 sequence has the amino acid sequence of SEQ ID NO: 33, or variants of any of the foregoing;
   a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 48; and the heavy chain CDR3 sequence has the amino acid sequence of SEQ ID NO: 39, or variants of any of the foregoing;
   a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 49; and the heavy chain CDR3 sequence has the amino acid sequence of SEQ ID NO: 45, or variants of any of the foregoing;
   a heavy chain variable region comprising heavy chain CDR1, CDR2, and CDR3 sequences, wherein the heavy chain CDR1 sequence has the amino acid sequence of SEQ ID NO: 53; the heavy chain CDR2 has the amino acid sequence of SEQ ID NO: 54; and the heavy chain CDR3 sequence has the amino acid sequence of SEQ ID NO: 33, or variants of any of the foregoing;
   a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 54; and the heavy chain CDR3 sequence has the amino acid sequence of SEQ ID NO: 33, or variants of any of the foregoing;

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 61, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 63, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 66, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 67, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 126, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69, or variants of any of the foregoing;

a heavy chain variable region comprising heavy chain CDR1, CDR2, and CDR3 sequences, wherein the heavy chain CDR1 sequence has the amino acid sequence of SEQ ID NO: 71; the heavy chain CDR2 has the amino acid sequence of SEQ ID NO: 72; and the heavy chain CDR3 sequence has the amino acid sequence of SEQ ID NO: 73, or variants of any of the foregoing;

a heavy chain variable region comprising heavy chain CDR1, CDR2, and CDR3 sequences, wherein the heavy chain CDR1 sequence has the amino acid sequence of SEQ ID NO: 76; the heavy chain CDR2 has the amino acid sequence of SEQ ID NO: 77; and the heavy chain CDR3 sequence has the amino acid sequence of SEQ ID NO: 78, or variants of any of the foregoing;

a heavy chain variable region comprising heavy chain CDR1, CDR2, and CDR3 sequences, wherein the heavy chain CDR1 sequence has the amino acid sequence of SEQ ID NO: 80; the heavy chain CDR2 has the amino acid sequence of SEQ ID NO: 81; and the heavy chain CDR3 sequence has the amino acid sequence of SEQ ID NO: 82, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 86; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 90; the heavy chain CDR2 has the amino acid sequence of SEQ ID NO: 91; and the heavy chain CDR3 sequence has the amino acid sequence of SEQ ID NO: 92, or variants of any of the foregoing;

a heavy chain variable region comprising heavy chain CDR1, CDR2, and CDR3 sequences, wherein the heavy chain CDR1 sequence has the amino acid sequence of SEQ ID NO: 95; the heavy chain CDR2 has the amino acid sequence of SEQ ID NO: 96; and the heavy chain CDR3 sequence has the amino acid sequence of SEQ ID NO: 97, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 101; and the heavy chain CDR3 sequence has the amino acid sequence of SEQ ID NO: 57, or variants of any of the foregoing; or a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 102; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 139; the heavy chain CDR2 has the amino acid sequence of SEQ ID NO: 140; and the heavy chain CDR3 sequence has the amino acid sequence of SEQ ID NO: 82, or variants of any of the foregoing;

a heavy chain variable region comprising heavy chain CDR1, CDR2, and CDR3 sequences, wherein the heavy chain CDR1 sequence has the amino acid sequence of SEQ ID NO: 141; the heavy chain CDR2 has the amino acid sequence of SEQ ID NO: 142; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 143; the heavy chain CDR2 has the amino acid sequence of SEQ ID NO: 144; and the heavy chain CDR3 sequence has the amino acid sequence of SEQ ID NO: 92, or variants of any of the foregoing; or a heavy chain variable region comprising heavy chain CDR1, CDR2, and CDR3 sequences, wherein the heavy chain CDR1 sequence has the amino acid sequence of SEQ ID NO: 145; the heavy chain CDR2 has the amino acid sequence of SEQ ID NO: 146; and the heavy chain CDR3 sequence has the amino acid sequence of SEQ ID NO: 97, or variants of any of the foregoing.

4. The antibody of any one of embodiments 1-3, wherein the antibody comprises a light chain variable region comprising a sequence of any one of sequences as set forth in SEQ ID NOs: 127-135.

5. The antibody of any one of embodiments 1-3, wherein the antibody comprises a light chain variable region comprising light chain CDR1, CDR2, and CDR3 sequences, wherein the light chain CDR1 sequence has the amino acid sequence of SEQ ID NO: 22, 28, 34, 40, 47, 50, 58, 64, 74, 83, 87, 93, or 98; the light chain CDR2 sequence has the amino acid sequence of SEQ ID NO: 23, 29, 41, 51, 59, 68, 84, 88, or 99, and the light chain CDR3 sequence has the amino acid sequence of SEQ ID NO: 24, 30, 36, 42, 52, 60, 70, 75, 79, 85, 89, 94, or variants of any of the foregoing.

6. The antibody of embodiment 5, wherein antibody comprises:

a light chain variable region comprising light chain CDR1, CDR2, and CDR3 sequences, wherein the light chain CDR1 sequence has the amino acid sequence SEQ ID NO: 22; the light chain CDR2 sequence has the amino acid sequence of SEQ ID NO: 23, and the light chain CDR3 sequence has the amino acid sequence of SEQ ID NO: 24, or variants of any of the foregoing;

a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29, and the light chain CDR3 sequence has the amino acid sequence of SEQ ID NO: 30, or variants of any of the foregoing;

a light chain variable region comprising light chain CDR1, CDR2, and CDR3 sequences, wherein the light chain CDR1 sequence has the amino acid sequence SEQ ID NO: 34; the light chain CDR2 sequence has the amino acid sequence of SEQ ID NO: 29, and the light chain CDR3 sequence has the amino acid sequence of SEQ ID NO: 36, or variants of any of the foregoing;

a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41, and the light chain CDR3 sequence has the amino acid sequence of SEQ ID NO: 42, or variants of any of the foregoing;

a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 29, and the light chain CDR3 sequence has the amino acid sequence of SEQ ID NO: 36, or variants of any of the foregoing;

a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51, and the light chain CDR3 sequence has the amino acid sequence of SEQ ID NO: 52, or variants of any of the foregoing;

a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 70, or variants of any of the foregoing;

a light chain variable region comprising light chain CDR1, CDR2, and CDR3 sequences, wherein the light chain CDR1 sequence has the amino acid sequence SEQ ID NO: 74; the light chain CDR2 sequence has the amino acid sequence of SEQ ID NO: 59, and the light chain CDR3 sequence has the amino acid sequence of SEQ ID NO: 75, or variants of any of the foregoing;

a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59, and the light chain CDR3 sequence has the amino acid sequence of SEQ ID NO: 79, or variants of any of the foregoing;

a light chain variable region comprising light chain CDR1, CDR2, and CDR3 sequences, wherein the light chain CDR1 sequence has the amino acid sequence SEQ ID NO: 83; the light chain CDR2 sequence has the amino acid sequence of SEQ ID NO: 84, and the light chain CDR3 sequence has the amino acid sequence of SEQ ID NO: 85, or variants of any of the foregoing;

a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88, and the light chain CDR3 sequence has the amino acid sequence of SEQ ID NO: 89, or variants of any of the foregoing;

a light chain variable region comprising light chain CDR1, CDR2, and CDR3 sequences, wherein the light chain CDR1 sequence has the amino acid sequence SEQ ID NO: 93; the light chain CDR2 sequence has the amino acid sequence of SEQ ID NO: 88, and the light chain CDR3 sequence has the amino acid sequence of SEQ ID NO: 94, or variants of any of the foregoing; or a light chain variable region comprising light chain CDR1, CDR2, and CDR3 sequences, wherein the light chain CDR1 sequence has the amino acid sequence SEQ ID NO: 98; the light chain CDR2 sequence has the amino acid sequence of SEQ ID NO: 99, and the light chain CDR3 sequence has the amino acid sequence of SEQ ID NO: 100, or variants of any of the foregoing.

7. The antibody of embodiment 1, or antigen binding fragment thereof, wherein the antibody, or antigen binding fragment thereof, comprises:
   (i) a heavy chain variable region comprising heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing; and
   (ii) a light chain variable region comprising light chain CDR1, CDR2, and CDR3 sequences, wherein the light chain CDR1 sequence has the amino acid sequence 22, 28, 34, 40, 47, 50, 58, 64, 74, 83, 87, 93, or 98; the light chain CDR2 sequence has the amino acid sequence of 23, 29, 41, 51, 59, 68, 84, 88, or 99, and the light chain CDR3 sequence has the amino acid sequence of 24, 30, 36, 42, 52, 60, 70, 75, 79, 85, 89, 94, or variants of any of the foregoing.

8. The antibody, or antigen binding fragment thereof, of embodiment 3, wherein the antibody, or antigen binding fragment thereof, comprises:

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 61; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 63; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 66; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 67; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 126; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 70; or variants of any of the foregoing;

a heavy chain variable region comprising heavy chain CDR1, CDR2, and CDR3 sequences, wherein the heavy chain CDR1 sequence has the amino acid sequence of SEQ ID NO: 71; the heavy chain CDR2 has the amino acid sequence of SEQ ID NO: 72; and the heavy chain CDR3 sequence has the amino acid sequence of SEQ ID NO: 73; or variants of any of the foregoing; and a light chain variable region comprising light chain CDR1, CDR2, and CDR3 sequences, wherein the light chain CDR1 sequence has the amino acid sequence SEQ ID NO: 74; the light chain CDR2 sequence has the amino acid sequence of SEQ ID NO: 59; and the light chain CDR3 sequence has the amino acid sequence of SEQ ID NO: 75; or variants of any of the foregoing;

a heavy chain variable region comprising heavy chain CDR1, CDR2, and CDR3 sequences, wherein the heavy chain CDR1 sequence has the amino acid sequence of SEQ ID NO: 76; the heavy chain CDR2 has the amino acid sequence of SEQ ID NO: 77; and the heavy chain CDR3 sequence has the amino acid sequence of SEQ ID NO: 78; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 79; or variants of any of the foregoing;

a heavy chain variable region comprising heavy chain CDR1, CDR2, and CDR3 sequences, wherein the heavy chain CDR1 sequence has the amino acid sequence of SEQ ID NO: 80; the heavy chain CDR2 has the amino acid sequence of SEQ ID NO: 81; and the heavy chain CDR3 sequence has the amino acid sequence of SEQ ID NO: 82; or variants of any of the foregoing; and a light chain variable region comprising light chain CDR1, CDR2, and CDR3 sequences, wherein the light chain CDR1 sequence has the amino acid sequence SEQ ID NO: 83; the light chain CDR2 sequence has the amino acid sequence of SEQ ID NO: 84; and the light chain CDR3 sequence has the amino acid sequence of SEQ ID NO: 85; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 86; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88; and the light chain CDR3 sequence has the amino acid sequence of SEQ ID NO: 89; or variants of any of the foregoing;

a heavy chain variable region comprising heavy chain CDR1, CDR2, and CDR3 sequences, wherein the heavy chain CDR1 sequence has the amino acid sequence of SEQ ID NO: 90; the heavy chain CDR2 has the amino acid sequence of SEQ ID NO: 91; and the heavy chain CDR3 sequence has the amino acid sequence of SEQ ID NO: 92; or variants of any of the foregoing; and a light chain variable region comprising light chain CDR1, CDR2, and CDR3 sequences, wherein the light chain CDR1 sequence has the amino acid sequence SEQ ID NO: 93; the light chain CDR2 sequence has the amino acid sequence of SEQ ID NO: 88; and the light chain CDR3 sequence has the amino acid sequence of SEQ ID NO: 94; or variants of any of the foregoing;

a heavy chain variable region comprising heavy chain CDR1, CDR2, and CDR3 sequences, wherein the heavy chain CDR1 sequence has the amino acid sequence of SEQ ID NO: 95; the heavy chain CDR2 has the amino acid sequence of SEQ ID NO: 96; and the heavy chain CDR3 sequence has the amino acid sequence of SEQ ID NO: 97; or variants of any of the foregoing; and a light chain variable region comprising light chain CDR1, CDR2, and CDR3 sequences, wherein the light chain CDR1 sequence has the amino acid sequence SEQ ID NO: 98; the light chain CDR2 sequence has the amino acid sequence of SEQ ID NO: 99; and the light chain CDR3 sequence has the amino acid sequence of SEQ ID NO: 100; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 101; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing; or a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 102; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88; and the light chain CDR3 sequence has the amino acid sequence of SEQ ID NO: 89; or variants of any of the foregoing;

a heavy chain variable region comprising heavy chain CDR1, CDR2, and CDR3 sequences, wherein the heavy chain CDR1 sequence has the amino acid sequence of SEQ ID NO: 25; the heavy chain CDR2 has the amino acid sequence of SEQ ID NO: 26; and the heavy chain CDR3 sequence has the amino acid sequence of SEQ ID NO: 27; or variants of any of the foregoing; and a light chain variable region comprising light chain CDR1, CDR2, and CDR3 sequences, wherein the light chain CDR1 sequence has the amino acid sequence SEQ ID NO: 22; the light chain CDR2 sequence has the amino acid sequence of SEQ ID NO: 23; and the light chain CDR3 sequence has the amino acid sequence of SEQ ID NO: 24; or variants of any of the foregoing;

a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 32; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29; and the light chain CDR3 sequence has the amino acid sequence of SEQ ID NO: 30; or variants of any of the foregoing;

a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 28; and the heavy chain CDR3 sequence has the amino acid sequence of SEQ ID NO: 29; or variants of any of the foregoing; and a light chain variable region comprising light chain CDR1, CDR2, and CDR3 sequences, wherein the light chain CDR1 sequence has the amino acid sequence SEQ ID NO: 34; the light chain CDR2 sequence has the amino acid sequence of SEQ ID NO: 29; and the light chain CDR3 sequence has the amino acid sequence of SEQ ID NO: 26; or variants of any of the foregoing;

a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 44; and the heavy chain CDR3 sequence has the amino acid sequence of SEQ ID NO: 45; or variants of any of the foregoing; and a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41; and the light chain CDR3 sequence has the amino acid sequence of SEQ ID NO: 42; or variants of any of the foregoing;

a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 46; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29; and the light chain CDR3 sequence has the amino acid sequence of SEQ ID NO: 30; or variants of any of the foregoing;

a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 48; and the heavy chain CDR3 sequence has the amino acid sequence of SEQ ID NO: 39; or variants of any of the foregoing; and a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 29; and the light chain CDR3 sequence has the amino acid sequence of SEQ ID NO: 36; or variants of any of the foregoing;

a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 49; and the heavy chain CDR3 sequence has the amino acid sequence of SEQ ID NO: 45; or variants of any of the foregoing; and a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41; and the light chain CDR3 sequence has the amino acid sequence of SEQ ID NO: 42; or variants of any of the foregoing;

a heavy chain variable region comprising heavy chain CDR1, CDR2, and CDR3 sequences, wherein the heavy chain CDR1 sequence has the amino acid sequence of SEQ ID NO: 53; the heavy chain CDR2 has the amino acid sequence of SEQ ID NO: 54; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51; and the light chain CDR3 sequence has the amino acid sequence of SEQ ID NO: 52; or variants of any of the foregoing;

a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 54; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51; and the light chain CDR3 sequence has the amino acid sequence of SEQ ID NO: 52; or variants of any of the foregoing.

9. The antibody of any one of embodiments 1-8, wherein the antibody is a monoclonal antibody.

10. The antibody of any one of embodiments 1-9, wherein the antibody is a humanized antibody.

11. The antibody of any one of embodiments 1-8, wherein the antibody is a chicken antibody.

12. The antibody of any one of embodiments 1-11, wherein the antibody comprises a sequence as provided herein.

13. The isolated antibody of any of the preceding embodiments, wherein the antibody comprises a sequence a CDR sequence as provided herein.

14. The isolated antibody of any of the preceding embodiments, wherein the antibody comprises a $V_L$ a sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, or SEQ ID NO: 124, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, or SEQ ID NO: 135, or any variants of the foregoing.

15. The isolated antibody of any of the preceding embodiments, wherein the antibody comprises a $V_L$ sequence of SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, or SEQ ID NO: 135, or any variants of the foregoing.

16. The isolated antibody of any of the preceding embodiments, wherein the antibody comprises a $V_L$ sequence of SEQ ID NO: 127, SEQ ID NO: 128, SEQ ID NO: 129, or SEQ ID NO: 130, or any variants of the foregoing.

17. The isolated antibody of any of the preceding embodiments, wherein the antibody comprises a $V_L$ sequence of SEQ ID NO: 127 or SEQ ID NO: 128.

18. The isolated antibody of any of the preceding embodiments, wherein the antibody comprises a $V_H$ sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, or SEQ ID NO: 123, or any variant thereof.

19. The isolated antibody of any of the preceding embodiments, wherein the antibody comprises a $V_H$ sequence of SEQ ID NO: 103.

20. The isolated antibody of any of the preceding embodiments, wherein the antibody comprises a $V_H$ sequence of SEQ ID NO: 105.

21. The isolated antibody of any of the preceding embodiments, wherein the antibody comprises a $V_H$ sequence of SEQ ID NO: 107.

22. The isolated antibody of any of the preceding embodiments, wherein the antibody comprises a $V_H$ sequence of SEQ ID NO: 109.

23. The isolated antibody of any of the preceding embodiments, wherein the antibody comprises a $V_H$ sequence of SEQ ID NO: 111.

24. The isolated antibody of any of the preceding embodiments, wherein the antibody comprises a $V_H$ sequence of SEQ ID NO: 113.

25. The isolated antibody of any of the preceding embodiments, wherein the antibody comprises a $V_H$ sequence of SEQ ID NO: 115.

26. The isolated antibody of any of the preceding embodiments, wherein the antibody comprises a $V_H$ sequence of SEQ ID NO: 117.

27. The isolated antibody of any of the preceding embodiments, wherein the antibody comprises a $V_H$ sequence of SEQ ID NO: 119.

28. The isolated antibody of any of the preceding embodiments, wherein the antibody comprises a $V_H$ sequence of SEQ ID NO: 121.

29. The isolated antibody of any of the preceding embodiments, wherein the antibody comprises a $V_H$ sequence of SEQ ID NO: 123.

30. The isolated antibody of any of the preceding embodiments, wherein the antibody comprises a CDR of GFSFSSY (SEQ ID NO: 139); YSSASSTY (SEQ ID NO: 140); AAGRTYRGWATYIADSIDA (SEQ ID NO: 82); GFDFSSY (SEQ ID NO: 141); GSTGSS (SEQ ID NO: 142); SVGNGNSWSGYIATSIDA (SEQ ID NO: 57); GFSISSY (SEQ ID NO: 143); YSGSR (SEQ ID NO: 144); SSYCTAWTGCDVYAGGSIDA (SEQ ID NO: 92); GFTFSSY (SEQ ID NO: 145); DSGST (SEQ ID NO: 146); DAYGYCGWSGCSADSIDA (SEQ ID NO: 97), SGDSSWYGYG (SEQ ID NO: 83); ESGKRPS (SEQ ID NO: 84); GSADSNSIGI (SEQ ID NO: 85); SGGSSGYG (SEQ ID NO: 87); SNDKRPS (SEQ ID NO: 88); GSTDNSYVGI (SEQ ID NO: 89); SGDSSDDGSYYYG (SEQ ID NO: 93); SNDKRPS (SEQ ID NO: 88); GSYDSSTGI (SEQ ID NO: 94); SGGNNYYG (SEQ ID NO: 98); YNDKRPS (SEQ ID NO: 99); GGWDSSGGI (SEQ ID NO: 100), or as otherwise described herein.

31. The isolated antibody of any of the preceding embodiments, wherein the antibody comprises a $V_H$ CDR of GFSFSSY (SEQ ID NO: 139); YSSASSTY (SEQ ID NO: 140); AAGRTYRGWATYIADSIDA (SEQ ID NO: 82); GFDFSSY (SEQ ID NO: 141); GSTGSS (SEQ ID NO: 142); SVGNGNSWSGYIATSIDA (SEQ ID NO: 57); GFSISSY (SEQ ID NO: 143); YSGSR (SEQ ID NO: 144); SSYCTAWTGCDVYAGGSIDA (SEQ ID NO: 92); GFTFSSY (SEQ ID NO: 145); DSGST (SEQ ID NO: 146); DAYGYCGWSGCSADSIDA (SEQ ID NO: 97); CSGDSSWYGYG (SEQ ID NO: 22); IYESGKRP (SEQ ID NO: 23); CGSADSNSIGIF (SEQ ID NO: 24); GFSFSSYDMGWV (SEQ ID NO: 25); VASIYSSASSTYYA (SEQ ID NO: 26); CAKAAGRTYRGWATYIADSIDA (SEQ ID NO: 27); CSGGSSGYG (SEQ ID NO: 28); IYSNDKRP (SEQ ID NO: 29); CGSTDNSYVGIF (SEQ ID NO: 30); GFDFSSYAMNWV (SEQ ID NO: 31); VAGIGSTGSSTGYG (SEQ ID NO: 32); CAKSVGNGNSWSGYIATSIDA (SEQ ID NO: 33); CSGDSSDDGSYYYG (SEQ ID NO: 34); IYSNDKRP (SEQ ID NO: 29); CGSYDSSTGIF (SEQ ID NO: 36); GFSISSYTMQWV (SEQ ID NO: 37); VAGIYSGSRTYYG (SEQ ID NO: 38); CAKSSYCTAWTGCDVYAGGSIDA (SEQ ID NO: 39); CSGGNNYYG (SEQ ID NO: 40); IYYNDKRP (SEQ ID NO: 41); CGGWDSSGGIF (SEQ ID NO: 42); GFTFSSYSMFWV (SEQ ID NO: 43); VAGIDSGSTTFYG (SEQ ID NO: 44); CAKDAYGYCGWSGCSADSIDA (SEQ ID NO: 45); CSGDSSWYGYG (SEQ ID NO: 22); IYESGKRP (SEQ ID NO: 23); CGSADSNSIGIF (SEQ ID NO: 24); GFSFSSYDMGWV (SEQ ID NO: 25); VASIYSSASSTYYA (SEQ ID NO: 26); CAKAAGRTYRGWATYIADSIDA (SEQ ID NO: 27); CSGGSSGYG (SEQ ID NO: 28); IYSNDKRP (SEQ ID NO: 29); CGSTDNSYVGIF (SEQ ID NO: 30); GFDFSSYAMNWV (SEQ ID NO: 31); VAGIGSTGSSTGYA (SEQ ID NO: 46); CAKSVGNGNSWSGYIATSIDA (SEQ ID NO: 33); CSGDDGSYYYG (SEQ ID NO: 47); IYSNDKRP (SEQ ID NO: 29); CGSYDSSTGIF (SEQ ID NO: 36); GFSISSYTMQWV (SEQ ID NO: 37); VAGIYSGSRTYYA (SEQ ID NO: 48); CAKSSYCTAWTGCDVYAGGSIDA (SEQ ID NO: 39); CSGGNNYYG (SEQ ID NO: 40); IYYNDKRP (SEQ ID NO: 41); CGGWDSSGGIF (SEQ ID NO: 42); GFTFSSYSMFWV (SEQ ID NO: 43); VAGIDSGSTTFYA (SEQ ID NO: 49); CAKDAYGYCGWSGCSADSIDA (SEQ ID NO: 45); CSGGSGSYG (SEQ ID NO: 50); IYGTNKRP (SEQ ID NO: 51); CGSADSSTNAGIF (SEQ ID NO: 52); GFTFSSYAMSWV (SEQ ID NO: 53); VAGISSSGRYTGYA (SEQ ID NO: 54); CAKSVGNGNSWSGYIATSIDA (SEQ ID NO: 33); CSGGSGSYG (SEQ ID NO: 50); IYGTNKRP (SEQ ID NO: 51); CGSADSSTNAGIF (SEQ ID NO: 52); GFTFSSYAMNWV (SEQ ID NO: 55); or VAGISSSGRYTGYA (SEQ ID NO: 54); CAKSVGNGNSWSGYIATSIDA (SEQ ID NO: 33), or as otherwise described herein.

32. The isolated antibody of any of the preceding embodiments, wherein the antibody comprises a $V_L$ CDR of SGDSSWYGYG (SEQ ID NO: 83); ESGKRPS (SEQ ID NO: 84); GSADSNSIGI (SEQ ID NO: 85); SGGSSGYG (SEQ ID NO: 87); SNDKRPS (SEQ ID NO: 88); GSTDNSYVGI (SEQ ID NO: 89); SGDSSDDGSYYYG (SEQ ID NO: 93); SNDKRPS (SEQ ID NO: 88); GSYDSSTGI (SEQ ID NO: 94); SGGNNYYG (SEQ ID NO: 98); YNDKRPS (SEQ ID NO: 99); GGWDSSGGI (SEQ ID NO: 100), CSGDSSWYGYG (SEQ ID NO: 22); IYESGKRP (SEQ ID NO: 23); CGSADSNSIGIF (SEQ ID NO: 24); CSGGSSGYG (SEQ ID NO: 28); IYSNDKRP (SEQ ID NO: 29); CGSTDNSYVGIF (SEQ ID NO: 30); CSGDSSDDGSYYYG (SEQ ID NO: 34); IYSNDKRP (SEQ ID NO: 29); CGSYDSSTGIF (SEQ ID NO: 36); CSGGNNYYG (SEQ ID NO: 40); IYYNDKRP (SEQ ID NO: 41); CGGWDSSGGIF (SEQ ID NO: 42); IYESGKRP (SEQ ID NO: 23); CGSADSNSIGIF (SEQ ID NO: 24); CSGGSSGYG (SEQ ID NO: 28); IYSNDKRP (SEQ ID NO: 29); CGSTDNSYVGIF (SEQ ID NO: 30); CSGDDGSYYYG (SEQ ID NO: 47); IYSNDKRP (SEQ ID NO: 29); CGSYDSSTGIF (SEQ ID NO: 36); CSGGNNYYG (SEQ ID NO: 40); IYYNDKRP (SEQ ID NO: 41); CGGWDSSGGIF (SEQ ID NO: 42); CSGGSGSYG (SEQ ID NO: 50); IYGTNKRP (SEQ ID NO: 51); CGSADSSTNAGIF (SEQ ID NO: 52); CSGGSGSYG (SEQ ID NO: 50); IYGTNKRP (SEQ ID NO: 51); or CGSADSSTNAGIF (SEQ ID NO: 52), or as otherwise described herein.

33. The isolated antibody of any one of the preceding embodiments, wherein the CDRs of the $V_H$ chain comprises:

1H.
GFSFSSY; (SEQ ID NO: 139)

YSSASSTY; (SEQ ID NO: 140)
and

AAGRTYRGWATYIADSIDA; (SEQ ID NO: 82)
or

2H.
GFDFSSY; (SEQ ID NO: 141)

GSTGSS; (SEQ ID NO: 142)
and

SVGNGNSWSGYIATSIDA; (SEQ ID NO: 57)
or

3H.
GFSISSY; (SEQ ID NO: 143)

YSGSR; (SEQ ID NO: 144)
and

SSYCTAWTGCDVYAGGSIDA; (SEQ ID NO: 92)
or

4H.
GFTFSSY; (SEQ ID NO: 145)

DSGST; (SEQ ID NO: 146)
and

DAYGYCGWSGCSADSIDA; (SEQ ID NO: 97)
or

5H.
GFSFSSYDMGWV; (SEQ ID NO: 25)

VASIYSSASSTYYA; (SEQ ID NO: 26)
and

CAKAAGRTYRGWATYIADSIDA; (SEQ ID NO: 27)
or

6H.
GFDFSSYAMNWV; (SEQ ID NO: 31)

VAGIGSTGSSTGYG; (SEQ ID NO: 32)
and

CAKSVGNGNSWSGYIATSIDA; (SEQ ID NO: 33)
or

7H.
GFSISSYTMQWV; (SEQ ID NO: 37)

VAGIYSGSRTYYG; (SEQ ID NO: 38)
and

CAKSSYCTAWTGCDVYAGGSIDA; (SEQ ID NO: 39)
or

8H.
GFTFSSYSMFWV; (SEQ ID NO: 43)

VAGIDSGSTTFYG; (SEQ ID NO: 44)
and

CAKDAYGYCGWSGCSADSIDA; (SEQ ID NO: 45)
or

9H.
GFSFSSYDMGWV; (SEQ ID NO: 25)

VASIYSSASSTYYA; (SEQ ID NO: 26)
and

CAKAAGRTYRGWATYIADSIDA; (SEQ ID NO: 27)
or

10H.
GFDFSSYAMNWV; (SEQ ID NO: 31)

VAGIGSTGSSTGYA; (SEQ ID NO: 46)
and

CAKSVGNGNSWSGYIATSIDA; (SEQ ID NO: 33)
or

11H.
GFSISSYTMQWV; (SEQ ID NO: 37)

VAGIYSGSRTYYA; (SEQ ID NO: 48)
and

CAKSSYCTAWTGCDVYAGGSIDA; (SEQ ID NO: 39)
or

12H.
GFTFSSYSMFWV; (SEQ ID NO: 43)

VAGIDSGSTTFYA; (SEQ ID NO: 49)
and

CAKDAYGYCGWSGCSADSIDA; (SEQ ID NO: 45)
or

-continued

13H.
GFTFSSYAMSWV; (SEQ ID NO: 53)

VAGISSSGRYTGYA; (SEQ ID NO: 54)
and

CAKSVGNGNSWSGYIATSIDA; (SEQ ID NO: 33)
or

14H.
GFTFSSYAMNWV; (SEQ ID NO: 55)

VAGISSSGRYTGYA; (SEQ ID NO: 54)
and

CAKSVGNGNSWSGYIATSIDA; (SEQ ID NO: 33)
or

15H.
SYAMS; (SEQ ID NO: 56)

GISSSGRYTGYADSVKG; (SEQ ID NO: 101)
and

SVGNGNSWSGYIATSIDA; (SEQ ID NO: 57)
or

16H.
SYAMS; (SEQ ID NO: 56)

GISSSGRYTGYADSVKG; (SEQ ID NO: 101)
and

SVGNGNSWSGYVATSIDA; (SEQ ID NO: 61)
or

17H.
SYAMN; (SEQ ID NO: 62)

GISSSGRYTGYADSVKG; (SEQ ID NO: 101)
and

SVGSGVSWSGYVATSIDA; (SEQ ID NO: 63)
or

18H.
SYAMN; (SEQ ID NO: 62)

GISSSGRYTGYADSVKG; (SEQ ID NO: 101)
and

SMGSGVSWSGYVATSIDA; (SEQ ID NO: 65)
or

19H.
SYAMN; (SEQ ID NO: 62)

GISSSGRYTGYADSVKG; (SEQ ID NO: 101)
and

SMGSGVSWSGYVATSIDV; (SEQ ID NO: 66)
or

20H.
SYAMN; (SEQ ID NO: 62)

GISSSGRYTGYADSVKG; (SEQ ID NO: 101)
and

SVGSGVSWSGYVATSLDA; (SEQ ID NO: 67)
or

21H.
SYAMN; (SEQ ID NO: 62)

GISSSGRYTGYADSVKG; (SEQ ID NO: 101)
and

SMGSGVSWSGYVATSIDA; (SEQ ID NO: 65)
or

22H.
SYAMN; (SEQ ID NO: 62)

GISSSGRYTGYADSVKG; (SEQ ID NO: 101)
and

SMGSGVSWSGYVATSLDV; (SEQ ID NO: 126)
or

23H.
SYAMN; (SEQ ID NO: 62)

GISSSGRYTGYADSVKG; (SEQ ID NO: 101)
and

SVGSGVSWSGYVATSLDV; (SEQ ID NO: 69)
or

24H.
SYAMN; (SEQ ID NO: 62)

GISSSGRYTGYADSVKG; (SEQ ID NO: 101)
and

SVGSGVSWSGYVATSLDV; (SEQ ID NO: 69)
or

25H.
SYGMS; (SEQ ID NO: 71)

GIGSSGIYTHYADSVKG; (SEQ ID NO: 72)
and

SPGDSDWCGWAGYGIYSCRVAGFIDA; (SEQ ID NO: 73)
or

26H.
GYAMS; (SEQ ID NO: 76)

GIYSSGSYTFYADSVKG; (SEQ ID NO: 77)
and

GTGYCDWSGWCYSGAANIDA; (SEQ ID NO: 78)
or

27H.
SYDMG; (SEQ ID NO: 80)

SIYSSASSTYYAPAVKG; (SEQ ID NO: 81)
and

AAGRTYRGWATYIADSIDA; (SEQ ID NO: 82)
or

28H.
SYAMN; (SEQ ID NO: 62)

GIGSTGSSTGYGPAVKG; (SEQ ID NO: 86)
and

SVGNGNSWSGYIATSIDA; (SEQ ID NO: 57)
or

29H.
SYTMQ; (SEQ ID NO: 90)

GIYSGSRTYYGAAVQG; (SEQ ID NO: 91)
and

SSYCTAWTGCDVYAGGSIDA; (SEQ ID NO: 92)
or

30H.
SYSMF; (SEQ ID NO: 95)

GIDSGSTTFYGSAVKG; (SEQ ID NO: 96)
and

DAYGYCGWSGCSADSIDA; (SEQ ID NO: 97)
or

31H.
SYAMN; (SEQ ID NO: 62)

GISSSGRYTGYADSVKG; (SEQ ID NO: 101)
and

SVGNGNSWSGYIATSIDA; (SEQ ID NO: 57)
or

32H.
SYAMN; (SEQ ID NO: 62)

GIGSTGSSTGYADSVKG; (SEQ ID NO: 102)
and

SVGNGNSWSGYIATSIDA. (SEQ ID NO: 57)

34. The isolated antibody of any one of the preceding embodiments, wherein the $V_L$ chain comprises the CDRs of:

1L.
SGDSSWYGYG; (SEQ ID NO: 83)

ESGKRPS; (SEQ ID NO: 84)
and

GSADSNSIGI; (SEQ ID NO: 85)
or

2L.
SGGSSGYG; (SEQ ID NO: 87)

SNDKRPS; (SEQ ID NO: 88)
and

GSTDNSYVGI; (SEQ ID NO: 89)
or

3L.
SGDSSDDGSYYYG; (SEQ ID NO: 93)

SNDKRPS; (SEQ ID NO: 88)
and

GSYDSSTGI; (SEQ ID NO: 94)
or

4L.
SGGNNYYG; (SEQ ID NO: 98)

YNDKRPS; (SEQ ID NO: 99)
and

GGWDSSGGI; (SEQ ID NO: 100)
or

5L.

CSGDSSWYGYG; (SEQ ID NO: 22)

IYESGKRP; (SEQ ID NO: 23)
and

CGSADSNSIGIF; (SEQ ID NO: 24)
or

6L.

CSGGSSGYG; (SEQ ID NO: 28)

IYSNDKRP; (SEQ ID NO: 29)
and

CGSTDNSYVGIF; (SEQ ID NO: 30)
or

7L.

CSGDSSDDGSYYYG; (SEQ ID NO: 34)

IYSNDKRP; (SEQ ID NO: 29)
and

CGSYDSSTGIF; (SEQ ID NO: 36)
or

8L.

CSGGNNYYG; (SEQ ID NO: 40)

IYYNDKRP; (SEQ ID NO: 41)
and

CGGWDSSGGIF; (SEQ ID NO: 42)
or

9L.

CSGDSSWYGYG; (SEQ ID NO: 22)

IYESGKRP; (SEQ ID NO: 23)
and

CGSADSNSIGIF; (SEQ ID NO: 24)
or

10L.

CSGGSSGYG; (SEQ ID NO: 28)

IYSNDKRP; (SEQ ID NO: 29)
and

CGSTDNSYVGIF; (SEQ ID NO: 30)
or

11L.

CSGDDGSYYYG; (SEQ ID NO: 47)

IYSNDKRP; (SEQ ID NO: 29)
and

CGSYDSSTGIF; (SEQ ID NO: 36)
or

12L.

CSGGNNYYG; (SEQ ID NO: 40)

IYYNDKRP; (SEQ ID NO: 41)
and

CGGWDSSGGIF; (SEQ ID NO: 42)
or

13L.

CSGGSGSYG; (SEQ ID NO: 50)

IYGTNKRP; (SEQ ID NO: 51)
and

CGSADSSTNAGIF; (SEQ ID NO: 52)
or

14L.

CSGGSGSYG; (SEQ ID NO: 50)

IYGTNKRP; (SEQ ID NO: 51)
and

CGSADSSTNAGIF; (SEQ ID NO: 52)
or

15L.

SGGSGSYG; (SEQ ID NO: 58)

GTNKRPS; (SEQ ID NO: 59)
and

GSADSSTNAGI; (SEQ ID NO: 60)
or

16L.

SGGSGSYG; (SEQ ID NO: 58)

GTNKRPS; (SEQ ID NO: 59)
and

GSADSSTNAGI; (SEQ ID NO: 60)
or

17L.

SAGSGLYG; (SEQ ID NO: 64)

GTNKRPS; (SEQ ID NO: 59)
and

GSADSSTNAGI; (SEQ ID NO: 60)
or

18L.

SAGSGLYG; (SEQ ID NO: 64)

GTNKRPS; (SEQ ID NO: 59)
and

GSADSSTNAGI; (SEQ ID NO: 60)
or

19L.

SAGSGLYG; (SEQ ID NO: 64)

GTNKRPS; (SEQ ID NO: 59)
and

GSADSSTNAGI; (SEQ ID NO: 60)
or

20L.

SAGSGLYG; (SEQ ID NO: 64)

GTNKRPS; (SEQ ID NO: 59)
and

GSADSSTNAGI; (SEQ ID NO: 60)
or

21L.

SGGSGSYG; (SEQ ID NO: 58)

GTYKRPS; (SEQ ID NO: 68)
and

GSADSSTNAGI; (SEQ ID NO: 60)
or

22L.

SGGSGSYG; (SEQ ID NO: 58)

GTYKRPS; (SEQ ID NO: 68)
and

GSADSSTNAGI; (SEQ ID NO: 60)
or

23L.

SGGSGSYG; (SEQ ID NO: 58)

GTYKRPS; (SEQ ID NO: 68)
and

GSADSSTNAGI; (SEQ ID NO: 60)
or

24L.

SAGSGLYG; (SEQ ID NO: 64)

GTNKRPS; (SEQ ID NO: 59)
and

GSNDASTNAGI; (SEQ ID NO: 70)
or

25L.

SGGYNGHYG; (SEQ ID NO: 74)

GTNKRPS; (SEQ ID NO: 59)
and

GGYDSSAGI; (SEQ ID NO: 75)
or

26L.

SGGSGSYGYYG; GTNKRPS; (SEQ ID NO: 59)
and

GSEDSSSGAGI; (SEQ ID NO: 79)
or

27L.

SGDSSWYGYG; (SEQ ID NO: 83)

ESGKRPS; (SEQ ID NO: 84)
and

GSADSNSIGI; (SEQ ID NO: 85)
or

28L.

SGGSSGYG; (SEQ ID NO: 87)

SNDKRPS; (SEQ ID NO: 88)
and

GSTDNSYVGI; (SEQ ID NO: 89)
or

29L.

SGDSSDDGSYYYG; (SEQ ID NO: 93)

SNDKRPS; (SEQ ID NO: 88)
and

GSYDSSTGI; (SEQ ID NO: 94)
or

-continued

30L.

(SEQ ID NO: 98)
SGGNNYYG;

(SEQ ID NO: 99)
YNDKRPS;
and (SEQ ID NO: 100)
GGWDSSGGI;
or

31L.

(SEQ ID NO: 58)
SGGSGSYG;

(SEQ ID NO: 59)
GTNKRPS;
and (SEQ ID NO: 60)
GSADSSTNAGI;
or

32L.

(SEQ ID NO: 87)
SGGSSGYG;

(SEQ ID NO: 88)
SNDKRPS;
and (SEQ ID NO: 89)
GSTDNSYVGI.

35. The antibody of any one of the preceding embodiments, wherein the antibody comprises the CDRs of 1H and 1L, 1H and 2L, 1H and 3L, 1H and 4L, 1H and 5L, 1H and 6L, 1H and 7L, 1H and 8L, 1H and 9L, 1H and 10L, 1H and 11L, 1H and 12L, 1H and 13L, 1H and 14L, 1H and 15L, 1H and 16L, 1H and 17L, 1H and 18L, 1H and 19L, 1H and 20L, 1H and 21L, 1H and 22L, 1H and 23L, 1H and 24L, 1H and 25L, 1H and 26L, 1H and 27L, 1H and 28L, 1H and 29L, 1H and 30L, 1H and 31L, 1H and 32L, 2H and 1L, 2H and 2L, 2H and 3L, 2H and 4L, 2H and 5L, 2H and 6L, 2H and 7L, 2H and 8L, 2H and 9L, 2H and 10L, 2H and 11L, 2H and 12L, 2H and 13L, 2H and 14L, 2H and 15L, 2H and 16L, 2H and 17L, 2H and 18L, 2H and 19L, 2H and 20L, 2H and 21L, 2H and 22L, 2H and 23L, 2H and 24L, 2H and 25L, 2H and 26L, 2H and 27L, 2H and 28L, 2H and 29L, 2H and 30L, 2H and 31L, 2H and 32L, 3H and 1L, 3H and 2L, 3H and 3L, 3H and 4L, 3H and 5L, 3H and 6L, 3H and 7L, 3H and 8L, 3H and 9L, 3H and 10L, 3H and 11L, 3H and 12L, 3H and 13L, 3H and 14L, 3H and 15L, 3H and 16L, 3H and 17L, 3H and 18L, 3H and 19L, 3H and 20L, 3H and 21L, 3H and 22L, 3H and 23L, 3H and 24L, 3H and 25L, 3H and 26L, 3H and 27L, 3H and 28L, 3H and 29L, 3H and 30L, 3H and 31L, 3H and 32L, 4H and 1L, 4H and 2L, 4H and 3L, 4H and 4L, 4H and 5L, 4H and 6L, 4H and 7L, 4H and 8L, 4H and 9L, 4H and 10L, 4H and 11L, 4H and 12L, 4H and 13L, 4H and 14L, 4H and 15L, 4H and 16L, 4H and 17L, 4H and 18L, 4H and 19L, 4H and 20L, 4H and 21L, 4H and 22L, 4H and 23L, 4H and 24L, 4H and 25L, 4H and 26L, 4H and 27L, 4H and 28L, 4H and 29L, 4H and 30L, 4H and 31L, 4H and 32L, 5H and 1L, 5H and 2L, 5H and 3L, 5H and 4L, 5H and 5L, 5H and 6L, 5H and 7L, 5H and 8L, 5H and 9L, 5H and 10L, 5H and 11L, 5H and 12L, 5H and 13L, 5H and 14L, 5H and 15L, 5H and 16L, 5H and 17L, 5H and 18L, 5H and 19L, 5H and 20L, 5H and 21L, 5H and 22L, 5H and 23L, 5H and 24L, 5H and 25L, 5H and 26L, 5H and 27L, 5H and 28L, 5H and 29L, 5H and 30L, 5H and 31L, 5H and 32L, 6H and 1L, 6H and 2L, 6H and 3L, 6H and 4L, 6H and 5L, 6H and 6L, 6H and 7L, 6H and 8L, 6H and 9L, 6H and 10L, 6H and 11L, 6H and 12L, 6H and 13L, 6H and 14L, 6H and 15L, 6H and 16L, 6H and 17L, 6H and 18L, 6H and 19L, 6H and 20L, 6H and 21L, 6H and 22L, 6H and 23L, 6H and 24L, 6H and 25L, 6H and 26L, 6H and 27L, 6H and 28L, 6H and 29L, 6H and 30L, 6H and 31L, 6H and 32L, 7H and 1L, 7H and 2L, 7H and 3L, 7H and 4L, 7H and 5L, 7H and 6L, 7H and 7L, 7H and 8L, 7H and 9L, 7H and 10L, 7H and 11L, 7H and 12L, 7H and 13L, 7H and 14L, 7H and 15L, 7H and 16L, 7H and 17L, 7H and 18L, 7H and 19L, 7H and 20L, 7H and 21L, 7H and 22L, 7H and 23L, 7H and 24L, 7H and 25L, 7H and 26L, 7H and 27L, 7H and 28L, 7H and 29L, 7H and 30L, 7H and 31L, 7H and 32L, 8H and 1L, 8H and 2L, 8H and 3L, 8H and 4L, 8H and 5L, 8H and 6L, 8H and 7L, 8H and 8L, 8H and 9L, 8H and 10L, 8H and 11L, 8H and 12L, 8H and 13L, 8H and 14L, 8H and 15L, 8H and 16L, 8H and 17L, 8H and 18L, 8H and 19L, 8H and 20L, 8H and 21L, 8H and 22L, 8H and 23L, 8H and 24L, 8H and 25L, 8H and 26L, 8H and 27L, 8H and 28L, 8H and 29L, 8H and 30L, 8H and 31L, 8H and 32L, 9H and 1L, 9H and 2L, 9H and 3L, 9H and 4L, 9H and 5L, 9H and 6L, 9H and 7L, 9H and 8L, 9H and 9L, 9H and 10L, 9H and 11L, 9H and 12L, 9H and 13L, 9H and 14L, 9H and 15L, 9H and 16L, 9H and 17L, 9H and 18L, 9H and 19L, 9H and 20L, 9H and 21L, 9H and 22L, 9H and 23L, 9H and 24L, 9H and 25L, 9H and 26L, 9H and 27L, 9H and 28L, 9H and 29L, 9H and 30L, 9H and 31L, 9H and 32L, 10H and 1L, 10H and 2L, 10H and 3L, 10H and 4L, 10H and 5L, 10H and 6L, 10H and 7L, 10H and 8L, 10H and 9L, 10H and 10L, 10H and 11L, 10H and 12L, 10H and 13L, 10H and 14L, 10H and 15L, 10H and 16L, 10H and 17L, 10H and 18L, 10H and 19L, 10H and 20L, 10H and 21L, 10H and 22L, 10H and 23L, 10H and 24L, 10H and 25L, 10H and 26L, 10H and 27L, 10H and 28L, 10H and 29L, 10H and 30L, 10H and 31L, 10H and 32L, 11H and 1L, 11H and 2L, 11H and 3L, 11H and 4L, 11H and 5L, 11H and 6L, 11H and 7L, 11H and 8L, 11H and 9L, 11H and 10L, 11H and 11L, 11H and 12L, 11H and 13L, 11H and 14L, 11H and 15L, 11H and 16L, 11H and 17L, 11H and 18L, 11H and 19L, 11H and 20L, 11H and 21L, 11H and 22L, 11H and 23L, 11H and 24L, 11H and 25L, 11H and 26L, 11H and 27L, 11H and 28L, 11H and 29L, 11H and 30L, 11H and 31L, 11H and 32L, 12H and 1L, 12H and 2L, 12H and 3L, 12H and 4L, 12H and 5L, 12H and 6L, 12H and 7L, 12H and 8L, 12H and 9L, 12H and 10L, 12H and 11L, 12H and 12L, 12H and 13L, 12H and 14L, 12H and 15L, 12H and 16L, 12H and 17L, 12H and 18L, 12H and 19L, 12H and 20L, 12H and 21L, 12H and 22L, 12H and 23L, 12H and 24L, 12H and 25L, 12H and 26L, 12H and 27L, 12H and 28L, 12H and 29L, 12H and 30L, 12H and 31L, 12H and 32L, 13H and 1L, 13H and 2L, 13H and 3L, 13H and 4L, 13H and 5L, 13H and 6L, 13H and 7L, 13H and 8L, 13H and 9L, 13H and 10L, 13H and 11L, 13H and 12L, 13H and 13L, 13H and 14L, 13H and 15L, 13H and 16L, 13H and 17L, 13H and 18L, 13H and 19L, 13H and 20L, 13H and 21L, 13H and 22L, 13H and 23L, 13H and 24L, 13H and 25L, 13H and 26L, 13H and 27L, 13H and 28L, 13H and 29L, 13H and 30L, 13H and 31L, 13H and 32L, 14H and 1L, 14H and 2L, 14H and 3L, 14H and 4L, 14H and 5L, 14H and 6L, 14H and 7L, 14H and 8L, 14H and 9L, 14H and 10L, 14H and 11L, 14H and 12L, 14H and 13L, 14H and 14L, 14H and 15L, 14H and 16L, 14H and 17L, 14H and 18L, 14H and 19L, 14H and 20L, 14H and 21L, 14H and 22L, 14H and 23L, 14H and 24L, 14H and 25L, 14H and 26L, 14H and 27L, 14H and 28L, 14H and 29L, 14H and 30L, 14H and 31L, 14H and 32L, 15H and 1L, 15H and 2L, 15H and 3L, 15H and 4L, 15H and 5L, 15H and 6L, 15H and 7L, 15H and 8L, 15H and 9L, 15H and 10L, 15H and 11L, 15H and 12L, 15H and 13L, 15H and 14L, 15H and 15L, 15H and 16L, 15H and 17L, 15H and 18L, 15H and 19L, 15H and 20L, 15H and 21L, 15H and 22L, 15H and 23L, 15H and 24L, 15H and 25L, 15H and 26L, 15H and 27L, 15H and 28L, 15H and 29L, 15H and 30L, 15H and 31L, 15H and 32L, 16H and 1L, 16H and 2L, 16H and 3L, 16H and 4L, 16H and 5L, 16H and 6L, 16H and 7L, 16H and 8L, 16H and 9L, 16H and 10L, 16H and 11L, 16H and 12L, 16H and 13L, 16H and 14L, 16H and 15L, 16H and 16L, 16H and 17L, 16H and 18L, 16H and 19L, 16H and 20L, 16H and 21L, 16H and 22L, 16H and 23L, 16H and 24L, 16H and 25L, 16H and 26L, 16H and 27L, 16H and 28L, 16H and 29L, 16H and 30L, 16H and 31L, 16H and 32L, 17H and 1L, 17H and 2L, 17H and 3L, 17H and 4L, 17H and 5L, 17H and 6L, 17H and 7L, 17H and 8L, 17H and 9L, 17H and 10L, 17H and 11L, 17H and 12L, 17H and 13L, 17H and 14L, 17H and 15L, 17H and 16L, 17H and 17L, 17H and 18L, 17H and 19L, 17H and 20L, 17H and 21L, 17H and 22L, 17H and 23L, 17H and 24L, 17H and 25L, 17H and 26L, 17H and 27L, 17H and 28L, 17H and 29L, 17H and 30L, 17H and 31L, 17H and 32L, 18H and 1L, 18H and 2L, 18H and 3L, 18H and 4L, 18H and 5L, 18H and 6L, 18H and 7L, 18H and 8L, 18H and 9L, 18H and 10L, 18H and 11L, 18H and 12L, 18H and 13L, 18H and 14L, 18H and 15L, 18H and 16L, 18H and 17L, 18H and 18L, 18H and 19L, 18H and 20L, 18H and 21L, 18H and 22L, 18H and 23L, 18H and 24L, 18H and 25L, 18H and 26L, 18H and 27L, 18H and 28L, 18H and 29L, 18H and 30L, 18H and 31L, 18H and 32L, 19H and 1L, 19H and 2L, 19H and 3L, 19H and 4L, 19H and 5L, 19H and 6L, 19H and 7L, 19H and 8L, 19H and 9L, 19H and 10L, 19H and 11L, 19H and 12L, 19H and 13L, 19H and 14L, 19H and 15L, 19H and 16L, 19H and 17L, 19H and 18L, 19H and 19L, 19H and 20L, 19H and 21L, 19H and 22L, 19H and 23L, 19H and 24L, 19H and 25L, 19H and 26L, 19H and 27L, 19H and 28L, 19H and 29L, 19H and 30L, 19H and 31L, 19H and 32L, 20H and 1L, 20H and 2L, 20H and 3L, 20H and 4L, 20H and 5L, 20H and 6L, 20H and 7L, 20H and 8L, 20H and 9L, 20H and 10L, 20H and 11L, 20H and 12L, 20H and 13L, 20H and 14L, 20H and 15L, 20H and 16L, 20H and 17L, 20H and 18L, 20H and 19L, 20H and 20L, 20H and 21L, 20H and 22L, 20H and 23L, 20H and 24L, 20H and 25L, 20H and 26L, 20H and 27L, 20H and 28L, 20H and 29L, 20H and 30L, 20H and 31L, 20H and 32L, 21H and 1L, 21H and 2L, 21H and 3L, 21H and 4L, 21H and 5L, 21H and 6L, 21H and 7L, 21H and 8L, 21H and 9L, 21H and 10L, 21H and 11L, 21H and 12L, 21H and 13L, 21H and 14L, 21H and 15L, 21H and 16L, 21H and 17L, 21H and 18L, 21H and 19L, 21H and 20L, 21H and 21L, 21H and 22L, 21H and 23L, 21H and 24L, 21H and 25L, 21H and 26L, 21H and 27L, 21H and 28L, 21H and 29L, 21H and 30L, 21H and 31L, 21H and 32L, 22H and 1L, 22H and 2L, 22H and 3L, 22H and 4L, 22H and 5L, 22H and 6L, 22H and 7L, 22H and 8L, 22H and 9L, 22H and 10L, 22H and 11L, 22H and 12L, 22H and 13L, 22H and 14L, 22H and 15L, 22H and 16L, 22H and 17L, 22H and 18L, 22H and 19L, 22H and 20L, 22H and 21L, 22H and 22L, 22H and 23L, 22H and 24L, 22H and 25L, 22H and 26L, 22H and 27L, 22H and 28L, 22H and 29L, 22H and 30L, 22H and 31L, 22H and 32L, 23H and 1L, 23H and 2L, 23H and 3L, 23H and 4L, 23H and 5L, 23H and 6L, 23H and 7L, 23H and 8L, 23H and 9L, 23H and 10L, 23H and 11L, 23H and 12L, 23H and 13L, 23H and 14L, 23H and 15L, 23H and 16L, 23H and 17L, 23H and 18L, 23H and 19L, 23H and 20L, 23H and 21L, 23H and 22L, 23H and 23L, 23H and 24L, 23H and 25L, 23H and 26L, 23H and 27L, 23H and 28L, 23H and 29L, 23H and 30L, 23H and 31L, 23H and 32L, 24H and 1L, 24H and 2L, 24H and 3L, 24H and 4L, 24H and 5L, 24H and 6L, 24H and 7L, 24H and 8L, 24H and 9L, 24H and 10L, 24H and 11L, 24H and 12L, 24H and 13L, 24H and 14L, 24H and 15L, 24H and 16L, 24H and 17L, 24H and 18L, 24H and 19L, 24H and 20L, 24H and 21L, 24H and 22L, 24H and 23L, 24H and 24L, 24H and 25L, 24H and 26L, 24H and 27L, 24H and 28L, 24H and 29L, 24H and 30L, 24H and 31L, 24H and 32L, 25H and 1L, 25H and 2L, 25H and 3L, 25H and 4L, 25H and 5L, 25H and 6L, 25H and 7L, 25H and 8L, 25H and 9L, 25H and 10L, 25H and 11L, 25H and 12L, 25H and 13L, 25H and 14L, 25H and 15L, 25H and 16L, 25H and 17L, 25H and 18L, 25H and 19L, 25H and 20L, 25H and 21L, 25H and 22L, 25H and 23L, 25H and 24L, 25H and 25L, 25H and 26L, 25H and 27L, 25H and 28L, 25H and 29L, 25H and 30L, 25H and 31L, 25H and 32L, 26H and 1L, 26H and 2L, 26H and 3L, 26H and 4L, 26H and 5L, 26H and 6L, 26H and 7L, 26H and 8L, 26H and 9L, 26H and 10L, 26H and 11L, 26H and 12L, 26H and 13L, 26H and 14L, 26H and 15L, 26H and 16L, 26H and 17L, 26H and 18L, 26H and 19L, 26H and 20L, 26H and 21L, 26H and 22L, 26H and 23L, 26H and 24L, 26H and 25L, 26H and 26L, 26H and 27L, 26H and 28L, 26H and 29L, 26H and 30L, 26H and 31L, 26H and 32L, 27H and 1L, 27H and 2L, 27H and 3L, 27H and 4L, 27H and 5L, 27H and 6L, 27H and 7L, 27H and 8L, 27H and 9L, 27H and 10L, 27H and 11L, 27H and 12L, 27H and 13L, 27H and 14L, 27H and 15L, 27H and 16L, 27H and 17L, 27H and 18L, 27H and 19L, 27H and 20L, 27H and 21L, 27H and 22L, 27H and 23L, 27H and 24L, 27H and 25L, 27H and 26L, 27H and 27L, 27H and 28L, 27H and 29L, 27H and 30L, 27H and 31L, 27H and 32L, 28H and 1L, 28H and 2L, 28H and 3L, 28H and 4L, 28H and 5L, 28H and 6L, 28H and 7L, 28H and 8L, 28H and 9L, 28H and 10L, 28H and 11L, 28H and 12L, 28H and 13L, 28H and 14L, 28H and 15L, 28H and 16L, 28H and 17L, 28H and 18L, 28H and 19L, 28H and 20L, 28H and 21L, 28H and 22L, 28H and 23L, 28H and 24L, 28H and 25L, 28H and 26L, 28H and 27L, 28H and 28L, 28H and 29L, 28H and 30L, 28H and 31L, 28H and 32L, 29H and 1L, 29H and 2L, 29H and 3L, 29H and 4L, 29H and 5L, 29H and 6L, 29H and 7L, 29H and 8L, 29H and 9L, 29H and 10L, 29H and 11L, 29H and 12L, 29H and 13L, 29H and 14L, 29H and 15L, 29H and 16L, 29H and 17L, 29H and 18L, 29H and 19L, 29H and 20L, 29H and 21L, 29H and 22L, 29H and 23L, 29H and 24L, 29H and 25L, 29H and 26L, 29H and 27L, 29H and 28L, 29H and 29L, 29H and 30L, 29H and 31L, 29H and 32L, 30H and 1L, 30H and 2L, 30H and 3L, 30H and 4L, 30H and 5L, 30H and 6L, 30H and 7L, 30H and 8L, 30H and 9L, 30H and 10L, 30H and 11L, 30H and 12L, 30H and 13L, 30H and 14L, 30H and 15L, 30H and 16L, 30H and 17L, 30H and 18L, 30H and 19L, 30H and 20L, 30H and 21L, 30H and 22L, 30H and 23L, 30H and 24L, 30H and 25L, 30H and 26L, 30H and 27L, 30H and 28L, 30H and 29L, 30H and 30L, 30H and 31L, 30H and 32L, 31H and 1L, 31H and 2L, 31H and 3L, 31H and 4L, 31H and 5L, 31H and 6L, 31H and 7L, 31H and 8L, 31H and 9L, 31H and 10L, 31H and 11L, 31H and 12L, 31H and 13L, 31H and 14L, 31H and 15L, 31H and 16L, 31H and 17L, 31H and 18L, 31H and 19L, 31H and 20L, 31H and 21L, 31H and 22L, 31H and 23L, 31H and 24L, 31H and 25L, 31H and 26L, 31H and 27L, 31H and 28L, 31H and 29L, 31H and 30L, 31H and 31L, 31H and 32L, 32H and 1L, 32H and 2L, 32H and 3L, 32H and 4L, 32H and 5L, 32H and 6L, 32H and 7L, 32H and 8L, 32H and 9L, 32H and 10L, 32H and 11L, 32H and 12L, 32H and 13L, 32H and 14L, 32H and 15L, 32H and 16L, 32H and 17L, 32H and 18L, 32H and 19L, 32H and 20L, 32H and 21L, 32H and 22L, 32H and 23L, 32H and 24L, 32H and 25L, 32H and 26L, 32H and 27L, 32H and 28L, 32H and 29L, 32H and 30L, 32H and 31L, or 32H and 32L.
36. The isolated antibody of any one of the preceding embodiments, wherein the antibody is humanized.
37. The isolated antibody of the of any one of the preceding embodiments, wherein the antibody is chimeric or fused to a non-antibody protein.
38. The isolated antibody of any one of the preceding embodiments, wherein the antibody does not significantly bind to claudin 9.
39. The isolated antibody of any one of the preceding embodiments, wherein the antibody binds to the claudin 6 with an affinity, $EC_{50}$, or $K_D$ at least 100, 200, or 300 times greater than it binds to claudin 9.
40. The isolated antibody of any one of the preceding embodiments, wherein the, CDR amino acid sequence, VL or VH peptide is at least, or about 90-99% identical to a sequence as provided herein or the sequence has 1, 2, 3, 4, or 5 substitutions.
41. A peptide comprising, consisting of, or consisting essentially of a sequence as provided herein, or a variant thereof.
42. The peptide of embodiment 41, wherein the peptide is a CDR, VL, or VH peptide.
43. The peptide of embodiment 41, wherein the peptide comprises, consists of, or consists essentially of a sequence of SEQ ID NO: 2-138, or a variant thereof or as otherwise provided for herein.
44. A peptide comprising, consisting of, or consisting essentially of a sequence that is 90-99% identical to a sequence as provided herein.
45. The peptide of embodiment 44, wherein peptide comprises a 1, 2, 3, 4, or 5 substitutions, deletions, or insertions as compared to a sequence as provided herein.
46. The peptide of embodiments 44 or 45, wherein the peptide is a CDR, VL, or VH peptide. 47. The peptide of embodiment 44 or 45, wherein the sequence provided herein comprises a sequence of SEQ ID NO: 2-135, or a variant thereof, or as otherwise provided for herein.
48. An antibody, such as a monoclonal antibody or scFv, that binds to an epitope on Claudin 6 whose residues include T33, N38, D68, P74, D76, D146, V152, A153, E154, Q156, R158, or any combination thereof.
49. An antibody, such as a monoclonal antibody or a scFv, that binds preferentially to Claudin 6 as compared to Claudin 9, wherein the antibody binds to an epitope on Claudin 6 that comprises Q156.
50. A bi-specific antibody comprising a first $V_H$ peptide that binds to Claudin 6 and second $V_H$ peptide that binds to a different moiety.
51. The antibody of embodiment 46, wherein the second $V_H$ peptide binds to CD3 or 4-1BB.
52. The antibody of embodiments 50 or 51, wherein the antibody is a bi-specific antibody or where the antibody is fusion protein.
53. The antibody of embodiments 50-52, further comprising a linker domain that links the antibody that binds to claudin 6 and the second $V_H$ peptide.
54. The antibody of any one of embodiments 50-53, wherein the linker domain comprises 1, 2, 3, 4, or 5, or more GGGGS (SEQ ID NO: 137) repeats.
55. The antibody of any one of embodiments 50-54, wherein the antibody comprises heavy chain CDR1, CDR2, and CDR3 sequences, wherein the heavy chain CDR1 sequence has the amino acid sequence of SEQ ID NO: 25, 31, 37, 43, 53, 55, 56, 62, 71, 76, 80, 90, or 95; the heavy chain CDR2 has the amino acid sequence of SEQ ID NO: 26, 32, 38, 44, 46, 48, 49, 54, 125, 72, 77, 81, 86, 91, 96, 101, or 102 and the heavy chain CDR3 sequence has the amino acid sequence of SEQ ID NO: 27, 33, 39, 45, 57, 61, 63, 65, 66, 67, 126, 69, 73, 82, 57, 92, or 97 or variants of any of the foregoing.
56. The antibody of any one of embodiments 50-55, wherein the antibody comprises:
a heavy chain variable region comprising heavy chain CDR1, CDR2, and CDR3 sequences, wherein the heavy chain CDR1 sequence has the amino acid sequence of SEQ ID NO: 25; the heavy chain CDR2 has the amino acid sequence of SEQ ID NO: 26; and the heavy chain CDR3 sequence has the amino acid sequence of SEQ ID NO: 27, or variants of any of the foregoing;
a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 32; and the heavy chain CDR3 sequence has the amino acid sequence of SEQ ID NO: 33, or variants of any of the foregoing;
a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 38; and the heavy chain CDR3 sequence has the amino acid sequence of SEQ ID NO: 39, or variants of any of the foregoing;
a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 44; and the heavy chain CDR3 sequence has the amino acid sequence of SEQ ID NO: 45, or variants of any of the foregoing;

a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 46; and the heavy chain CDR3 sequence has the amino acid sequence of SEQ ID NO: 33, or variants of any of the foregoing;

a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 48; and the heavy chain CDR3 sequence has the amino acid sequence of SEQ ID NO: 39, or variants of any of the foregoing;

a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 49; and the heavy chain CDR3 sequence has the amino acid sequence of SEQ ID NO: 45, or variants of any of the foregoing;

a heavy chain variable region comprising heavy chain CDR1, CDR2, and CDR3 sequences, wherein the heavy chain CDR1 sequence has the amino acid sequence of SEQ ID NO: 53; the heavy chain CDR2 has the amino acid sequence of SEQ ID NO: 54; and the heavy chain CDR3 sequence has the amino acid sequence of SEQ ID NO: 33, or variants of any of the foregoing;

a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 54; and the heavy chain CDR3 sequence has the amino acid sequence of SEQ ID NO: 33, or variants of any of the foregoing;

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 125; and the heavy chain CDR3 sequence has the amino acid sequence of SEQ ID NO: 61, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 63, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 66, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 67, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 126, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69, or variants of any of the foregoing;

a heavy chain variable region comprising heavy chain CDR1, CDR2, and CDR3 sequences, wherein the heavy chain CDR1 sequence has the amino acid sequence of SEQ ID NO: 71; the heavy chain CDR2 has the amino acid sequence of SEQ ID NO: 72; and the heavy chain CDR3 sequence has the amino acid sequence of SEQ ID NO: 73, or variants of any of the foregoing;

a heavy chain variable region comprising heavy chain CDR1, CDR2, and CDR3 sequences, wherein the heavy chain CDR1 sequence has the amino acid sequence of SEQ ID NO: 76; the heavy chain CDR2 has the amino acid sequence of SEQ ID NO: 77; and the heavy chain CDR3 sequence has the amino acid sequence of SEQ ID NO: 78, or variants of any of the foregoing;

a heavy chain variable region comprising heavy chain CDR1, CDR2, and CDR3 sequences, wherein the heavy chain CDR1 sequence has the amino acid sequence of SEQ ID NO: 80; the heavy chain CDR2 has the amino acid sequence of SEQ ID NO: 81; and the heavy chain CDR3 sequence has the amino acid sequence of SEQ ID NO: 82, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 86; and the heavy chain CDR3 sequence has the amino acid sequence of SEQ ID NO: 57, or variants of any of the foregoing;

a heavy chain variable region comprising heavy chain CDR1, CDR2, and CDR3 sequences, wherein the heavy chain CDR1 sequence has the amino acid sequence of SEQ ID NO: 90; the heavy chain CDR2 has the amino acid sequence of SEQ ID NO: 91; and the heavy chain CDR3 sequence has the amino acid sequence of SEQ ID NO: 92, or variants of any of the foregoing;

a heavy chain variable region comprising heavy chain CDR1, CDR2, and CDR3 sequences, wherein the heavy chain CDR1 sequence has the amino acid sequence of SEQ ID NO: 95; the heavy chain CDR2 has the amino acid sequence of SEQ ID NO: 96; and the heavy chain CDR3 sequence has the amino acid sequence of SEQ ID NO: 97, or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 101; and the heavy chain CDR3 sequence has the amino acid sequence of SEQ ID NO: 57, or variants of any of the foregoing; or a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 102; and the heavy chain CDR3 sequence has the amino acid sequence of SEQ ID NO: 57, or variants of any of the foregoing.

57. The antibody of any one of embodiments 50-56, wherein the antibody comprises a light chain variable region comprising a sequence of any one of sequences as set forth in SEQ ID NOs: 127-135.

58. The antibody of any one of embodiments 50-56, wherein the antibody comprises a light chain variable region comprising light chain CDR1, CDR2, and CDR3 sequences, wherein the light chain CDR1 sequence has the amino acid sequence of SEQ ID NO: 22, 28, 34, 40, 47, 50, 58, 64, 74, 83, 87, 93, or 98; the light chain CDR2 sequence has the amino acid sequence of SEQ ID NO: 23, 29, 41, 51, 59, 68, 84, 88, or 99, and the light chain CDR3 sequence has the amino acid sequence of SEQ ID NO: 24, 30, 36, 42, 52, 60, 70, 75, 79, 85, 89, 94, or variants of any of the foregoing.

59. The antibody of any one of embodiments 50-56, wherein antibody comprises:

a light chain variable region comprising light chain CDR1, CDR2, and CDR3 sequences, wherein the light chain CDR1 sequence has the amino acid sequence SEQ ID NO: 22; the light chain CDR2 sequence has the amino acid sequence of SEQ ID NO: 23, and the light chain CDR3 sequence has the amino acid sequence of SEQ ID NO: 24, or variants of any of the foregoing;

a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29, and the light chain CDR3 sequence has the amino acid sequence of SEQ ID NO: 30, or variants of any of the foregoing;

a light chain variable region comprising light chain CDR1, CDR2, and CDR3 sequences, wherein the light chain CDR1 sequence has the amino acid sequence SEQ ID NO: 34; the light chain CDR2 sequence has the amino acid sequence of SEQ ID NO: 29, and the light chain CDR3 sequence has the amino acid sequence of SEQ ID NO: 36, or variants of any of the foregoing;

a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41, and the light chain CDR3 sequence has the amino acid sequence of SEQ ID NO: 42, or variants of any of the foregoing;

a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 29, and the light chain CDR3 sequence has the amino acid sequence of SEQ ID NO: 36, or variants of any of the foregoing;

a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51, and the light chain CDR3 sequence has the amino acid sequence of SEQ ID NO: 52, or variants of any of the foregoing;

a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68, and the light chain CDR3 sequence has the amino acid sequence of SEQ ID NO: 60, or variants of any of the foregoing;

a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59, and the light chain CDR3 sequence has the amino acid sequence of SEQ ID NO: 70, or variants of any of the foregoing;

a light chain variable region comprising light chain
CDR1, CDR2, and CDR3 sequences, wherein the
light chain CDR1 sequence has the amino acid
sequence SEQ ID NO: 74; the light chain CDR2
sequence has the amino acid sequence of SEQ ID
NO: 59, and the light chain CDR3 sequence has the
amino acid sequence of SEQ ID NO: 75, or variants
of any of the foregoing;
a light chain variable region comprising light chain
CDR1, CDR2, and CDR3 sequences, wherein the
light chain CDR1 sequence has the amino acid
sequence SEQ ID NO: 58; the light chain CDR2
sequence has the amino acid sequence of SEQ ID
NO: 59, and the light chain CDR3 sequence has the
amino acid sequence of SEQ ID NO: 79, or variants
of any of the foregoing;
a light chain variable region comprising light chain
CDR1, CDR2, and CDR3 sequences, wherein the
light chain CDR1 sequence has the amino acid
sequence SEQ ID NO: 83; the light chain CDR2
sequence has the amino acid sequence of SEQ ID
NO: 84, and the light chain CDR3 sequence has the
amino acid sequence of SEQ ID NO: 85, or variants
of any of the foregoing;
a light chain variable region comprising light chain
CDR1, CDR2, and CDR3 sequences, wherein the
light chain CDR1 sequence has the amino acid
sequence SEQ ID NO: 87; the light chain CDR2
sequence has the amino acid sequence of SEQ ID
NO: 88, and the light chain CDR3 sequence has the
amino acid sequence of SEQ ID NO: 89, or variants
of any of the foregoing;
a light chain variable region comprising light chain
CDR1, CDR2, and CDR3 sequences, wherein the
light chain CDR1 sequence has the amino acid
sequence SEQ ID NO: 93; the light chain CDR2
sequence has the amino acid sequence of SEQ ID
NO: 88, and the light chain CDR3 sequence has the
amino acid sequence of SEQ ID NO: 94, or variants
of any of the foregoing; or a light chain variable
region comprising light chain CDR1, CDR2, and
CDR3 sequences, wherein the light chain CDR1
sequence has the amino acid sequence SEQ ID NO:
98; the light chain CDR2 sequence has the amino
acid sequence of SEQ ID NO: 99, and the light chain
CDR3 sequence has the amino acid sequence of SEQ
ID NO: 100, or variants of any of the foregoing.
60. The antibody of any one of embodiments 50-56, or
antigen binding fragment thereof, wherein the antibody, or antigen binding fragment thereof, comprises:
(i) a heavy chain variable region comprising heavy
chain CDR1, CDR2, and CDR3 sequences, wherein
the heavy chain CDR1 sequence has the amino acid
sequence of SEQ ID NO: 25, 31, 37, 43, 53, 55, 56,
62, 71, 76, 80, 90, or 95; the heavy chain CDR2 has
the amino acid sequence of 26, 32, 38, 44, 46, 48, 49,
54, 125, 72, 77, 81, 86, 91, 96, 101, or 102 and the
heavy chain CDR3 sequence has the amino acid
sequence of SEQ ID NO: 27, 33, 39, 45, 57, 61, 63,
65, 66, 67, 126, 69, 73, 82, 57, 92, or 97 or variants
of any of the foregoing; and
(ii) a light chain variable region comprising light chain
CDR1, CDR2, and CDR3 sequences, wherein the
light chain CDR1 sequence has the amino acid
sequence 22, 28, 34, 40, 47, 50, 58, 64, 74, 83, 87,
93, or 98; the light chain CDR2 sequence has the
amino acid sequence of 23, 29, 41, 51, 59, 68, 84, 88,
or 99, and the light chain CDR3 sequence has the
amino acid sequence of 24, 30, 36, 42, 52, 60, 70, 75,
79, 85, 89, 94, or variants of any of the foregoing.
61. The antibody of any one of embodiments 50-56,
wherein the antibody, or antigen binding fragment
thereof, comprises:
a heavy chain variable region comprising heavy chain
CDR1, CDR2, and CDR3 sequences, wherein the
heavy chain CDR1 sequence has the amino acid
sequence of SEQ ID NO: 56; the heavy chain CDR2
has the amino acid sequence of SEQ ID NO: 125;
and the heavy chain CDR3 sequence has the amino
acid sequence of SEQ ID NO: 57; or variants of any
of the foregoing; and a light chain variable region
comprising light chain CDR1, CDR2, and CDR3
sequences, wherein the light chain CDR1 sequence
has the amino acid sequence SEQ ID NO: 58; the
light chain CDR2 sequence has the amino acid
sequence of SEQ ID NO: 59; and the light chain
CDR3 sequence has the amino acid sequence of SEQ
ID NO: 60; or variants of any of the foregoing;
a heavy chain variable region comprising heavy chain
CDR1, CDR2, and CDR3 sequences, wherein the
heavy chain CDR1 sequence has the amino acid
sequence of SEQ ID NO: 56; the heavy chain CDR2
has the amino acid sequence of SEQ ID NO: 125;
and the heavy chain CDR3 sequence has the amino
acid sequence of SEQ ID NO: 61; or variants of any
of the foregoing; and a light chain variable region
comprising light chain CDR1, CDR2, and CDR3
sequences, wherein the light chain CDR1 sequence
has the amino acid sequence SEQ ID NO: 58; the
light chain CDR2 sequence has the amino acid
sequence of SEQ ID NO: 59; and the light chain
CDR3 sequence has the amino acid sequence of SEQ
ID NO: 60; or variants of any of the foregoing;
a heavy chain variable region comprising heavy chain
CDR1, CDR2, and CDR3 sequences, wherein the
heavy chain CDR1 sequence has the amino acid
sequence of SEQ ID NO: 62; the heavy chain CDR2
has the amino acid sequence of SEQ ID NO: 125;
and the heavy chain CDR3 sequence has the amino
acid sequence of SEQ ID NO: 63; or variants of any
of the foregoing; and a light chain variable region
comprising light chain CDR1, CDR2, and CDR3
sequences, wherein the light chain CDR1 sequence
has the amino acid sequence SEQ ID NO: 64; the
light chain CDR2 sequence has the amino acid
sequence of SEQ ID NO: 59; and the light chain
CDR3 sequence has the amino acid sequence of SEQ
ID NO: 60; or variants of any of the foregoing;
a heavy chain variable region comprising heavy chain
CDR1, CDR2, and CDR3 sequences, wherein the
heavy chain CDR1 sequence has the amino acid
sequence of SEQ ID NO: 62; the heavy chain CDR2
has the amino acid sequence of SEQ ID NO: 125;
and the heavy chain CDR3 sequence has the amino
acid sequence of SEQ ID NO: 65; or variants of any
of the foregoing; and a light chain variable region
comprising light chain CDR1, CDR2, and CDR3
sequences, wherein the light chain CDR1 sequence
has the amino acid sequence SEQ ID NO: 64; the
light chain CDR2 sequence has the amino acid
sequence of SEQ ID NO: 59; and the light chain
CDR3 sequence has the amino acid sequence of SEQ
ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 66; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 67; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 65; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 126; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 68; and the light chain CDR3 sequence has the amino acid sequence of SEQ ID NO: 60; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 125; and the heavy chain CDR3 sequence has the amino acid sequence of SEQ ID NO: 69; or variants of any of the foregoing; and a light chain variable region comprising light chain CDR1, CDR2, and CDR3 sequences, wherein the light chain CDR1 sequence has the amino acid sequence SEQ ID NO: 64; the light chain CDR2 sequence has the amino acid sequence of SEQ ID NO: 59; and the light chain CDR3 sequence has the amino acid sequence of SEQ ID NO: 70; or variants of any of the foregoing;

a heavy chain variable region comprising heavy chain CDR1, CDR2, and CDR3 sequences, wherein the heavy chain CDR1 sequence has the amino acid sequence of SEQ ID NO: 71; the heavy chain CDR2 has the amino acid sequence of SEQ ID NO: 72; and the heavy chain CDR3 sequence has the amino acid sequence of SEQ ID NO: 73; or variants of any of the foregoing; and a light chain variable region comprising light chain CDR1, CDR2, and CDR3 sequences, wherein the light chain CDR1 sequence has the amino acid sequence SEQ ID NO: 74; the light chain CDR2 sequence has the amino acid sequence of SEQ ID NO: 59; and the light chain CDR3 sequence has the amino acid sequence of SEQ ID NO: 75; or variants of any of the foregoing;

a heavy chain variable region comprising heavy chain CDR1, CDR2, and CDR3 sequences, wherein the heavy chain CDR1 sequence has the amino acid sequence of SEQ ID NO: 76; the heavy chain CDR2 has the amino acid sequence of SEQ ID NO: 77; and the heavy chain CDR3 sequence has the amino acid sequence of SEQ ID NO: 78; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 79; or variants of any of the foregoing;

a heavy chain variable region comprising heavy chain CDR1, CDR2, and CDR3 sequences, wherein the heavy chain CDR1 sequence has the amino acid sequence of SEQ ID NO: 80; the heavy chain CDR2 has the amino acid sequence of SEQ ID NO: 81; and the heavy chain CDR3 sequence has the amino acid sequence of SEQ ID NO: 82; or variants of any of the foregoing; and a light chain variable region comprising light chain CDR1, CDR2, and CDR3 sequences, wherein the light chain CDR1 sequence has the amino acid sequence SEQ ID NO: 83; the light chain CDR2 sequence has the amino acid sequence of SEQ ID NO: 84; and the light chain CDR3 sequence has the amino acid sequence of SEQ ID NO: 85; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 86; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88; and the light chain CDR3 sequence has the amino acid sequence of SEQ ID NO: 89; or variants of any of the foregoing;

a heavy chain variable region comprising heavy chain CDR1, CDR2, and CDR3 sequences, wherein the heavy chain CDR1 sequence has the amino acid sequence of SEQ ID NO: 90; the heavy chain CDR2 has the amino acid sequence of SEQ ID NO: 91; and the heavy chain CDR3 sequence has the amino acid sequence of SEQ ID NO: 92; or variants of any of the foregoing; and a light chain variable region comprising light chain CDR1, CDR2, and CDR3 sequences, wherein the light chain CDR1 sequence has the amino acid sequence SEQ ID NO: 93; the light chain CDR2 sequence has the amino acid sequence of SEQ ID NO: 88; and the light chain CDR3 sequence has the amino acid sequence of SEQ ID NO: 94; or variants of any of the foregoing;

a heavy chain variable region comprising heavy chain CDR1, CDR2, and CDR3 sequences, wherein the heavy chain CDR1 sequence has the amino acid sequence of SEQ ID NO: 95; the heavy chain CDR2 has the amino acid sequence of SEQ ID NO: 96; and the heavy chain CDR3 sequence has the amino acid sequence of SEQ ID NO: 97; or variants of any of the foregoing; and a light chain variable region comprising light chain CDR1, CDR2, and CDR3 sequences, wherein the light chain CDR1 sequence has the amino acid sequence SEQ ID NO: 98; the light chain CDR2 sequence has the amino acid sequence of SEQ ID NO: 99; and the light chain CDR3 sequence has the amino acid sequence of SEQ ID NO: 100; or variants of any of the foregoing;

a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 101; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing; or a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 102; and the heavy chain CDR3 sequence has the amino acid sequence of SEQ ID NO: 57; or variants of any of the foregoing; and a light chain variable region comprising light chain CDR1, CDR2, and CDR3 sequences, wherein the light chain CDR1 sequence has the amino acid sequence SEQ ID NO: 87; the light chain CDR2 sequence has the amino acid sequence of SEQ ID NO: 88; and the light chain CDR3 sequence has the amino acid sequence of SEQ ID NO: 89; or variants of any of the foregoing;

a heavy chain variable region comprising heavy chain CDR1, CDR2, and CDR3 sequences, wherein the heavy chain CDR1 sequence has the amino acid sequence of SEQ ID NO: 25; the heavy chain CDR2 has the amino acid sequence of SEQ ID NO: 26; and the heavy chain CDR3 sequence has the amino acid sequence of SEQ ID NO: 27; or variants of any of the foregoing; and a light chain variable region comprising light chain CDR1, CDR2, and CDR3 sequences, wherein the light chain CDR1 sequence has the amino acid sequence SEQ ID NO: 22; the light chain CDR2 sequence has the amino acid sequence of SEQ ID NO: 23; and the light chain CDR3 sequence has the amino acid sequence of SEQ ID NO: 24; or variants of any of the foregoing;

a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 32; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29; and the light chain CDR3 sequence has the amino acid sequence of SEQ ID NO: 30; or variants of any of the foregoing;

a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 28; and the heavy chain CDR3 sequence has the amino acid sequence of SEQ ID NO: 29; or variants of any of the foregoing; and a light chain variable region comprising light chain CDR1, CDR2, and CDR3 sequences, wherein the light chain CDR1 sequence has the amino acid sequence SEQ ID NO: 34; the light chain CDR2 sequence has the amino acid sequence of SEQ ID NO: 29; and the light chain CDR3 sequence has the amino acid sequence of SEQ ID NO: 26; or variants of any of the foregoing;

a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 44; and the heavy chain CDR3 sequence has the amino acid sequence of SEQ ID NO: 45; or variants of any of the foregoing; and a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41; and the light chain CDR3 sequence has the amino acid sequence of SEQ ID NO: 42; or variants of any of the foregoing;

a heavy chain variable region comprising heavy chain CDR1, CDR2, and CDR3 sequences, wherein the heavy chain CDR1 sequence has the amino acid sequence of SEQ ID NO: 31; the heavy chain CDR2 has the amino acid sequence of SEQ ID NO: 46; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 28; the light chain CDR2 sequence has the amino acid sequence of SEQ ID NO: 29; and the light chain CDR3 sequence has the amino acid sequence of SEQ ID NO: 30; or variants of any of the foregoing;

a heavy chain variable region comprising heavy chain CDR1, CDR2, and CDR3 sequences, wherein the heavy chain CDR1 sequence has the amino acid sequence of SEQ ID NO: 37; the heavy chain CDR2 has the amino acid sequence of SEQ ID NO: 48; and the heavy chain CDR3 sequence has the amino acid sequence of SEQ ID NO: 39; or variants of any of the foregoing; and a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 29; and the light chain CDR3 sequence has the amino acid sequence of SEQ ID NO: 36; or variants of any of the foregoing;

a heavy chain variable region comprising heavy chain CDR1, CDR2, and CDR3 sequences, wherein the heavy chain CDR1 sequence has the amino acid sequence of SEQ ID NO: 43; the heavy chain CDR2 has the amino acid sequence of SEQ ID NO: 49; and the heavy chain CDR3 sequence has the amino acid sequence of SEQ ID NO: 45; or variants of any of the foregoing; and a light chain variable region comprising light chain CDR1, CDR2, and CDR3 sequences, wherein the light chain CDR1 sequence has the amino acid sequence SEQ ID NO: 40; the light chain CDR2 sequence has the amino acid sequence of SEQ ID NO: 41; and the light chain CDR3 sequence has the amino acid sequence of SEQ ID NO: 42; or variants of any of the foregoing;

a heavy chain variable region comprising heavy chain CDR1, CDR2, and CDR3 sequences, wherein the heavy chain CDR1 sequence has the amino acid sequence of SEQ ID NO: 53; the heavy chain CDR2 has the amino acid sequence of SEQ ID NO: 54; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51; and the light chain CDR3 sequence has the amino acid sequence of SEQ ID NO: 52; or variants of any of the foregoing;

a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 54; and the heavy chain CDR3 sequence has the amino acid sequence of SEQ ID NO: 33; or variants of any of the foregoing; and a light chain variable region comprising light chain CDR1, CDR2, and CDR3 sequences, wherein the light chain CDR1 sequence has the amino acid sequence SEQ ID NO: 50; the light chain CDR2 sequence has the amino acid sequence of SEQ ID NO: 51; and the light chain CDR3 sequence has the amino acid sequence of SEQ ID NO: 52; or variants of any of the foregoing;

62. A nucleic acid molecule encoding an antibody or an amino acid sequence of any of the preceding embodiments.

63. A vector comprising the nucleic acid molecule of embodiment 62.

64. A cell comprising the nucleic comprising the nucleic acid molecule of embodiment 62 or the vector of embodiment 63.

65. A pharmaceutical composition comprising the isolated antibody of any one of embodiments 1-61 or a nucleic acid molecule encoding the same.

66. The pharmaceutical composition of embodiment 65, wherein the composition is an injectable pharmaceutical composition.

67. The pharmaceutical compositions of embodiments 65 or 66, wherein the composition is sterile.

68. The pharmaceutical compositions of any one of embodiments 65-67, wherein the composition is pyrogen free.

69. The pharmaceutical compositions of any one of embodiments 65-68, wherein the composition is free of antibodies that do not bind to Claudin 6.

70. A method of modulating Claudin 6 activity by contacting a cell expressing Claudin 6 with a Claudin 6 antibody or a pharmaceutical composition comprising the same that binds to Claudin 6 on the cell surface.

71. The method of embodiment 70, wherein the antibody is any of the antibodies provided for herein or an antibody of any one of embodiments 1-61 or a nucleic acid molecule encoding the same.

72. A method for inhibiting the function of Claudin 6 by contacting a cell expressing Claudin 6 with an antibody or a pharmaceutical composition comprising the same that inhibits the function of Claudin 6 by binding to Claudin 6.

73. The method of embodiment 61, wherein the antibody is any of the antibodies provided for herein or an antibody of any one of embodiments 1-61 or a nucleic acid molecule encoding the same.

74. The method of embodiment 72, wherein the antibody is an antibody or peptide of any one of embodiments 1-61.

75. The method of any of one of embodiments 72-74, wherein the antibody is administered to a subject in need of such antibody.

76. The method of embodiment 75, wherein the function is regulation of the tight junction integrity.

77. A method of treating a subject with a Claudin 6 mediated disorder, the method comprising administering a pharmaceutical composition comprising a Claudin 6 antibody to the subject, such as any antibody provided herein or an antibody of any one of embodiments 1-61 or a nucleic acid molecule encoding the same.

78. The method of embodiment 77, wherein the disorder is benign or metastatic cancer, for example, ovarian cancer (e.g., ovarian carcinoma), reproductive cancer (breast, cervical, testicular, uterine, or placental cancer), lung cancer, gastric cancer, hepatic cancer, pancreatic cancer, bile duct cancer, cancer of the urinary bladder, kidney cancer, colon cancer, small bowel cancer, skin cancer, head and neck cancer, sarcoma, or germ cell tumor.
79. The method of embodiments 77 or 78, wherein the antibody is an antibody of any of one of embodiments 1-61 or a nucleic acid molecule encoding the same or a pharmaceutical composition comprising the antibody or the nucleic acid molecule encoding the same.
80. A method of treating cancer in a subject, the method comprising administering a therapeutic that specifically binds to claudin 6 and binds to CD3 and/or 4-1BB.
81. The method of embodiment 80, wherein the therapeutic comprises an antibody of any one of embodiments 1-61 or a nucleic acid molecule encoding the same.
82. A method of treating cancer in a subject, the method comprising administering to the subject a pharmaceutical composition comprising an antibody that binds to residue Q156 of Claudin 6 or nucleic acid molecule encoding the same.
83. The method of embodiment 77, wherein the antibody comprises a CDR, VL, or VH as provided herein or a sequence of SEQ ID NO: 2-135.
84. The method of embodiments 82 or 83, wherein the antibody is a hexabody.
85. The method of embodiment 82, wherein the pharmaceutical composition comprises a chimeric receptor, such as a chimeric antigen receptor (CAR), wherein the receptor comprises an extracellular antibody domain that comprises an antibody of any one of embodiments 1-61 or an antibody that binds to residue Q156 of Claudin 6.
86. The method of embodiment 85, wherein the chimeric receptor comprises a transmembrane domain and an intracellular domain.
87. The method of embodiments 85 and 86, wherein a cell comprises the chimeric receptor.
88. The method of embodiment 87, wherein the cell is an immune cell, such as a T-cell, macrophage, dendritic cell, NK cell, and the like.
89. A multi-specific antibody, wherein the multi-specific antibody comprises an antibody domain as provided herein.
90. The multi-specific antibody of embodiment 89, wherein the antibody domain comprises an antibody, CDR, VL, or VH peptide as provided herein or according to any one of embodiments 1-61.
91. A chimeric receptor comprising an antibody domain as provided herein.
92. The chimeric receptor of embodiment 91, wherein the antibody domain comprises an antibody, CDR, VL, or VH peptide as provided herein or according to any one of embodiments 1-61.
93. A composition comprising an antibody of any one of embodiments 1-61 or an antibody domain as provided herein linked to a drug or other therapeutic.
94. The composition of embodiment 93, wherein the therapeutic is a cytokine, such as IL-2.
95. The composition of embodiment 93, wherein the composition is an antibody drug conjugate (ADC).
96. The composition of any one of embodiments 93-95, wherein the antibody domain comprises an antibody, CDR, VL, or VH peptide as provided herein or according to any one of embodiments 1-61.
97. A hexabody comprising an antibody domain as provided herein.
98. The hexabody of embodiment 97, wherein the antibody domain comprises an antibody, CDR, VL, or VH peptide as provided herein or according to any one of embodiments 1-61 or a sequence comprising one or more sequences of SEQ ID NO: 2-135.
99. A composition comprising a peptide as provided herein, such as a peptide comprising one or more sequences of SEQ ID NO: 2-135.
100. The composition of embodiment 99, wherein the peptide is an antibody, CDR, VL, or VH peptide as provided herein or is a peptide or antibody according to any one of embodiments 1-61.
101. A method of detecting the presence or absence of Claudin 6 in a sample comprising contacting a sample with an antibody as provided herein and any of the preceding embodiments and detecting the binding to a Claudin 6 antigen by the antibody, wherein the detection of the binding indicates the presence Claudin 6; or the absence of the detection of the binding to the Claudin 6 indicates the absence of the Claudin 6.
102. A method of delivering a composition to a cell expressing Claudin 6, the method comprising contacting a cell with an antibody as provided herein or an antibody of any one of embodiments 1-61, wherein the antibody is linked to another molecule to be delivered to the cell expressing Claudin 6.
103. The method of embodiment 102, wherein the antibody is an antibody, CDR, VL, or VH peptide as provided herein or is a peptide or antibody according to any one of embodiments 1-61, or comprising one or more sequences of SEQ ID NO: 2-135.
104. The methods of embodiments 102 or 103, wherein the other molecule is a drug.
105. A method of contacting a composition to a cell expressing Claudin 6, the method comprising contacting a cell with an antibody as provided herein, wherein the antibody is linked to another molecule to contact with the cell expressing Claudin 6.
106. The method of embodiment 105, wherein the antibody is an antibody, CDR, VL, or VH peptide as provided herein or is a peptide or antibody according to any one of embodiments 1-61, or comprising one or more sequences of SEQ ID NO: 2-135.
107. The methods of embodiments 105 or 106, wherein the other molecule is a drug.
108. The method of any one of embodiments 105-107, wherein the cell expressing claudin 6 is in a subject.
109. The method of any one of embodiments 105-108, wherein the cell is a tumor cell.
110. The method of embodiment 109, wherein the tumor cell is a solid tumor cell.
111. The method of embodiment 110, wherein the tumor cell is an ovarian tumor cell, non-small cell lung tumor cell, teratoma tumor cell, a gastric tumor cell, a lung tumor cell, a breast tumor cell, or a colon tumor cell or other type of tumor or cancer cell provided for herein.

As provided for herein, the DNA (or RNA sequences) that may encode a protein may vary due to the degeneracy of the genetic code. Such variants are encompassed by the embodiments provided for herein.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Claudin 6 Antibodies Bind to Claudin 6

FIG. 1 illustrates the results of a binding assay showing that Claudin 6 MAbs bind to human Claudin 6. Human embryonic kidney 293T (HEK-293T) cells were transiently transfected with DNA for human Claudin 6 (hsCLDN6) or empty vector along with GFP (pUC) for 22 hours. Claudin 6 MAbs (IM136, IM171, IM172, and IM173) were added at serial dilutions (0.0-10 µg/mL) and incubated for 90 min with shaking. After a wash step, secondary antibody for detection (allophycocyanin-conjugated mouse anti-human IgG Fc; Southern Biotech) was added and incubated for 30-45 min. Cells were washed, and fluorescence was detected by high-throughput Intellicyt flow cytometry, with gating by graphing forward scatter against side scatter. Data were analyzed in GraphPad Prism software based on the geometric mean of fluorescence intensity for the cell population in each well.

Figure 2:
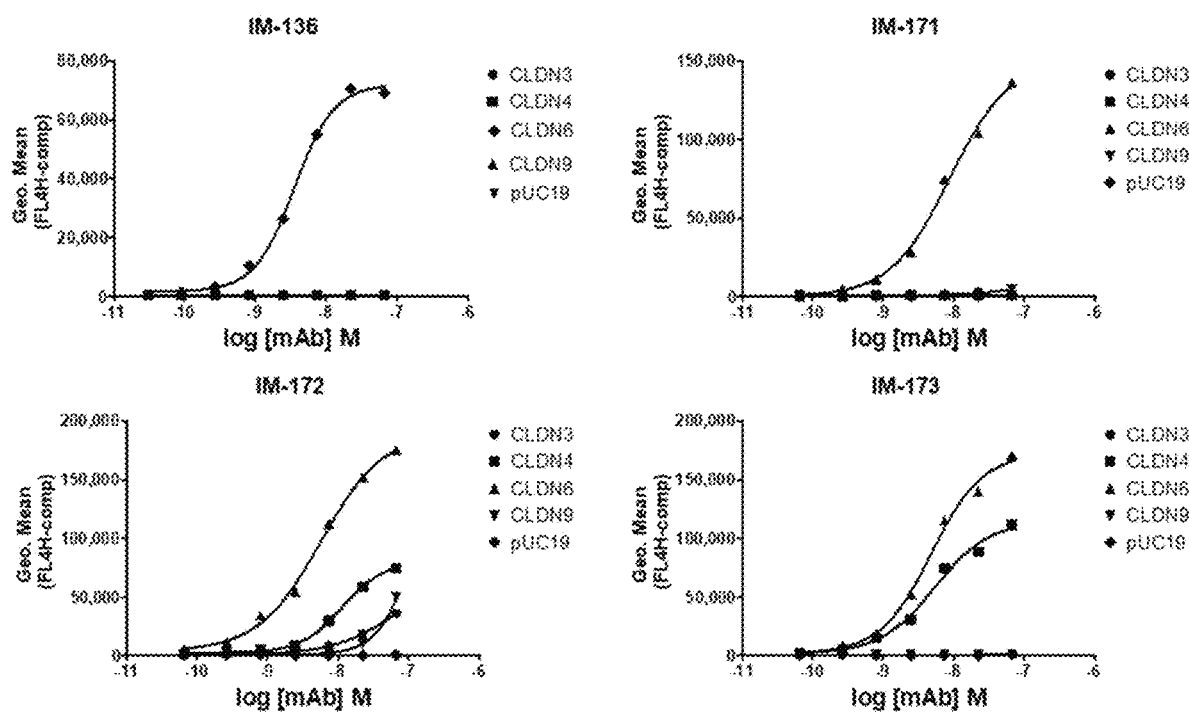
FIG. 2 illustrates various embodiments as provided for herein.

Example 2: Claudin 6 Antibodies Bind Preferentially to Claudin 6 Over Other Claudin Proteins FIG. 2 illustrates the results of a binding assay showing that Claudin 6 MAbs bind to human Claudin 6 preferentially over other Claudin proteins. Human embryonic kidney 293T (HEK-293T) cells were transiently transfected with DNA for the indicated Claudin protein or empty vector along with GFP (pUC) for 22 hours. The results demonstrate that the antibodies can bind preferentially to Claudin 6 over other family members.

Figure 3:
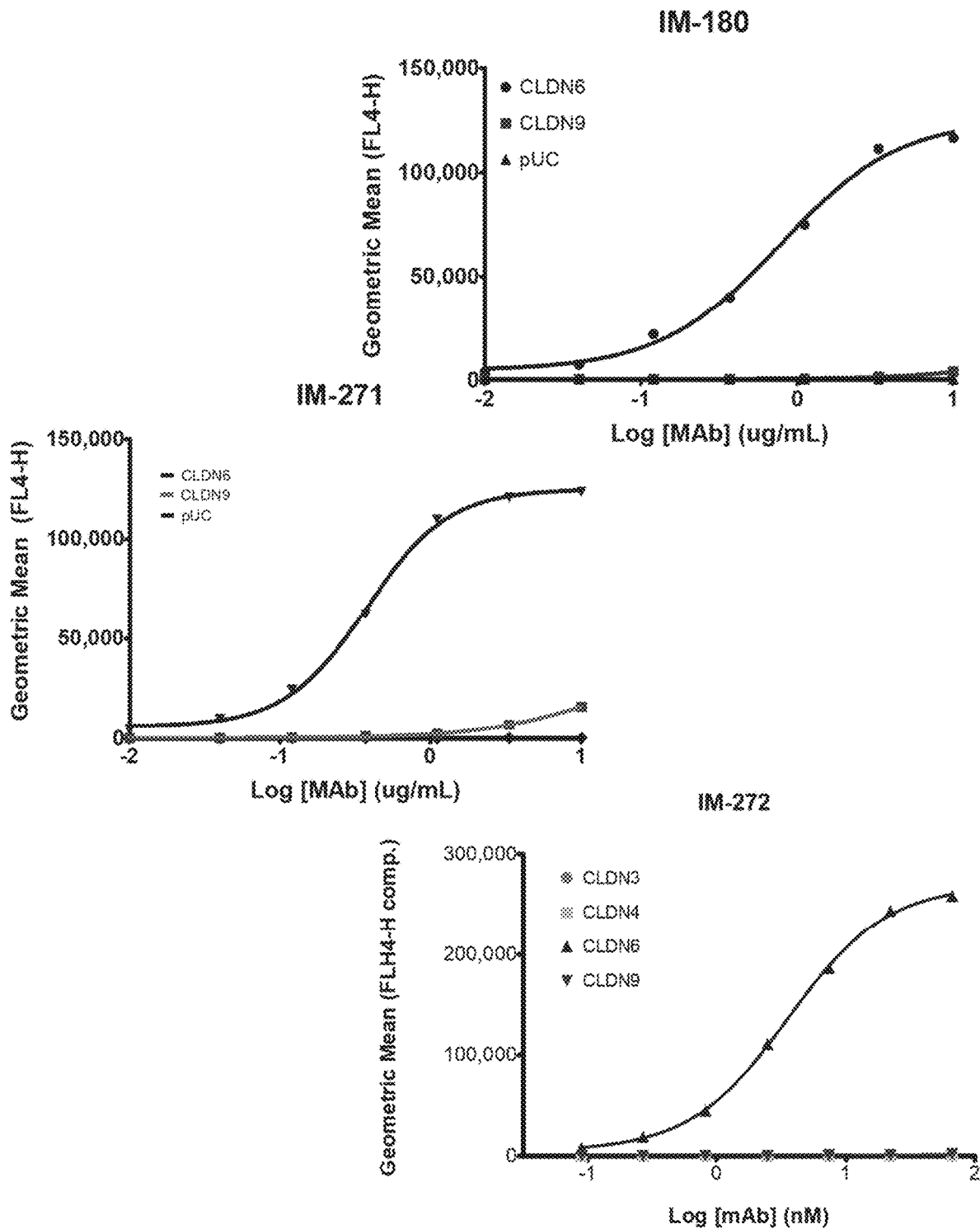
FIG. 3 illustrates various embodiments as provided for herein.

Example 3: Flow Cytometry on HEK-293T Cells Transfected with Plasmids Expressing the Indicated Proteins FIG. 3 illustrates the specificity if the antibodies tested in a flow cytometry method, as performed in Example 2.

Example 4: IM136 and IM171 Binding to PA-1 Cells Naturally Expressing Claudin-6

Figure 4:
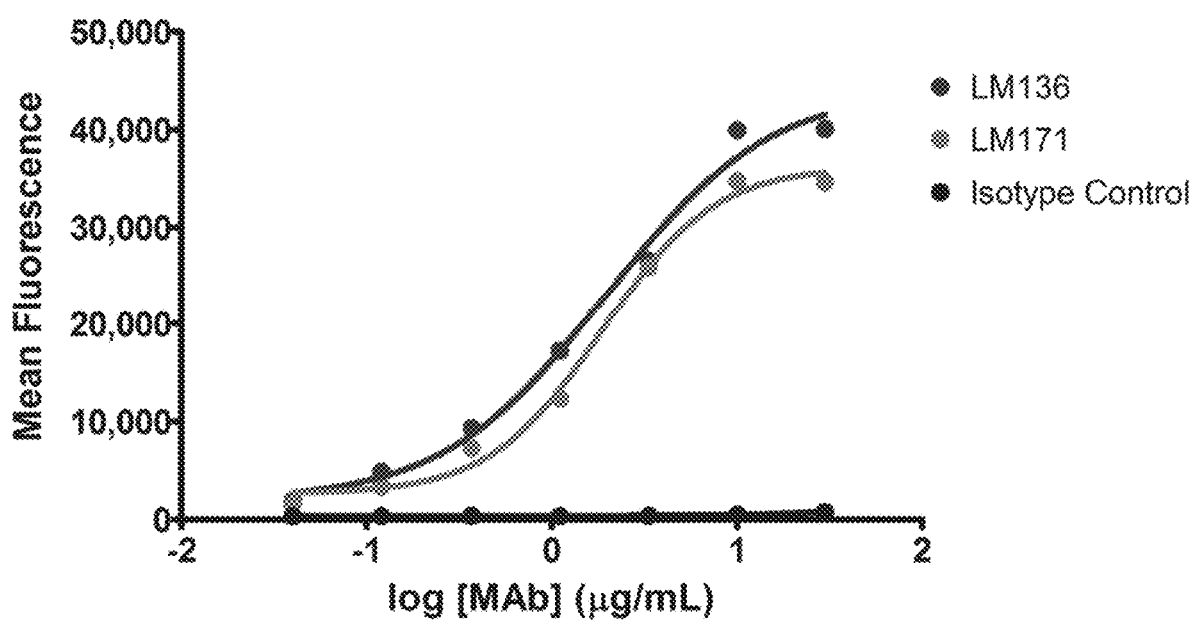
FIG. 4 illustrates various embodiments as provided for herein, including showing that IM136 and IM171 binding to PA-1 cells naturally expressing Claudin-6, which was detected by flow cytometry.

Detection by flow cytometry by staining PA-1 cells with the indicated antibodies. FIG. 4 illustrates antibodies binding to PA-1 cells naturally expressing Claudin-6. Detection by flow cytometry.

Example 5: Antibodies Bind to Cells Naturally Expressing Claudin-6

FIG. 5 illustrates additional antibodies binding to PA-1 cells naturally expressing Claudin-6. Detection by flow cytometry, as performed in Example 4. DENV represents a negative control (anti-Dengue virus) antibody.

Example 6

Figure 6:
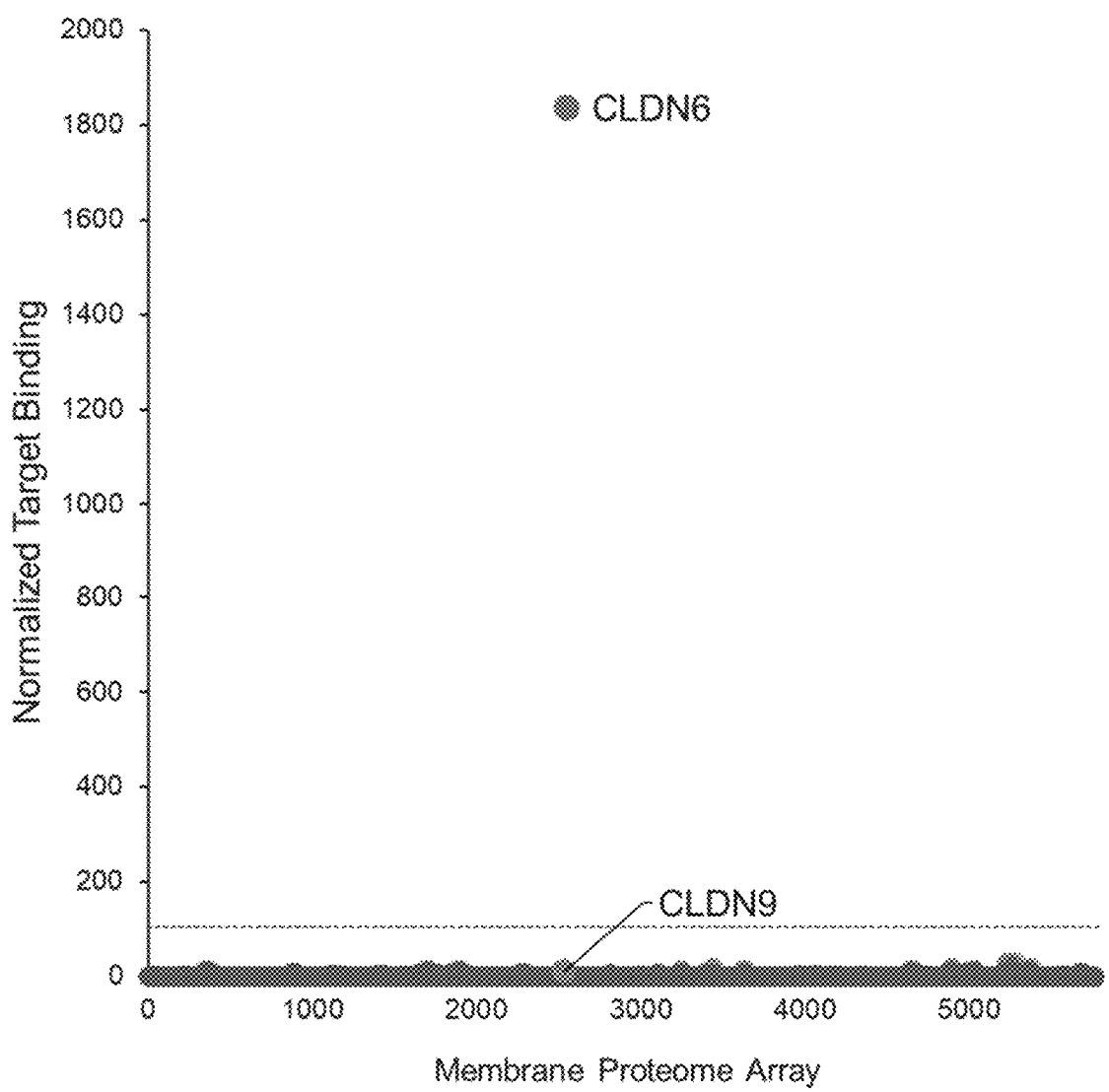
FIG. 6 illustrates various embodiments as provided for herein, including showing that MAb IM171 binding to a proteome array, consisting of 5,300 human membrane proteins expressed in human HEK-293 cells and demonstrating that IM171 is highly specific for Claudin 6.

FIG. 6 illustrates the specificity of Claudin 6 MAb LM171 binding to a membrane proteome array (MPA), consisting of 5,300 human membrane proteins expressed in human HEK-293 cells. Cells were permeabilized with 0.1% saponin, antibody was added to the MPA at 1 ug/ml, and binding across the protein library was measured using high-throughput flow cytometry (Intellicyt HTFC) using a fluorescent secondary antibody. LM171 is highly specific for Claudin 6.

Example 7

Claudin 6 specific antibodies can function with a 'universal' common light chain. Antibodies specific to Claudin 6 were modified to swap the originally identified light chain with a common light chain. The results illustrated in Table 2 below demonstrate that the common light chain can also support binding to Claudin 6 or expression/production of the antibody. The results demonstrate that binding to Claudin 6 is primarily determined by using any of the variable heavy chains and CDRs contained within the same, and that these heavy chains can be paired with these or other common light chains.

TABLE 1

Expression and Binding of claudin6 MAbs. Claudin 6 MAbs produced using their natural light chain, or produced using a different light chain. Yield represents the preparation of the purified MAb and ug of protein resulting from the preparation. Binding represents 66 nM of the indicated MAb binding to HEK-293T cells expressing the target claudin6. The Controls represents the same MAbs staining HEK-293T cells not transfected with claudin6. Staining was detected by flow cytometry (geometric mean fluorescence).

| Target | MAb | Yield (ug) | Binding |
|---|---|---|---|
| CLDN6 | IM179 | 116.2 | N/A |
| CLDN6 | IM179 w/F10 h cLC | 152.0 | N/A |
| CLDN6 | IM 180 | 178.5 | 46,870 |
| CLDN6 | IM180 w/F10 h cLC | 166.3 | 10,085 |
| Control (−CLDN6) | IM180 w/F10 h cLC | 166.3 | 288 |
| CLDN6 | IM271 | 112.6 | 62,993 |
| CLDN6 | IM271 w/F10 h cLC | 124.2 | 160,301 |
| Control (−CLDN6) | IM271 w/F10 h cLC | 124.2 | 312 |

N/A, not available.

Example 8

Identification of critical residues for Ab binding. Shotgun Mutagenesis epitope mapping results. Mean binding reactivities (and ranges) are listed for all identified critical residues. Critical residues for Ab binding (shaded in grey) were residues whose mutations were negative for binding to test Abs (<30% of wild type reactivity), but positive for binding to control 3656 MAb. MAbs 3001-D5 and 3656 are Claudin antibodies that are cross-reactive and bind Claudin 6 and Claudin 9. Thus, the epitope for MAb IM136 includes residues E48, D68, P74, D76, and R158. The epitope for MAb IM171 includes T33, N38, E48, D76, A153, E154, Q156, and R158. The epitope for MAb IM172 includes N38, E48, Y67, P74, D76, D146, V152, E154, Q156, and R158. The epitope for MAb IM173 includes E48, Y67, Q156, and R158. For example, the data illustrates that an antibody that has preferential binding to Claudin6 over Claudin 9 preferentially includes as an epitope residue Q156. The data is illustrated in FIG. 8.

Example 9

Figure 7:
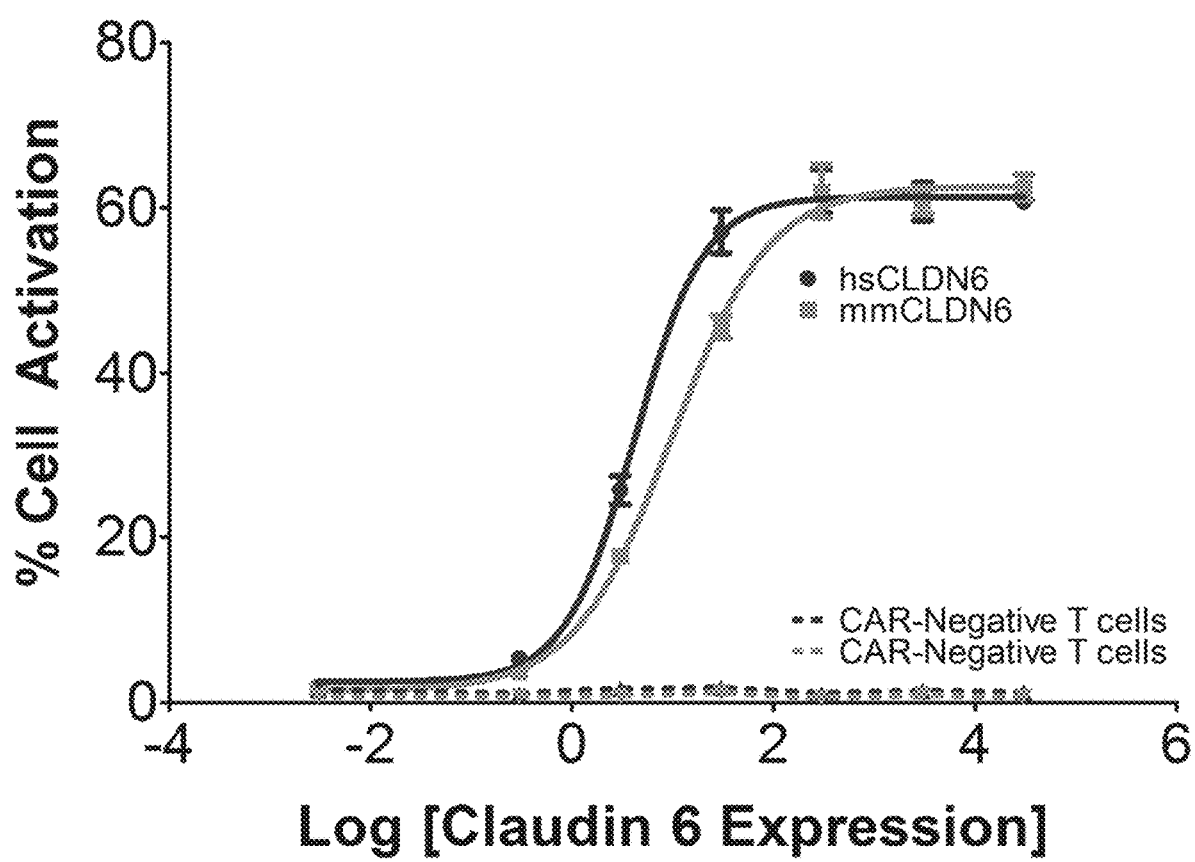
FIG. 7 illustrates various embodiments as provided for herein, including showing that CAR-T cells expressing claudin 6 antibody IM136 are activated by cells expressing human or murine claudin 6. CAR-T cells without the claudin antibody ('CAR-Negative T-cells') are not activated by cells expressing claudin 6. Cell activation is measured by expression of CD69 after overnight co-incubation of the cells, as detected by flow cytometry with an anti-CD69 antibody.

CAR-T cells expressing claudin 6 antibody IM136 are activated by cells expressing human or murine claudin 6. CAR-T cells without the claudin antibody ('CAR-Negative T-cells') are not activated by cells expressing claudin 6. Cell activation is measured by expression of CD69 after overnight co-incubation of the cells, as detected by flow cytometry with an anti-CD69 antibody. The data is illustrated in FIG. 7. The chimeric receptor comprises an extracellular domain comprising a claudin 6 antibody described herein (IM136) as an scFv (VL-linker-VH) fused to the CD8 transmembrane domain, 4-1BB, and CD3zeta signaling domains. This construct is based on the CAR construct reported in Milone et al., Molecular Therapy vol. 17 no. 8, 1453-1464 August 2009, which is hereby incorporated by reference in its entirety.

Example 10: Anti-Claudin 6 Antibodies Bind Specifically to Claudin 6

The table below provides binding information about various antibodies. The antibodies were tested for binding against Claudin 6 as well as demonstrating the specificity of such binding against CLDN9, CLDN4, and CLDN3.

| Antibody | CLDN6 Binding (EC50) | CLDN9 | CLDN4 | CLDN3 |
|---|---|---|---|---|
| IM-271 | less than 4 nM | +/− | − | − |
| IM-271-1HAQ | less than 4 nM | +/− | +/− | − |
| IM-271-1HBG | less than 4 nM | − | − | − |
| IM-271-1HFJ | less than 4 nM | − | − | − |
| IM-271-1HEP | less than 4 nM | − | − | − |
| IM-271-1HHP | less than 4 nM | − | +/− | − |
| IM-35-N1F09-1HA | less than 4 nM | + | + | + |
| IM-271-1HBF | less than 4 nM | − | +/− | − |
| IM-271-1HFB | less than 4 nM | − | − | − |
| IM-271-1HHR | less than 4 nM | − | +/− | +/− |
| IM-271-1HGT | less than 4 nM | + | + | +/− |
| IM-35-N2H07-1HA | less than 4 nM | + | +/− | − |

Affinity of various antibodies against CLDN6 as compared to CLDN9, CLDN3, and CLDN4 was measured using a biosensor. Biosensor affinity measurement of the various antibodies against the proteins was determined using a Forte Octet, which was used for biosensor measurements, using intact claudin proteins embedded in virus-like particles (lipoparticles). The $K_D$ for different antibodies is shown below.

| Antibody | CLDN6 ($K_D$) | CLDN9 ($K_D$) |
|---|---|---|
| IM-136 | 12 nM | 386 nM |
| IM-171 | 3.0 nM | 902 nM |
| IM-172 | Less than 0.1 nM | 81 nM |
| IM-173 | 0.32 nM | N/D |
| Clinical Benchmark | 0.11 nM | 94 nM |

The data demonstrates that the antibodies can bind specifically to Claudin 6 without significant binding to CLDN9, CLDN4, and CLDN3.

In summary, the embodiments and examples demonstrate the production and specificity of Claudin 6 antibodies, which can be used for various methods as provided for herein.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

What is claimed is:

1. An antibody comprising a heavy chain variable region comprising a heavy chain CDR1 (HCDR1), CDR2 (HCDR2), and CDR3 (HCDR3), and a light chain variable region comprising a light chain CDR1 (LCDR1), CDR2 (LCDR2), and CDR3 (LCDR3), and wherein the antibody has:

a HCDR1 of SEQ ID NO: 139, HCDR2 of SEQ ID NO: 140, and HCDR3 of SEQ ID NO: 82, a LCDR1 of SEQ ID NO: 83; a LCDR2 of SEQ ID NO: 84; and a LCDR3 of SEQ ID NO: 85;

a HCDR1 of SEQ ID NO: 141, HCDR2 of SEQ ID NO: 142, and HCDR3 of SEQ ID NO: 57, a LCDR1 of SEQ ID NO: 87; a LCDR2 of SEQ ID NO: 88; and a LCDR3 of SEQ ID NO: 89;

a HCDR1 of SEQ ID NO: 143, HCDR2 of SEQ ID NO: 144, and HCDR3 of SEQ ID NO: 92, a LCDR1 of SEQ ID NO: 93; a LCDR2 of SEQ ID NO: 88; and a LCDR3 of SEQ ID NO: 94;

a HCDR1 of SEQ ID NO: 145, HCDR2 of SEQ ID NO: 146, and HCDR3 of SEQ ID NO: 97, a LCDR1 of SEQ ID NO: 98; a LCDR2 of SEQ ID NO: 99; and a LCDR3 of SEQ ID NO: 100;

a HCDR1 of SEQ ID NO: 25, HCDR2 of SEQ ID NO: 26, and HCDR3 of SEQ ID NO: 27, a LCDR1 of SEQ ID NO: 22; a LCDR2 of SEQ ID NO: 23; and a LCDR3 of SEQ ID NO: 24;

a HCDR1 of SEQ ID NO: 31, HCDR2 of SEQ ID NO: 32, and HCDR3 of SEQ ID NO: 33, a LCDR1 of SEQ ID NO: 28; a LCDR2 of SEQ ID NO: 29; and a LCDR3 of SEQ ID NO: 30;

a HCDR1 of SEQ ID NO: 37, HCDR2 of SEQ ID NO: 38, and HCDR3 of SEQ ID NO: 39, a LCDR1 of SEQ ID NO: 34; a LCDR2 of SEQ ID NO: 29; and a LCDR3 of SEQ ID NO: 36;

a HCDR1 of SEQ ID NO: 43, HCDR2 of SEQ ID NO: 44, and HCDR3 of SEQ ID NO: 45, a LCDR1 of SEQ ID NO: 40; a LCDR2 of SEQ ID NO: 41; and a LCDR3 of SEQ ID NO: 43;

a HCDR1 of SEQ ID NO: 25, HCDR2 of SEQ ID NO: 26, and HCDR3 of SEQ ID NO: 27, a LCDR1 of SEQ ID NO: 22; a LCDR2 of SEQ ID NO: 23; and a LCDR3 of SEQ ID NO: 24;

a HCDR1 of SEQ ID NO: 31, HCDR2 of SEQ ID NO: 46, and HCDR3 of SEQ ID NO: 33, a LCDR1 of SEQ ID NO: 28; a LCDR2 of SEQ ID NO: 29; and a LCDR3 of SEQ ID NO: 30;

a HCDR1 of SEQ ID NO: 37, HCDR2 of SEQ ID NO: 48, and HCDR3 of SEQ ID NO: 39, a LCDR1 of SEQ ID NO: 47; a LCDR2 of SEQ ID NO: 29; and a LCDR3 of SEQ ID NO: 36;

a HCDR1 of SEQ ID NO: 43, HCDR2 of SEQ ID NO: 49, and HCDR3 of SEQ ID NO: 45, a LCDR1 of SEQ ID NO: 40; a LCDR2 of SEQ ID NO: 41; and a LCDR3 of SEQ ID NO: 42;

a HCDR1 of SEQ ID NO: 53, HCDR2 of SEQ ID NO: 54, and HCDR3 of SEQ ID NO: 33, a LCDR1 of SEQ ID NO: 50; a LCDR2 of SEQ ID NO: 51; and a LCDR3 of SEQ ID NO: 52;

a HCDR1 of SEQ ID NO: 55, HCDR2 of SEQ ID NO: 54, and HCDR3 of SEQ ID NO: 33, a LCDR1 of SEQ ID NO: 50; a LCDR2 of SEQ ID NO: 51; and a LCDR3 of SEQ ID NO: 52;

a HCDR1 of SEQ ID NO: 56, HCDR2 of SEQ ID NO: 101, and HCDR3 of SEQ ID NO: 57, a LCDR1 of SEQ ID NO: 58; a LCDR2 of SEQ ID NO: 59; and a LCDR3 of SEQ ID NO: 60;

a HCDR1 of SEQ ID NO: 56, HCDR2 of SEQ ID NO: 101, and HCDR3 of SEQ ID NO: 61, a LCDR1 of SEQ ID NO: 58; a LCDR2 of SEQ ID NO: 59; and a LCDR3 of SEQ ID NO: 60;

a HCDR1 of SEQ ID NO: 62, HCDR2 of SEQ ID NO: 101, and HCDR3 of SEQ ID NO: 63, a LCDR1 of SEQ ID NO: 64; a LCDR2 of SEQ ID NO: 59; and a LCDR3 of SEQ ID NO: 60;

a HCDR1 of SEQ ID NO: 62, HCDR2 of SEQ ID NO: 101, and HCDR3 of SEQ ID NO: 65, a LCDR1 of SEQ ID NO: 64; a LCDR2 of SEQ ID NO: 59; and a LCDR3 of SEQ ID NO: 60;

a HCDR1 of SEQ ID NO: 62, HCDR2 of SEQ ID NO: 101, and HCDR3 of SEQ ID NO: 66, a LCDR1 of SEQ ID NO: 64; a LCDR2 of SEQ ID NO: 59; and a LCDR3 of SEQ ID NO: 60;

a HCDR1 of SEQ ID NO: 62, HCDR2 of SEQ ID NO: 101, and HCDR3 of SEQ ID NO: 67, a LCDR1 of SEQ ID NO: 64; a LCDR2 of SEQ ID NO: 59; and a LCDR3 of SEQ ID NO: 60;

a HCDR1 of SEQ ID NO: 62, HCDR2 of SEQ ID NO: 101, and HCDR3 of SEQ ID NO: 65, a LCDR1 of SEQ ID NO: 58; a LCDR2 of SEQ ID NO: 68; and a LCDR3 of SEQ ID NO: 60;

a HCDR1 of SEQ ID NO: 62, HCDR2 of SEQ ID NO: 101, and HCDR3 of SEQ ID NO: 126, a LCDR1 of SEQ ID NO: 58; a LCDR2 of SEQ ID NO: 68; and a LCDR3 of SEQ ID NO: 60;

a HCDR1 of SEQ ID NO: 62, HCDR2 of SEQ ID NO: 101, and HCDR3 of SEQ ID NO: 69, a LCDR1 of SEQ ID NO: 58; a LCDR2 of SEQ ID NO: 68; and a LCDR3 of SEQ ID NO: 60;

a HCDR1 of SEQ ID NO: 62, HCDR2 of SEQ ID NO: 101, and HCDR3 of SEQ ID NO: 69, a LCDR1 of SEQ ID NO: 64; a LCDR2 of SEQ ID NO: 59; and a LCDR3 of SEQ ID NO: 70;

a HCDR1 of SEQ ID NO: 71, HCDR2 of SEQ ID NO: 72, and HCDR3 of SEQ ID NO: 73, a LCDR1 of SEQ ID NO: 74; a LCDR2 of SEQ ID NO: 59; and a LCDR3 of SEQ ID NO: 75;

a HCDR1 of SEQ ID NO: 76, HCDR2 of SEQ ID NO: 77, and HCDR3 of SEQ ID NO: 78, a LCDR1 of SGGSGSYGYYG SEQ ID NO: 147; a LCDR2 of SEQ ID NO: 59; and a LCDR3 of SEQ ID NO: 79;

a HCDR1 of SEQ ID NO: 80, HCDR2 of SEQ ID NO: 81, and HCDR3 of SEQ ID NO: 82, a LCDR1 of SEQ ID NO: 83; a LCDR2 of SEQ ID NO: 84; and a LCDR3 of SEQ ID NO: 85;

a HCDR1 of SEQ ID NO: 62, HCDR2 of SEQ ID NO: 86, and HCDR3 of SEQ ID NO: 57, a LCDR1 of SEQ ID NO: 87; a LCDR2 of SEQ ID NO: 88; and a LCDR3 of SEQ ID NO: 89;

a HCDR1 of SEQ ID NO: 90, HCDR2 of SEQ ID NO: 91, and HCDR3 of SEQ ID NO: 92, a LCDR1 of SEQ ID NO: 93; a LCDR2 of SEQ ID NO: 88 and a LCDR3 of SEQ ID NO: 94;

a HCDR1 of SEQ ID NO: 95, HCDR2 of SEQ ID NO: 96, and HCDR3 of SEQ ID NO: 97, a LCDR1 of SEQ ID NO: 98; a LCDR2 of SEQ ID NO: 99; and a LCDR3 of SEQ ID NO: 100;

a HCDR1 of SEQ ID NO: 62, HCDR2 of SEQ ID NO: 101, and HCDR3 of SEQ ID NO: 57, a LCDR1 of SEQ ID NO: 58; a LCDR2 of SEQ ID NO: 59; and a LCDR3 of SEQ ID NO: 60; or a HCDR1 of SEQ ID NO: 62, HCDR2 of SEQ ID NO: 102, and HCDR3 of SEQ ID NO: 57, a LCDR1 of SEQ ID NO: 87; a LCDR2 of SEQ ID NO: 88; and a LCDR3 of SEQ ID NO: 89.

2. A nucleic acid molecule encoding an antibody of claim 1.

3. A pharmaceutical composition comprising the antibody of claim 1, or a nucleic acid molecule encoding the same.

4. The antibody of claim 1, wherein the antibody comprises a HCDR1 of SEQ ID NO: 53, a HCDR2 of SEQ ID NO: 54, a HCDR3 of SEQ ID NO: 33, a LCDR1 of SEQ ID NO: 50; a LCDR2 of SEQ ID NO: 51; and a LCDR3 of SEQ ID NO: 52.

5. The antibody of claim 1, wherein the antibody comprises:

a) a light chain variable region having at least 90% identity to the amino acid sequence of SEQ ID NO: 19, the light chain variable region comprising:
  i. a light chain CDR1 having the amino acid sequence of SEQ ID NO: 50;
  ii. a light chain CDR2 having the amino acid sequence of SEQ ID NO: 51;
  iii. a light chain CDR3 having the amino acid sequence of SEQ ID NO: 52; and
b) a heavy chain variable region having at least 90% identity to the amino acid sequence of SEQ ID NO: 18, the heavy chain variable region comprising:
  i. a heavy chain CDR1 having the amino acid sequence of SEQ ID NO: 53;
  ii. a heavy chain CDR2 having the amino acid sequence of SEQ ID NO: 54;
  iii. a heavy chain CDR3 having the amino acid sequence of SEQ ID NO: 33.

6. The antibody of claim 5, wherein the light chain variable region has at least 95% identity to the amino acid sequence of SEQ ID NO: 19, and the heavy chain variable region has at least 95% identity to the amino acid sequence of SEQ ID NO: 20.

7. The antibody of claim 1, wherein the antibody comprises a light chain variable region having at least 90% identity to the amino acid sequence of SEQ ID NO: 19, the light chain variable region comprising:
  i. a light chain CDR1 having the amino acid sequence of SEQ ID NO: 50;
  ii. a light chain CDR2 having the amino acid sequence of SEQ ID NO: 51; and
  iii. a light chain CDR3 having the amino acid sequence of SEQ ID NO: 52.

8. The antibody of claim 7, wherein the light chain variable region has at least 95% identity to the amino acid sequence of SEQ ID NO: 19.

9. The antibody of claim 1, wherein the antibody comprises a HCDR1 of SEQ ID NO:
  62, a HCDR2 of SEQ ID NO: 125, a HCDR3 of SEQ ID NO: 69, a LCDR1 of SEQ ID NO: 58; a LCDR2 of SEQ ID NO: 68; and a LCDR3 of SEQ ID NO: 60.

10. The antibody of claim 1, wherein the antibody comprises a HCDR1 of SEQ ID NO:
  62, a HCDR2 of SEQ ID NO: 125, a HCDR3 of SEQ ID NO: 67, a LCDR1 of SEQ ID NO: 64; a LCDR2 of SEQ ID NO: 59; and a LCDR3 of SEQ ID NO: 60.

11. The antibody of claim 1, wherein the antibody comprises:
a) a light chain variable region having at least 90% identity to the amino acid sequence of SEQ ID NO: 118, the light chain variable region comprising:
  i. a light chain CDR1 having the amino acid sequence of SEQ ID NO: 58;
  ii. a light chain CDR2 having the amino acid sequence of SEQ ID NO: 68;
  iii. a light chain CDR3 having the amino acid sequence of SEQ ID NO: 60, and
b) a heavy chain variable region having at least 90% identity to the amino acid sequence of SEQ ID NO: 117, the heavy chain variable region comprising:
  i. a heavy chain CDR1 having the amino acid sequence of SEQ ID NO: 62;
  ii. a heavy chain CDR2 having the amino acid sequence of SEQ ID NO: 125;
  iii. a heavy chain CDR3 having the amino acid sequence of SEQ ID NO: 69.

12. The antibody of claim 11, wherein the light chain variable region has at least 95% identity to the amino acid sequence of SEQ ID NO: 118, and the heavy chain variable region has at least 95% identity to the amino acid sequence of SEQ ID NO: 117.

13. The antibody of claim 1, wherein the antibody comprises:
  a) a light chain variable region having at least 90% identity to the amino acid sequence of SEQ ID NO: 112, the light chain variable region comprising:
    i. a light chain CDR1 having the amino acid sequence of SEQ ID NO: 64;
    ii. a light chain CDR2 having the amino acid sequence of SEQ ID NO: 59;
    iii. a light chain CDR3 having the amino acid sequence of SEQ ID NO: 60, and
  b) a heavy chain variable region having at least 90% identity to the amino acid sequence of SEQ ID NO: 111, the heavy chain variable region comprising:
    i. a heavy chain CDR1 having the amino acid sequence of SEQ ID NO: 62;
    ii. a heavy chain CDR2 having the amino acid sequence of SEQ ID NO: 125;
    iii. a heavy chain CDR3 having the amino acid sequence of SEQ ID NO: 67.

14. The antibody of claim 13, wherein the light chain variable region has at least 95% identity to the amino acid sequence of SEQ ID NO: 112, and the heavy chain variable region has at least 95% identity to the amino acid sequence of SEQ ID NO: 111.

15. The antibody of claim 1, wherein the antibody comprises a HCDR1 of SEQ ID NO:
  62, a HCDR2 of SEQ ID NO: 125, a HCDR3 of SEQ ID NO: 66, a LCDR1 of SEQ ID NO: 64; a LCDR2 of SEQ ID NO: 59; and a LCDR3 of SEQ ID NO: 60.

16. The antibody of claim 1, wherein the antibody comprises:
  a) a light chain variable region having at least 90% identity to the amino acid sequence of SEQ ID NO: 110, the light chain variable region comprising:
    i. a light chain CDR1 having the amino acid sequence of SEQ ID NO: 64;
    ii. a light chain CDR2 having the amino acid sequence of SEQ ID NO: 59;
    iii. a light chain CDR3 having the amino acid sequence of SEQ ID NO: 60, and
  b) a heavy chain variable region having at least 90% identity to the amino acid sequence of SEQ ID NO: 109, the heavy chain variable region comprising:
    i. a heavy chain CDR1 having the amino acid sequence of SEQ ID NO: 62;
    ii. a heavy chain CDR2 having the amino acid sequence of SEQ ID NO: 125;
    iii. a heavy chain CDR3 having the amino acid sequence of SEQ ID NO: 66.

17. The antibody of claim 16, wherein the light chain variable region has at least 95% identity to the amino acid sequence of SEQ ID NO: 110, and the heavy chain variable region has at least 95% identity to the amino acid sequence of SEQ ID NO: 109.

18. The antibody of claim 1, wherein the antibody comprises a light chain variable region having at least 90% identity to the amino acid sequence of SEQ ID NO: 110, the light chain variable region comprising:
  i. a light chain CDR1 having the amino acid sequence of SEQ ID NO: 64;
  ii. a light chain CDR2 having the amino acid sequence of SEQ ID NO: 59;
  iii. a light chain CDR3 having the amino acid sequence of SEQ ID NO: 60.

19. The antibody of claim 18, wherein the light chain variable region has at least 95% identity to the amino acid sequence of SEQ ID NO: 110.

20. The antibody of claim 1, wherein the antibody comprises a HCDR1 of SEQ ID NO: 62, a HCDR2 of SEQ ID NO: 125, a HCDR3 of SEQ ID NO: 65, a LCDR1 of SEQ ID NO: 64; a LCDR2 of SEQ ID NO: 59; and a LCDR3 of SEQ ID NO: 60.

21. The antibody of claim 1, wherein the antibody comprises:
  a) a light chain variable region having at least 90% identity to the amino acid sequence of SEQ ID NO: 108, the light chain variable region comprising:
    i. a light chain CDR1 having the amino acid sequence of SEQ ID NO: 64;
    ii. a light chain CDR2 having the amino acid sequence of SEQ ID NO: 59;
    iii. a light chain CDR3 having the amino acid sequence of SEQ ID NO: 60, and
  b) a heavy chain variable region having at least 90% identity to the amino acid sequence of SEQ ID NO: 107, the heavy chain variable region comprising:
    i. a heavy chain CDR1 having the amino acid sequence of SEQ ID NO: 62;
    ii. a heavy chain CDR2 having the amino acid sequence of SEQ ID NO: 125;
    iii. a heavy chain CDR3 having the amino acid sequence of SEQ ID NO: 65.

22. The antibody of claim 21, wherein the light chain variable region has at least 95% identity to the amino acid sequence of SEQ ID NO: 107, and the heavy chain variable region has at least 95% identity to the amino acid sequence of SEQ ID NO: 108.

23. The antibody of claim 1, wherein the antibody comprises a light chain variable region having at least 90% identity to the amino acid sequence of SEQ ID NO: 108, the light chain variable region comprising:
  i. a light chain CDR1 having the amino acid sequence of SEQ ID NO: 64;
  ii. a light chain CDR2 having the amino acid sequence of SEQ ID NO: 59; and,
  iii. a light chain CDR3 having the amino acid sequence of SEQ ID NO: 60.

24. The antibody of claim 23, wherein the light chain variable region has at least 95% identity to the amino acid sequence of SEQ ID NO: 108.

25. A cell comprising the nucleic acid molecule of claim 2.

* * * * *

UNITED STATES PATENT AND TRADEMARK OFFICE
CERTIFICATE OF CORRECTION

| | |
|---|---|
| PATENT NO. | : 11,248,046 B2 |
| APPLICATION NO. | : 16/790066 |
| DATED | : February 15, 2022 |
| INVENTOR(S) | : Ross Chambers et al. |

It is certified that error appears in the above-identified patent and that said Letters Patent is hereby corrected as shown below:

In the Claims

In Claim 6, Column 182, Line 24, replace:
"of SEQ ID NO: 20."
With:
--of SEQ ID NO: 18.--

Signed and Sealed this
Nineteenth Day of July, 2022

Katherine Kelly Vidal
*Director of the United States Patent and Trademark Office*